United States Patent
Stratton et al.

(10) Patent No.: US 10,588,757 B2
(45) Date of Patent: Mar. 17, 2020

(54) SYSTEM FOR PROCESSING BONE STOCK INCLUDING A BONE CLEANING HEAD, A BONE MILLING HEAD AND BASE THAT POWERS BOTH THE CLEANING HEAD AND THE MILLING HEAD

(71) Applicant: Stryker Corporation, Kalamazoo, MI (US)

(72) Inventors: Dennis Stratton, Plainwell, MI (US); Eric K. Diehl, Austin, TX (US); John P. Bernero, Round Rock, TX (US); Chris Chamberlin, Austin, TX (US); Vincent Lam, San Antonio, TX (US); Austin Orand, Portland, OR (US); David J. Veldkamp, Grand Rapids, MI (US); Eric M. Heffernan, Kalamazoo, MI (US); David S. Goldenberg, Mattawan, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/915,562

(22) Filed: Mar. 8, 2018

(65) Prior Publication Data
US 2018/0193170 A1 Jul. 12, 2018

Related U.S. Application Data

(60) Continuation of application No. 15/174,281, filed on Jun. 6, 2016, now Pat. No. 10,045,863, which is a
(Continued)

(51) Int. Cl.
*A61B 17/00* (2006.01)
*A61F 2/46* (2006.01)

(52) U.S. Cl.
CPC .... *A61F 2/4644* (2013.01); *A61F 2002/4645* (2013.01); *A61F 2002/4646* (2013.01)

(58) Field of Classification Search
CPC combination set(s) only.
See application file for complete search history.

(56) References Cited

U.S. PATENT DOCUMENTS

| 5,977,432 A | 11/1999 | Wolfinbarger, Jr. et al. |
| 6,017,354 A | 1/2000 | Culp et al. |

(Continued)

FOREIGN PATENT DOCUMENTS

| JP | 2004509631 A | 4/2004 |
| JP | 2008534191 A | 8/2008 |

OTHER PUBLICATIONS

English language abstract for JP 2004-509631 extracted from espacenet.com database on Nov. 15, 2017, 2 pages.
(Continued)

*Primary Examiner* — Sameh R Boles
(74) *Attorney, Agent, or Firm* — Howard & Howard Attorneys PLLC

(57) ABSTRACT

A system for cleaning bone that includes a base unit with a motor, a cleaning head with a cleaning element and a mill head with a mill element. Both the cleaning head and the mill head are designed to be coupled to the base unit. Both the cleaning element and mill element have features that facilitate their coupling to the motor. When the cleaning head is attached to the base unit, a motor in the base unit rotates the cleaning element to remove soft tissue from the bone so as to clean the bone. The mill element is placed on the base unit and the cleaned bone placed in the mill head. The actuation of the base unit motor results in the actuations of the mill element. The actuation of the mill element converts the cleaned bone into bone chips.

27 Claims, 47 Drawing Sheets

Related U.S. Application Data division of application No. 14/157,975, filed on Jan. 17, 2014, now Pat. No. 9,370,436, which is a division of application No. 13/462,120, filed on May 2, 2012, now Pat. No. 8,672,942, which is a continuation of application No. PCT/US2010/055646, filed on Nov. 5, 2010.

(60) Provisional application No. 61/258,667, filed on Nov. 6, 2009.

(56) References Cited

U.S. PATENT DOCUMENTS

| | | |
|---|---|---|
| 6,217,614 B1 | 4/2001 | Fages et al. |
| 6,287,312 B1 | 9/2001 | Clokie et al. |
| 6,755,365 B1 | 6/2004 | Meredith |
| 6,824,087 B2 | 11/2004 | McPherson et al. |
| 7,029,387 B2 | 4/2006 | van den Nieuwelaar et al. |
| 7,131,605 B2 | 11/2006 | McPherson et al. |
| 7,422,582 B2 | 9/2008 | Malackowski et al. |
| 8,512,342 B2 | 8/2013 | Meredith |
| 8,622,953 B2 | 1/2014 | Hynes et al. |
| 8,672,942 B2 | 3/2014 | Chamberlin et al. |
| 9,370,436 B2 | 6/2016 | Stratton |
| 2006/0138260 A1 | 6/2006 | Hay et al. |
| 2007/0164137 A1 | 7/2007 | Rasekhi |
| 2008/0274682 A1 | 11/2008 | Iversen |
| 2009/0118713 A1 | 5/2009 | Munson |
| 2009/0118735 A1 | 5/2009 | Burmeister, III et al. |
| 2010/0291506 A1 | 11/2010 | Olsson et al. |
| 2011/0166503 A1* | 7/2011 | Koltz .................... A22C 17/04 604/22 |
| 2016/0278942 A1 | 9/2016 | Stratton et al. |

OTHER PUBLICATIONS

English language abstract and machine-assisted English translation for JP 2008-534191 extracted from espacenet.com database on Nov. 15, 2017, 24 pages.

PCT App. No. PCT/US2010/055646 "International Search Report and Written Opinion", dated Feb. 28, 2011.

* cited by examiner

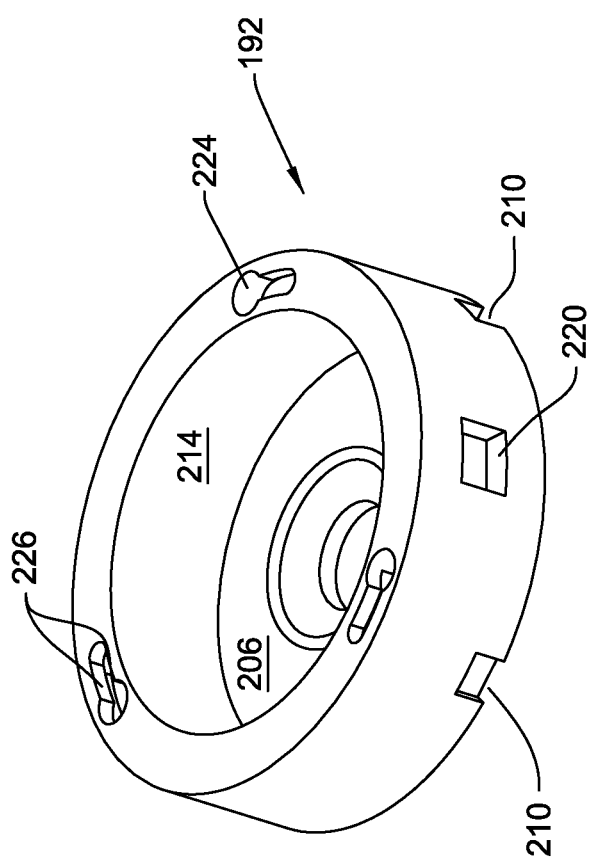

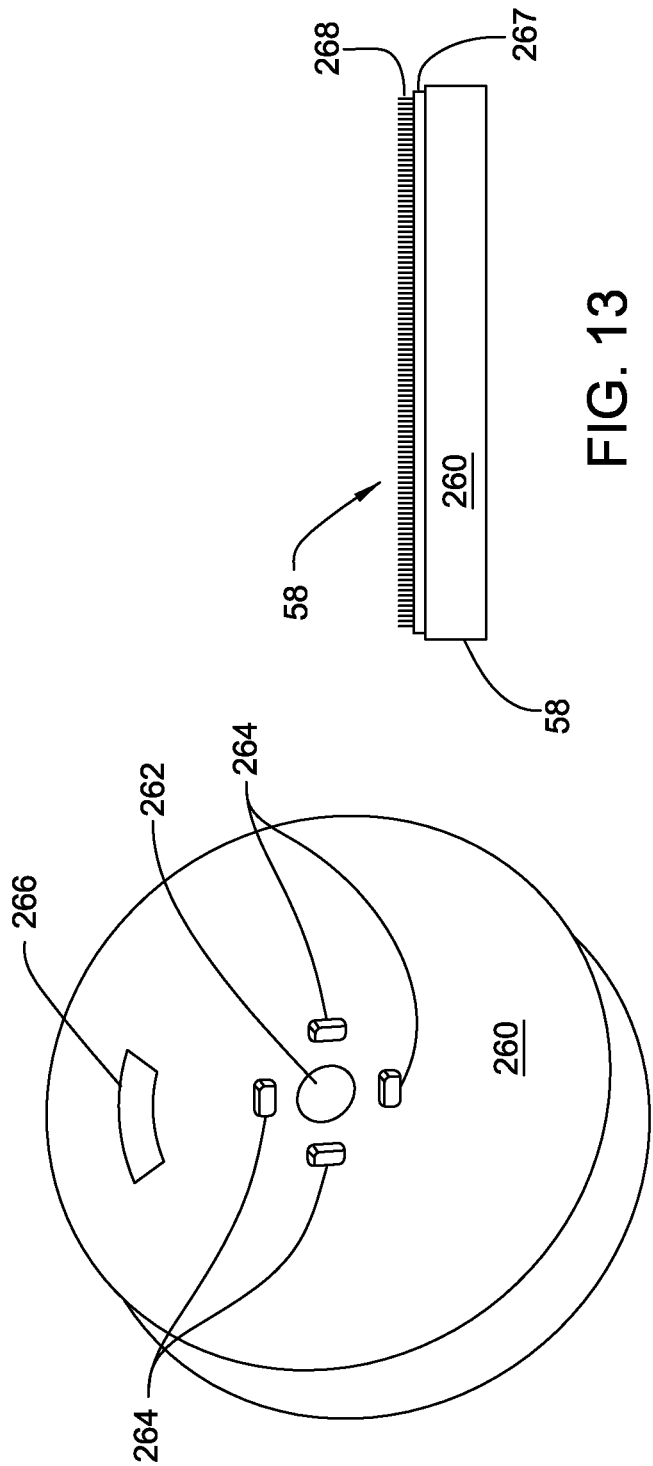

| DEVICE IDENTIFICATION | 273 |
|---|---|
| USE Y/N | 274 |
| MINIMUN SPEED | 275 |
| DEFAULT SPEED | 276 |
| MAXIMUN SPEED | 277 |
| DIRECTION | 278 |

SYSTEM FOR PROCESSING BONE STOCK INCLUDING A BONE CLEANING HEAD, A BONE MILLING HEAD AND BASE THAT POWERS BOTH THE CLEANING HEAD AND THE MILLING HEAD

RELATIONSHIP TO EARLIER FILED APPLICATIONS

This application is a continuation of U.S. patent application Ser. No. 15/174,281 filed 6 Jun. 2016. U.S. patent application Ser. No. 15/174,281 is a divisional of U.S. patent application Ser. No. 14/157,975 filed 17 Jan. 2014, now U.S. Pat. No. 9,370,436. U.S. patent application Ser. No. 14/157,975 is a divisional of U.S. patent application Ser. No. 13/462,120 filed 2 May 2012, now U.S. Pat. No. 8,672,942. U.S. patent application Ser. No. 13/462,120 is a continuation of PCT Application No. PCT/US2010/055646 filed 5 Nov. 2010. PCT Application No. PCT/US2010/055646 is a non-provisional of U.S. Provisional App. No. 61/258,667 filed 6 Nov. 2009. The contents of the above-listed priority applications are explicitly incorporated herein by reference.

FIELD OF THE INVENTION

This invention is directed to a system that first cleans bone stock and, once the bone stock is cleaned, mills the bone to form bone chips.

BACKGROUND OF THE INVENTION

There are a number of different surgical procedures in which chip-sized bone is used as filler adjacent other sections of bone. For example, in a spinal fusion procedure, it is a known practice to place a compound formed out of milled bone around the rods used to hold adjacent vertebra in alignment. This compound serves as a lattice upon which the tissues forming the vertebra grow so as to form a foundation of bone around the rods. This foundation distributes the load imposed on the rods. Bone chips are also used as filler and/or growth formation lattice in orthopedic surgical procedures and other procedures such as maxillofacial procedures.

Bone chips are used as a filler/growth formation lattice in these procedures because the material, the proteins from which the bone is formed, serves as make-up material from which the blast cells of the adjacent living bone cells form new bone.

The ideal source of stock for bone chips is the patient into which the bone chips are to be packed. This is because the patient's own bone, own tissue, is less likely to be rejected by the patient's immune system than donor bone. Accordingly, in a procedure in which bone chips are required, the bone stock often harvested from one of the patient's bones afford to lose a small section of bone, typically between 0.25 and 3 cm³. Bone that is removed from the patient for transplant into another part of the patient is referred to as autograft bone.

Once the bone is harvested, it is cleaned. After cleaning, the bone is milled to form chips. The Applicant's Assignee's U.S. Patent Pub. No. US 2009/011735 A1/PCT Pub. No. WO 2009/061728 A1, BONE MILL INCLUDING A BASE AND A MILL HEAD SEPARATE FROM THE BASE, THE MILL HEAD INCLUDING A REMOVABLE CATCH TRAY, the contents of which are explicitly incorporated herein by reference, discloses a bone mill capable of converting bone stock into bone chips. This bone mill includes a base with a motor. A mill head, that contains the bone milling components, is removably attached to the base. When the head is attached to the base, the motor engages at least one of the milling components. Actuation of the motor results in a like actuation of the milling component. This results of conversion of bone stock into bone chips.

The bone mill of the incorporated by reference publication is understood to perform a more than adequate job of milling bone stock into bone chips. Nevertheless, prior to this process, it is still necessary to clean the bone to remove ligaments and other tissue that are not suitable stock for forming bone chips. Presently, surgical personnel perform this task manually using curettes, rongeurs, brushes and/or cobbs. It may take 15 minutes or more for surgical personnel to perform this process.

Moreover, to perform the cleaning process, the surgical personnel may need to firmly grasp the bone. Exerting such force on the bone may cause tearing of the gloves worn by the surgical personnel. Such tearing could result in the possibility that skin of the surgical personnel may come into direct contact with the bone. This contact can result in contamination of the bone.

SUMMARY OF THE INVENTION

This invention is related to a new and useful system for first cleaning bone and, once the bone is cleaned, milling the bone to form bone chips.

One version of the system of this invention includes: a base unit; a cleaning head; and a mill head. Internal to the base unit is a motor. The base unit also includes components for releasably holding first the cleaning head and then the mill head. Internal to the cleaning head is at least one cleaning element. In some embodiments, the cleaning element is a moveable brush, a rotating grater, and/or a rotating fluted screw. Attached to the cleaning element are features that releasably couple the cleaning element to the base unit motor. Internal to the mill head is a moveable mill element. The mill element is designed to, when actuated, mill bone stock into bone chips. The mill element includes features for releasably coupling the mill element to the base unit motor.

The system of this invention is employed to convert harvested bone stock into bone chips by first coupling the cleaning head to the base. The harvested bone stock is placed in the cleaning head. The base unit motor is actuated to cause a like actuation of the cleaning head cleaning element. The movement of the cleaning element against the bone stock removes the ligaments, muscle, connective tissue and other debris material from the surface of the bone stock.

Once the bone stock is cleaned, the cleaning head is removed from the base unit. The mill head is fitted to the base unit. The bone stock is placed in the mill head. The base unit motor is actuated cause a like actuation of the mill element. Actuation of the mill element converts the bone stock into bone chips suitable for implantation into the patient.

The integrated system of this invention includes components for both cleaning and milling the bone stock. By having the mechanized cleaning head perform the cleaning process, the need for operating room personnel to perform this task is eliminated. In many situations, the cleaning head cleans bone stock in less time than it takes an individual to perform the same task.

Still another advantage of the integrated system of this invention is that a single unit, the base unit, provides the motive power needed to actuate the cleaning element internal to the cleaning head and the mill element internal to the mill head. The need to provide essentially duplicative power units, one for each head, is eliminated.

In an alternative version of the invention, a single head is attached to the base. The head has a module with a brush for cleaning the bone. Below the cleaning module, the head has a mill module. Internal to the mill module are components for milling the bone stock into chips. The mill module is dimensioned to be removably coupled to the base unit. The modules have components that, when the head is attached to the base unit, couple the brush and moving mill element to the motor internal to base unit. In one embodiment of this version of the invention, the cleaning module is moveable relative to the mill module.

The alternative version of the invention is prepared for use by coupling the head to the base. The harvested bone stock is placed in the cleaning head. The base unit motor is actuated. The motor drives the brush internal to the head so as to clean the bone. Once the bone is cleaned, the cleaning module is moved to a position in which it is directed to feed port integral with the mill module. The cleaned bone is discharged from the cleaning module into the mill module. Once the bone is so transferred to the mill module, the motor is again actuated. As a result of this actuation of the motor, the consequential actuation of the mill element converts the previously cleaned bone stock into bone chips.

An assembly for cleaning bone stock includes a base. A shell is supported by the base for defining a void space for receiving the bone stock to be cleaned. At least one cleaning element is disposed in the void space. A drive assembly is coupled to the at least one cleaning element to actuate the at least one cleaning element to clean the bone stock. In some embodiments, the cleaning element is a rotating brush, a rotating grater, and/or a rotating fluted screw.

A further advantage of the above alternative versions of the invention is that once the bone stock is placed in the cleaning head, the need for surgical personnel to handle bone is substantially eliminated.

BRIEF DESCRIPTION OF THE DRAWINGS

The invention is pointed out with particularity in the claims. The above and further features and advantages of this invention are better understood by the following detailed description taken in conjunction with the following drawings in which:

FIG. 8 is a perspective view of the lower shell of the cleaning head;

FIG. 12 is a perspective view of the bottom surface of the substrate of the cleaning head lower brush;

FIG. 13 is a side view of the cleaning head lower brush;

FIG. 51A is a top perspective view of the rotating grater of FIG. 50;

DETAILED DESCRIPTION

I. Overview

Figure 1:
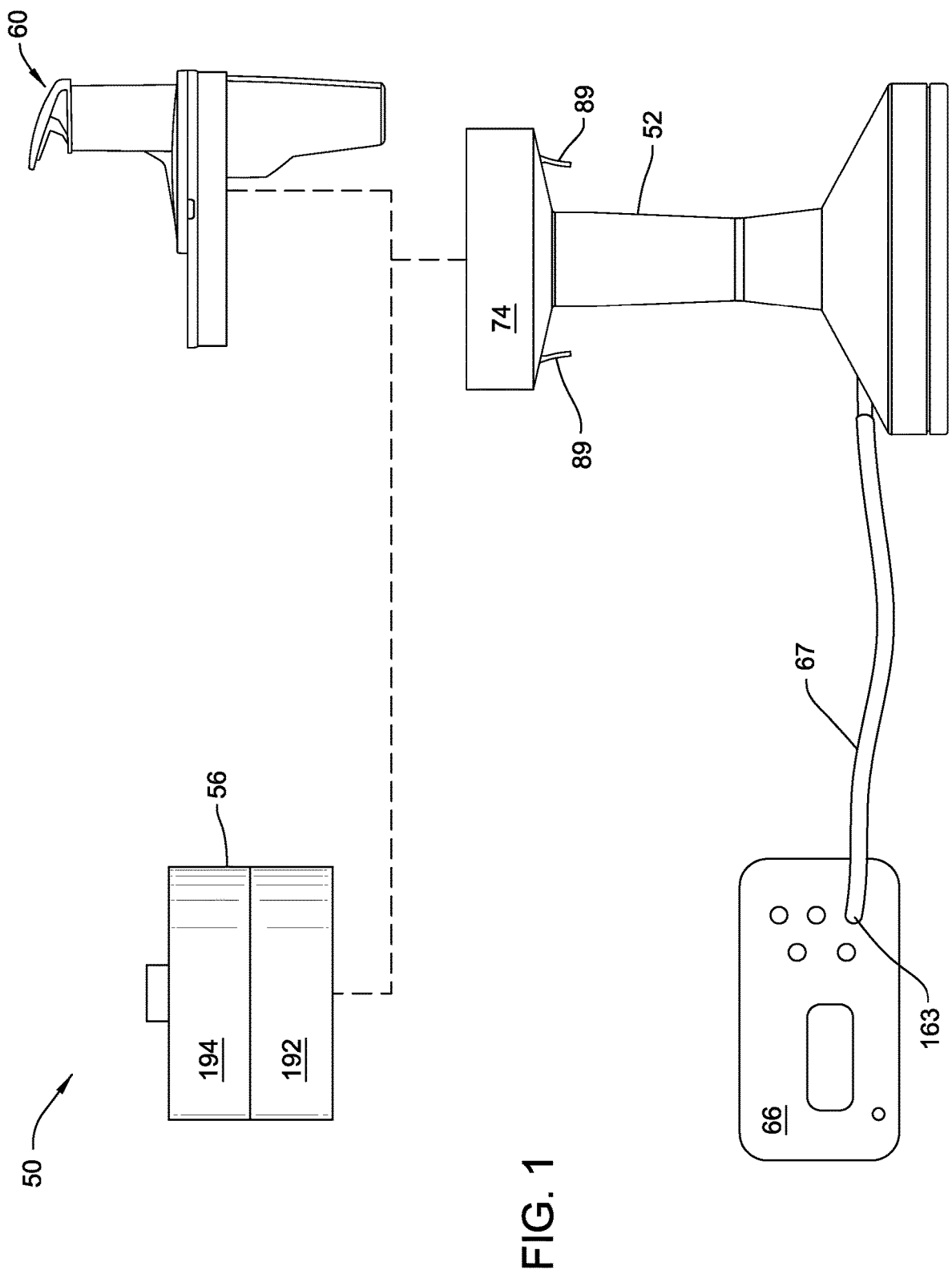
FIG. 1 depicts the basic components of the integrated system for cleaning and milling bone of this invention.
Figure 3:
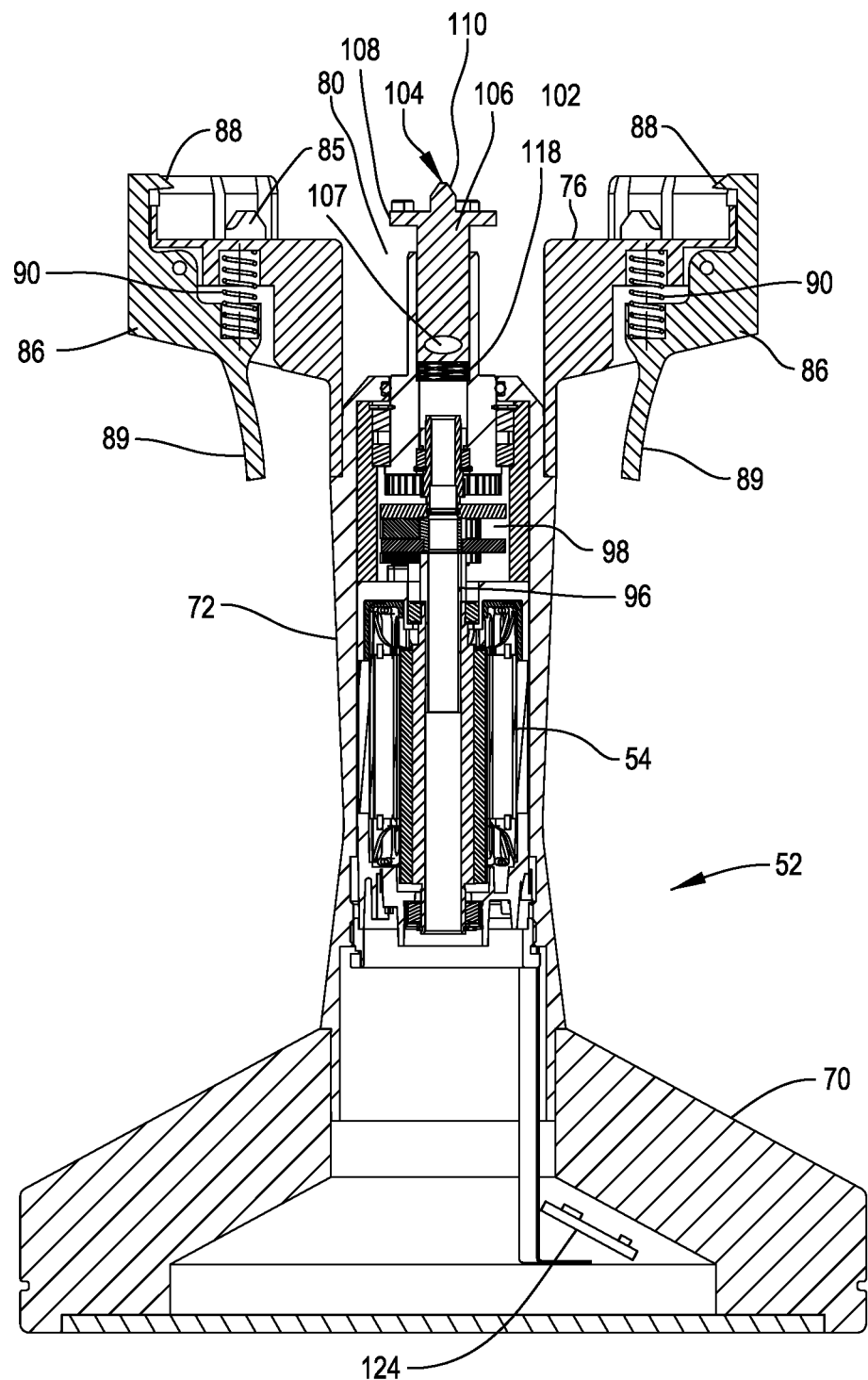
FIG. 3 is a cross sectional view of components internal to the base unit.
Figure 7:
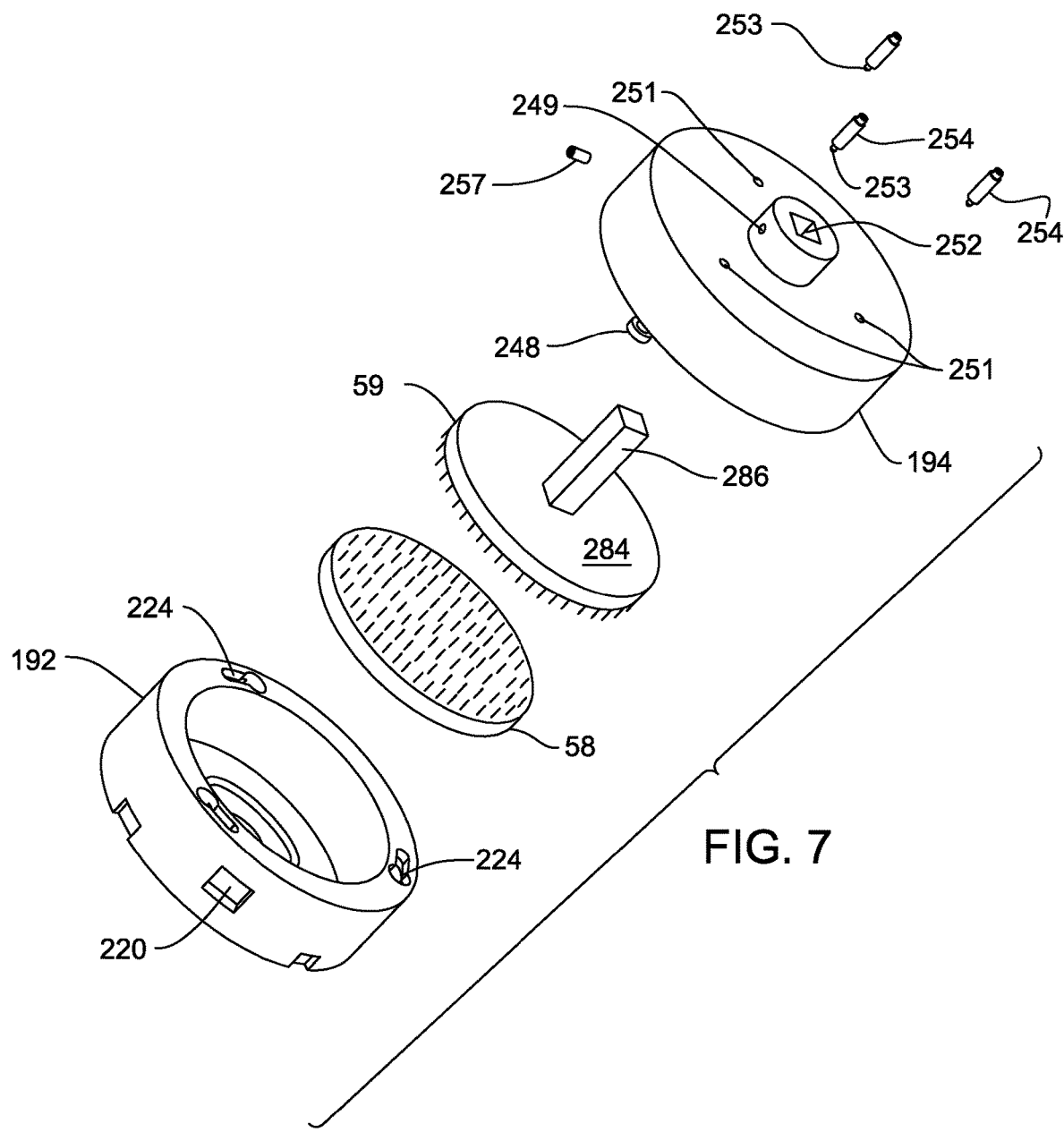
FIG. 7 is an exploded view of the components forming the cleaning head.

FIG. 1 illustrates the basic components of integrated system 50 of this invention for cleaning and milling bone stock. System 50 includes a base unit 52. Internal to the base unit 52 is a motor 54, (FIG. 3). A cleaning head 56 is removably attached to the base unit 52. Internal to the cleaning head are brushes 58 and 59 (FIG. 7). Cleaning head 56 is configured so that, when the cleaning head 56 is attached to the base unit 52, brush 58 is connected to the motor 54 so as to be actuated by the motor 54. The system 50 includes a mill head 60 that, like cleaning head 56, is configured to be removably attached to the base unit 52. A mill element 62 (FIG. 16), sometimes referred to as a cutting device, is moveably mounted inside, the mill head 60. Mill element 62 includes features that, when the mill head 60 is mounted to the base unit 52 couple the mill element to the motor 54.

Also part of system 50 is a control console 66. Control console 66 supplies the energization signals to the motor 54 that actuate the motor 54. Cable 67 connected between the base unit 52 and console 66 contains the conductors (not illustrated) over which energization signals are supplied from the console 66 to the motor 54.

System 50 of this invention is used by coupling the cleaning head 56 to the base 52. Harvested bone stock is placed in the cleaning head 56. The motor 54 is actuated so as to result in a like actuation of brush 58. The action of the brush 58 against the bone stock strips the soft tissue and other debris from the bone stock. The cleaning head 56 is removed from the base unit 52 and the mill head 60 is fitted to the base unit. The cleaned bone stock is placed in the mill head 60. Base unit motor 54 is again actuated so as to result in a like actuation of the mill element 62. As a consequence of the actuation of the mill element 62, the cleaned bone stock is milled into bone chips suitable for implantation into the patient.

II. Base Unit and Control Console

The base unit 52, now described by reference to FIGS. 2 and 3, includes a circular foot 70. A leg 72 having a circular cross section extends upwardly from foot 70. Leg 72 is tubular in shape. A pedestal 74 is disposed on top of leg 72. The pedestal 74 tapers outwardly from the leg 72. Pedestal 74 has a generally circular top surface 76. The pedestal is further formed to have a lip 78 that extends upwardly around the outer perimeter of the top surface. The outer circumference of lip 78, which is the outer circumference of the pedestal 74, is less than that of the circumference of foot 70 and larger than that of leg 72. Pedestal 74 is further formed so as to have an opening 80 in the center of top surface 76.

Figure 4:
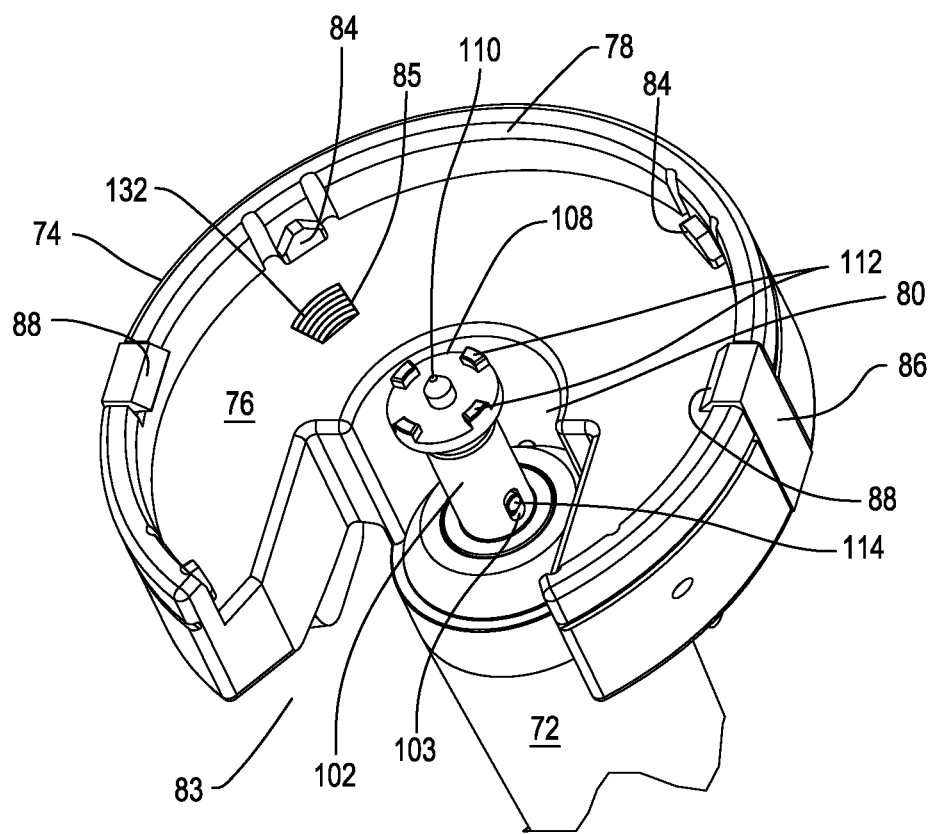
FIG. 4 is a perspective view of the top of the base unit.

While pedestal 74 is generally circular in shape, as best seen in FIG. 4, a notch 83 extends inwardly from the outer perimeter. Notch 83 thus forms a break in lip 78. In the illustrated version of the invention notch 83 extends to center opening 80. The pedestal is further formed to include a number of arcuately spaced apart teeth 84. Each tooth 84 extends upwardly from the outer perimeter of the pedestal top surface 76 adjacent lip 78. Pedestal 74 is further formed to have a rectangular opening 85 that is spaced away from both center opening 80 and notch 84.

Two retention arms 86, seen best in FIGS. 3 and 4, are pivotally mounted to the pedestal 74. Retention arms 86 are mounted to the pedestal in cutouts formed in the lip 78, (cutouts not identified). Each retention arm has a finger 88 that, when the arm is at rest, extends over a portion of the pedestal top surface 76. When the arms 86 are so positioned, the arms are in the "locked" state. Each retention arm 86 has a tab 89 located below the pedestal 74. By depressing the tab 89 inwardly, towards the underside of the pedestal 74, the arm 86 is pivoted outwardly so as to pivot the associated finger 88 away from its position over the pedestal top surface 76. When the arms 86 are so positioned, the arms can be considered in the "release" state. A spring 90 disposed between inner surface of the pedestal 74 and each arm 86, normally holds each arm in the locked state.

Referring to FIGS. 3 and 4, motor 54 includes a shaft 96 also disposed in the center hollow of leg 72. Shaft 96 extends upwardly toward pedestal center opening 80. A gear head at the top of shaft 96 (gear head not identified) engages a gear train 98 disposed in leg 72 above the motor 54. Gear train 98 steps down the rotational of speed of the rotational moment output by motor shaft 96. The gear assembly 98 has an output shaft 102 disposed in the pedestal center opening 80 below the top surface 76. Output shaft 102 is tubular in shape. Shaft 102 is formed to have two diametrically opposed oval openings 103 (one shown in FIG. 2) that extend longitudinally along the shaft.

In some versions of the invention, motor 54 and gear train 98 are collectively provided so that the gear train output shaft 102 can rotate at speeds between 100 and 500 RPM. These speeds are the under load speed when bone stock is disposed in either the cleaning head 56 or mill head 60. For reasons apparent below, the motor 54 and gear train 98 are designed to drive the output shaft 102 in an oscillatory pattern.

A drive spindle 104 is disposed in output shaft 102. The drive spindle 104 includes a stem 106. Above stem 106, spindle 104 is shaped to have a disc-shaped head 108. A number of different components extend upwardly from the top surface of the spindle head 108. One of these components is an alignment pin 110. The alignment pin 110 is coaxial with the longitudinal axis of the spindle 104 and extends upwardly from the center of the head 108. Pin 110 is shaped so that the lower portion, the portion that extends upwardly from the spindle head 108, has a cylindrical shape. The top portion of alignment pin has a shape of a cone with a flattened tip. (The individual sections of alignment pin 110 are not identified.)

Four equiangularly spaced apart alignment teeth 112 also extend upwardly from the top surface of the spindle head 108. Teeth 112 are located around the outer perimeter of the spindle head 108. The arcuate outer surfaces of teeth 112 are flush with the outer surface of the spindle head 108. Each tooth 112 has a pair of inwardly tapered side surfaces and an arcuate inner surface. (Surfaces not identified.) Teeth 112 do not extend as far above the spindle head 108 as does alignment pin 110.

Spindle 104 is dimensioned and positioned so that stem 106 is slidably mounted in the bore that extends through the gear assembly output shaft 102, (bore not identified). A pin 114 extends through a bore 107 in the spindle stem 106. The opposed ends of the pin 114 are seated in diametrically opposed openings 103 formed in shaft 102. Pin 114 holds the drive spindle 104 to the shaft 102 so that the spindle rotates in unison with the shaft and is able to move longitudinally relative to the gear assembly 98.

A spring 118 is disposed in the output shaft 102 below spindle stem 106. Spring 118 is a wave spring. One end of spring 118 is seated on the annular step internal to the output shaft 102 (step not identified). The opposed end of spring 118 is disposed against the bottom end of spindle stem 106. Spring 118 exerts an upward bias on spindle stem 106. This force, which can be overcome by the application of manual force, normally displaces the spindle 104 so that the head 108 is urged away from the pedestal top surface 76.

Figure 2:
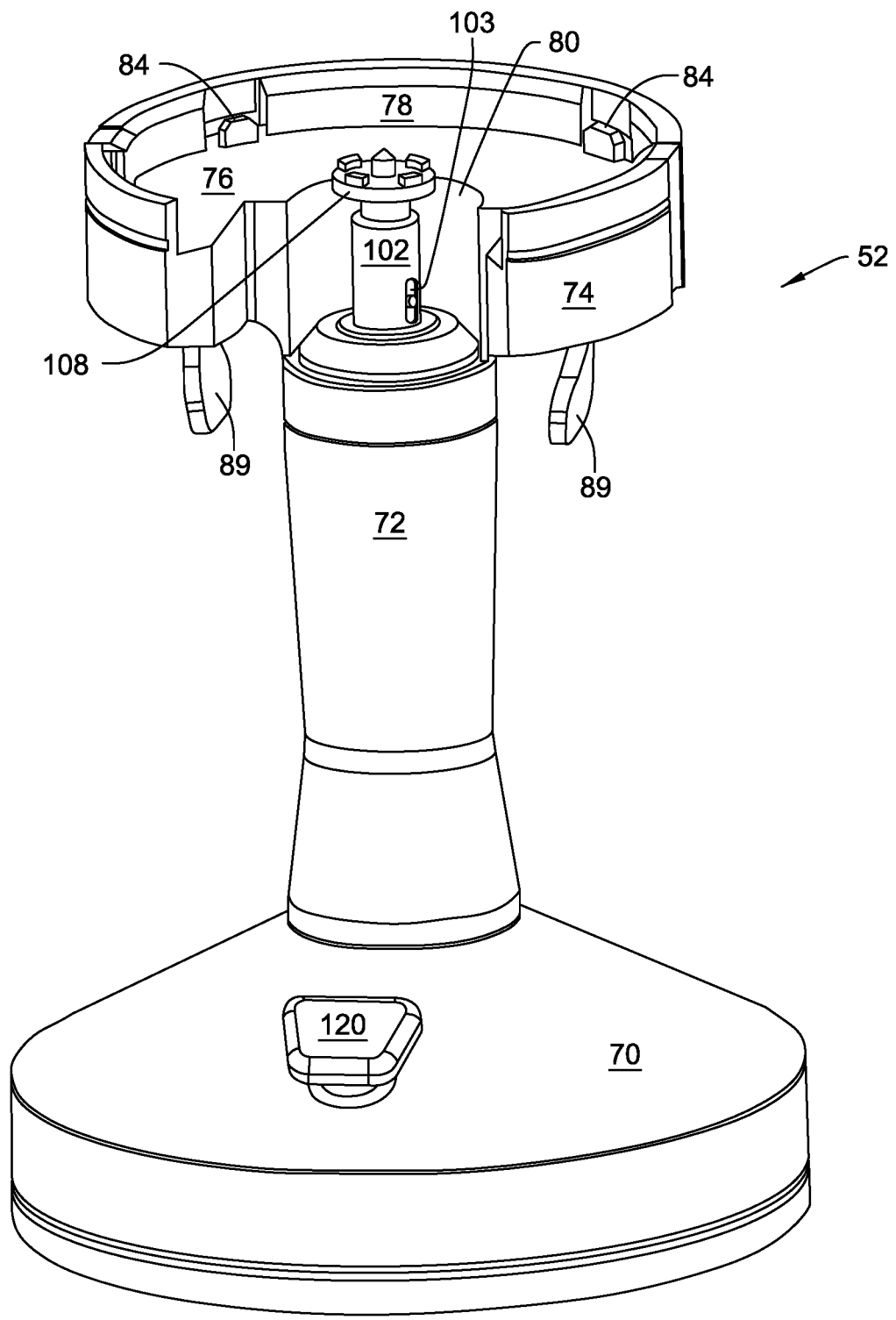
FIG. 2 is a perspective view of the base unit.

A spring biased, normal open press button switch 120 is mounted to the base unit foot 70 (FIG. 2). A socket 122, shown symbolically in FIG. 5, receives cable 67 from control console 66. Internal to foot 70 is a circuit board 124 (FIG. 3). Mounted to the circuit board 124 are components that function as the interface between switch 122 and the conductors that extend to socket 122. Also disposed on circuit board 124 are components that function as interfaces between the power conductors internal to cable 67 and the conductors that extend to the windings of the motor 54. The specific structure and configuration of these components as well as of the conductors that extend to motor 54, switch 120 and socket 122 are neither illustrated or part of this invention.

Figure 5:
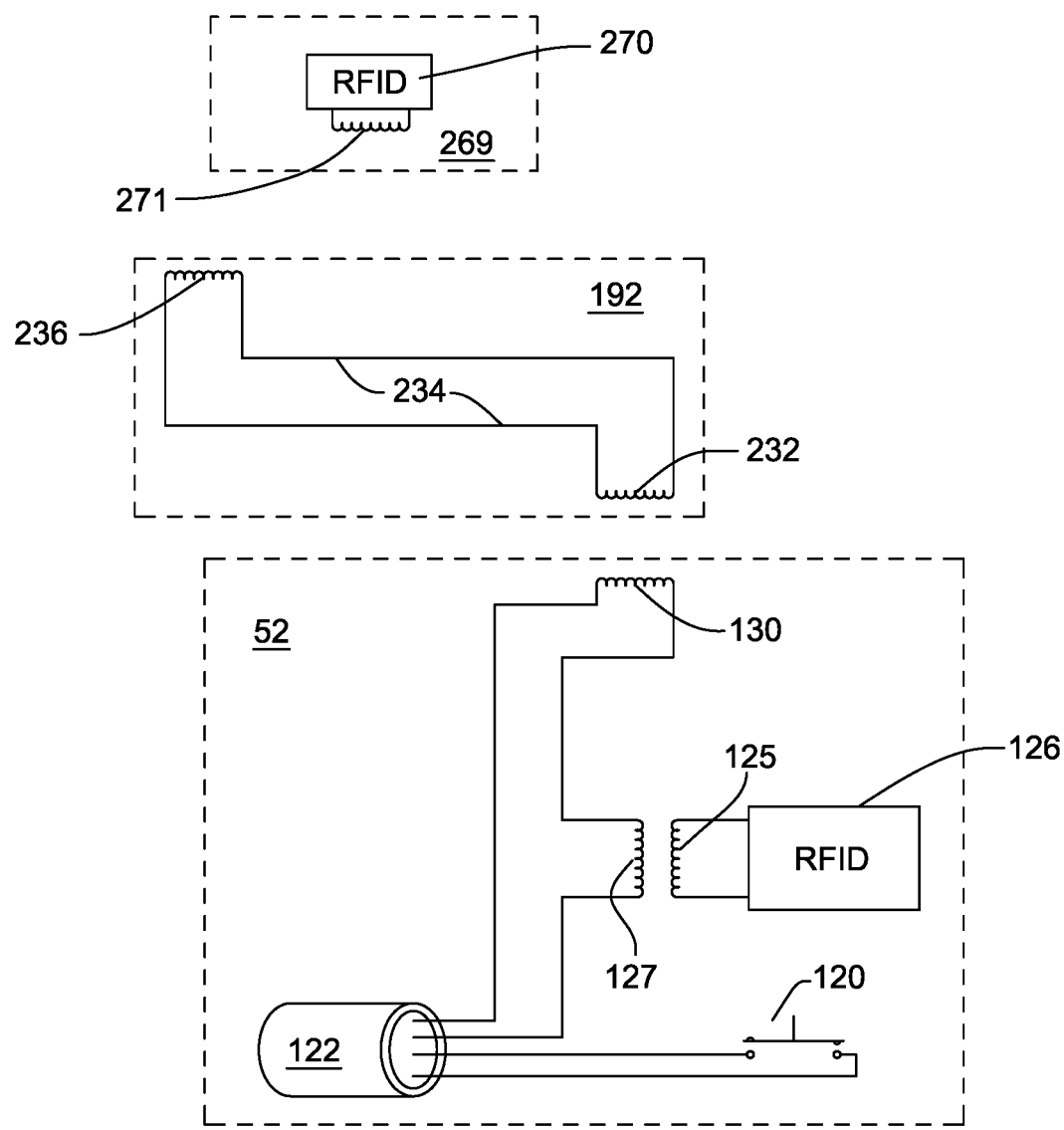
FIG. 5 is a schematic and block diagram of the memories internal to the base unit and cleaning head and the components over which data are read from and written to these memories.

Also disposed on circuit board 124 is a non-volatile memory 126 seen in FIG. 5. Memory 126 contains data describing the base unit 52. These data include data identifying the type of device; here, that the device is a bone cleaner/bone mill base unit. These data also contain data useful for supplying energization signals to the motor 54. These latter data include data indicating the speed range of the motor and the currents the motor should draw. A more complete list of the data that may be contained in memory 126 can be found in the Applicants' Assignee's U.S. Pat. No. 6,017,354, INTEGRATED SYSTEM FOR POWERED SURGICAL TOOLS, the contents of which is explicitly incorporated herein by reference. In one version of the invention, memory 126 is a radio frequency identification device (RFID) and is identified as such in FIG. 5. An antenna (coil) 125 is connected to the memory 126. A coil 127 is connected to the conductors 123 that extend from the socket 122. Signals between the control console 66 and the memory 126 are inductively exchanged between memory coil 125 and base unit coil 127.

Base unit 52 also includes an assembly for reading non volatile memories integral with the cleaning head 56 and mill head 60. This assembly includes a coil 130. Coil 130 is disposed in pedestal opening 85. Coil 130 is encased in a block 132 (FIG. 4) disposed in opening 85. Coil 130 is series connected to coil 127. Block 132 is formed from material permeable to RF energy and that can withstand the rigors of autoclave sterilization.

Figure 6:
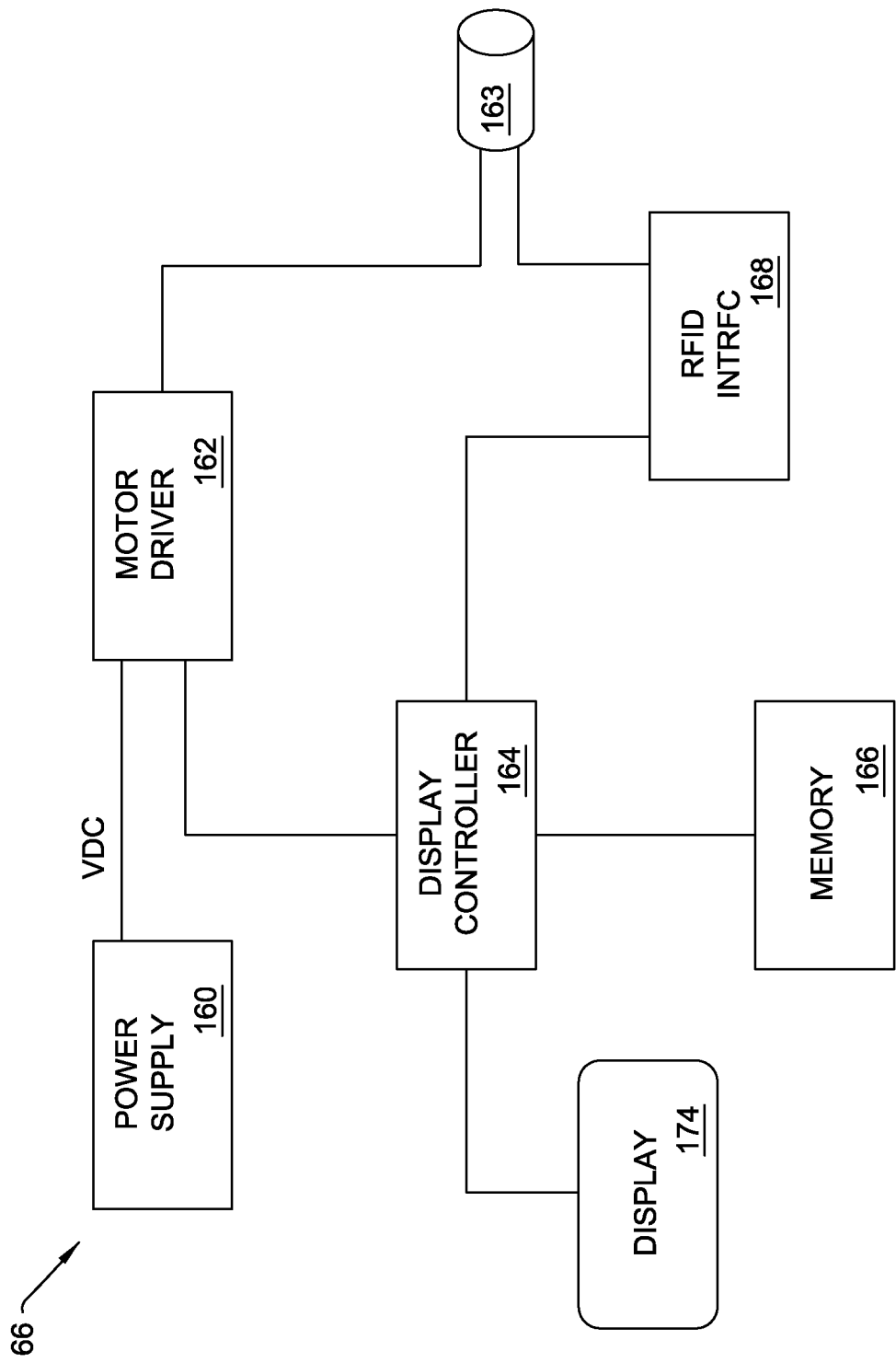
FIG. 6 is a simplified block diagram of the circuits internal to the control console.

FIG. 6 is a block diagram of some of the basic assemblies internal to the control console 66. One of these assemblies is the power supply 160. The power supply 160 converts the line signal into a DC voltage suitable for application to the windings internal to the base unit motor 54. Power supply 160 also produces AC and DC voltages by the other components internal to the control console and internal to the control console 66 and base unit 52. For reasons of simplicity, the only the connection shown out of the power supply 160 is the VDC that is applied to the motor windings. This VDC signal is applied to a motor driver 162. Motor driver 162 selectively ties the individual windings of the motor to either the VDC signal or ground. This is the commutation the current flowed through the motor windings (windings not illustrated). The motor driver 162 is connected to cable 67 by a socket 163 integral with the console 66.

Motor driver 162 selectively ties the motor windings to the VDC signal or ground based on both feedback signals from the windings and command signals from a display controller 164. The display controller 164 generates command signals that indicate the speed at which the motor should run, the maximum currents the windings should draw and the sequence in which the voltages are applied across the windings. These last data are used to regulate the direction in which the motor shaft rotates. Display controller 164 generates these command signals based on both user entered data and stored data that indicates the characteristics of the energization signals that are to be applied to the motor.

The data indicating the characteristics of the energization signals that are to be applied to the base unit motor 54 are retrieved from different sources. These data may be stored in memory 166 internal to the control console 66. These data may be retrieved from the memory 126 internal to the base unit 52. Alternatively, these data may be retrieved from a memory 270 internal to the cleaning head 56 (FIG. 5) or a memory 320 (FIG. 17) internal to the mill head 60.

To read the data in the base unit memory 126, cleaning head memory 270 and mill head memory 320 control console 66 includes a RFID interface 168. RFID interface 168 is connected to the display controller 164. In response to command signals from the display controller 164, the RFID interface sends read request signals to the complementary memories. In response the read request, the memory 126, 270 or 320 writes out the stored data. Interface 168 converts these data signals into digital signals that are interpreted by the display controller 164.

Control console 66 also includes a touch screen display 174. Display controller 164 generates both data images and images of command buttons for presentation on the display 174. The display controller 164 receives the signals when an individual presses the display buttons. In response to the depression of the buttons, display controller 164 generates the appropriate commands to cause the user-requested operation of the base unit motor 54.

A more detailed understanding of the structure of the control console 66 can be found in the Applicants' Assignee's U.S. Pat. No. 7,422,582, CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAN ALL OF THE HANDPIECES, the contents of which are explicitly incorporated herein by reference.

III. Cleaning Head

As seen by reference to FIG. 7, the cleaning head includes opposed lower and upper shells 192 and 194, respectively, that are releasably coupled together. A lower brush 58 is rotatably and removably disposed in the lower shell 192. An upper brush 59 is disposed in the upper shell 194. While the upper brush 59 is removably and, to a limited degree moveably mounted with regard to the upper shell, the upper brush does not rotate. A cap, (not illustrated) may be removably fitted over the exposed top of upper shell 194.

Figure 10:
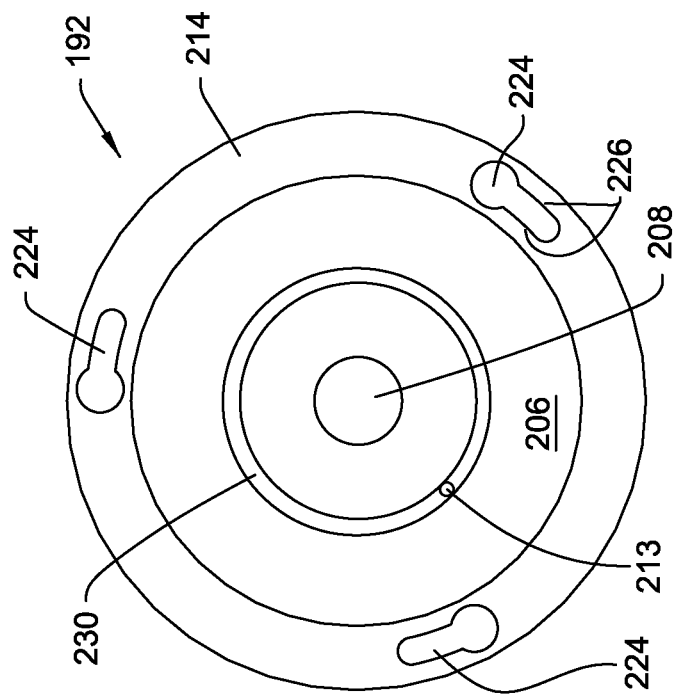
FIG. 10 is a plan view, looking down, of the cleaning head lower shell.
Figure 9:
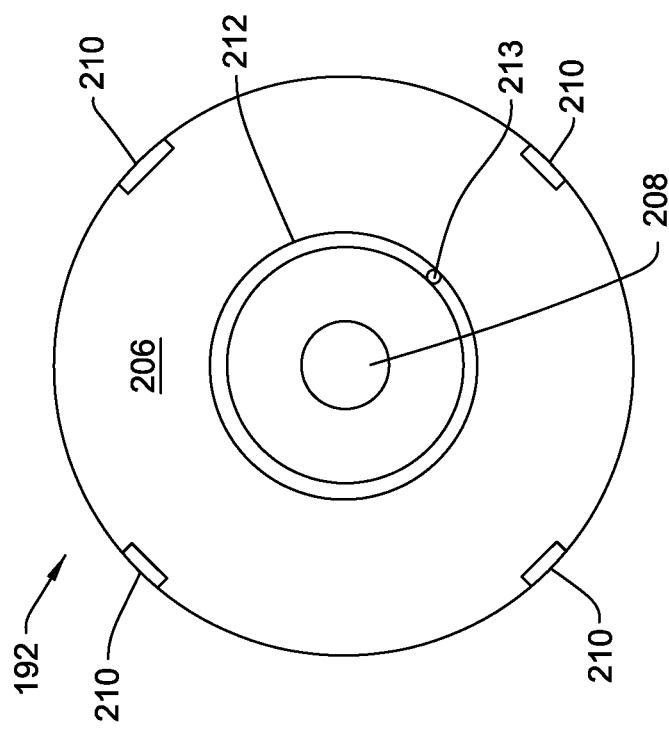
FIG. 9 is a view of the bottom surface of the lower shell of the cleaning head.

Lower shell 192 is formed from aluminum or other material that can withstand repetitive autoclave sterilization. As seen best in FIGS. 8, 9 and 10, the lower shell is shaped to have a disc shaped base 206. Base 206 has an outer diameter that allows the shell 192 to be slip fitted in the void space immediately above pedestal top surface 76 within lip 78. Shell base 206 has a center opening 208. Center opening 208 has a diameter that is approximately 2 mm larger than the diameter of spindle head 108. Four equiangularly spaced apart notches 210 extend inwardly and upwardly from the downwardly directed face of the shell base. Notches 210 are dimensioned so that when the cleaning head 56 is fitted to base unit 52, pedestal teeth 84 are able to seat in the notches.

Located radially outwardly from opening 208, base 206 is formed to have an annularly extending groove 212. Groove 212 is positioned so that, when the cleaning head 56 is seated in the pedestal void space 79, groove 212 extends over the space above coil 130. A hole 213 extends upwardly from the base of groove 212.

A ring 214 is integrally formed with and extends upwardly from the outer perimeter of shell base 206. The outer diameter of ring 214 is coincident with the outer diameter of base 206. Ring 214 defines a cylindrical void space (not identified) within the lower shell 192. The outwardly directed face of the shell base 206 functions as the base of this void space. Lower shell 192 is further formed to have two additional notches 220 that are diametrically opposed from each other. (Only one notch 220 seen in FIG. 8.) Notches 220 extend inwardly from the outer cylindrical surface of the shell 192 at a location above the bottom of the shell. More particularly, shell 192 is formed so that when the shell is seated in pedestal void space 79 and teeth 84 are in notches 210, notches 220 are positioned so the fingers 88 integral with the pedestal retention arms 86 can seat against the shell ring surfaces that define the bases of the notches 220.

Lower shell 192 is further formed to have three equiangularly spaced apart slots 224 in the exposed circular, outwardly directed face of ring 214. Each slot 224 has what can be generally described as a keyhole shape. That is, each slot 224 has a circular section and a section that resembles a section of a curve that extends away from the circular section (individual sections not identified). The width across each curved segment section is less than the diameter of the circular section. More particularly, lower shell 192 is formed so that opposed ledges 226 extend over the slot curved sections to provide the appearance of these sections having a width less than diameter of the slot circular sections. Below the ledges 226 the common widths of slots is constant.

Shell base 206 is further formed to have a circular groove 230 in the outwardly directed face of the base. Hole 213 opens into the surface of the base 206 that forms the base of the groove 230.

A coil 232, seen in FIG. 5, is disposed in base groove 212. Not seen is the ring formed of PEEK, polyetherimide or other sterilizable plastic in which coil 232 is embedded. Accordingly, both the coil 232 and the ring are seated in groove 212 so as to be flush with the downwardly directed face of shell base 206. Conductors 234 extend from coil 232 through shell base hole 213. Conductors 234 extend to a coil 236 seated in shell base groove 230. Coil 236 is embedded in the same type of ring (not illustrated) in which coil 232 is embedded. Coil 236 and its complementary ring are seated in groove 230 so as to be flush with the adjacent outwardly directed face of shell base 206.

Figure 11:
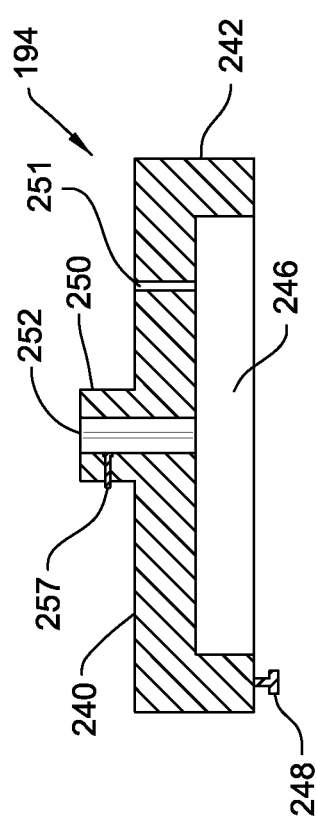
FIG. 11 is a cross sectional view of the cleaning head upper shell.

The cleaning head upper shell 194, now described by reference to FIGS. 7 and 11, is formed from the same material from which lower shell 192 is formed. Upper shell 194 includes a circular plate 240. Plate 240 has the same outer diameter of the lower shell 192 and functions as the superstructure of the upper shell 194. An annular skirt 242 formed integrally with the plate 240, extends downwardly from the outer perimeter of the plate. The bottom surface of plate 240 and skirt 242 thus define a void space 246 internal to the upper shell 194 that extends upwardly from the outer face of the skirt to the downwardly directed surface of plate 240.

Three equiangularly spaced apart pins 248 extend downwardly from the downwardly directed face of skirt 242 (Only one pin 248 seen in both FIGS. 7 and 11.) Each pin 248 has a narrow diameter stem (not identified) and a large diameter head (not identified). The pin heads are dimensioned to pass through large diameter opening of one the lower shell slots 224 but not the narrow diameter curved section of the slot. Upper shell pins 248 are thus the fastening members that complement the lower shell slots 224 so as to removably hold the shells 192 and 194 together without the aid of other fastening components. A cylindrical boss 250 formed integrally with the plate 240 extends upwardly from the exposed upper surface of the plate. Boss 250 is centered on the longitudinal axis of the plate 240. A bore 252 extends through the plate 240 and overlying boss 250. Bore 252 is centered on the longitudinal axis of the plate 240 and boss 250. Bore 252 has a non-circular cross sectional shape. In the illustrated version of the invention, the bore 252 has a cross-sectional shape that is square. A threaded bore 249 extends laterally from the side of boss 250 into bore 252.

Three load pins 253 are slidably mounted in through holes 251 formed in plate 240. Holes 251 are equiangularly spaced apart from each other and located outwardly of shell boss 250. Each pin 254 extends into void space 246. A helical spring 254 is disposed around the section pin 253 disposed in the shell void space 246. Springs 254 urge the pins 253 toward the lower shell 192. Not seen are the heads of the pins against which the springs 254 abut and the feet of the pins that prevent the pins from falling out of the holes 251.

FIGS. 12 and 13 illustrate the features of the cleaning head lower brush 58. Brush 58 is formed to have disc-shaped substrate 260 formed of metal or a sterilizable plastic such as a glass-filled nylon. Substrate 260 has an outer diameter that is generally at least 0.5 mm less than the diameter of the void space defined by the inner wall of lower shell ring 214. Thus brush 58 is able to float, laterally shift position, within the lower shell 192. While the opposed upper and lower faces of substrate 260 are generally planer and parallel, a number of indentations extend upwardly from the inner face lower face of substrate 260. One of these indentations is a closed-end bore 262 that is centered over the longitudinal axis of the disc. Bore 262 has a diameter that allows the base unit drive spindle alignment pin 110 to seat therein. Four equiangularly spaced apart notches 264 are the other indentations that extend upwardly from the bottom-directed face of lower brush substrate 260. Notches 264 are positioned so that when spindle pin 110 is seated in substrate bore 262, spindle teeth 112 seat in the notches. Substrate 260 is also formed to have a single notch 266. Notch 266 is positioned so that when lower brush 58 is seated in the lower shell 192, the notch 266 is disposed over coil 236.

Lower brush 58 includes a number of bristles 268 that extend upwardly from the upwardly directed face of substrate 260. The bristles 268 are formed from a stainless steel. Bristles 268 are attached to substrate by an adhesive 267 such as an epoxy adhesive. In manufacture, adhesive 267 is initially applied over upwardly directed face of substrate 260. Before the adhesive cures, the bristles 268 are planted in the adhesive 267.

An RFID chip 270, illustrated in FIG. 5, is disposed in substrate notch 266. RFID chip 270 functions as the memory for the lower brush 194. Attached to RFID chip 270 is a coil 271. RFID chip 270 and coil 271 are encapsulated in a plastic block 269 (shown in phantom in FIG. 5). Block 269 is formed from a plastic that allows inductive signal exchanged between shell coil 236 and brush coil 271.

Figure 14:
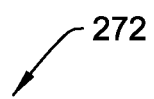
FIG. 14 depicts data fields in the memory of the RFID fitted to the cleaning head lower brush substrate.

FIG. 14 illustrates different data stored in the actual memory 272 internal to the RFID chip 270. The data in memory 272 include a device identification field 273. The data in field 273 identifies that the associated device is a bone cleaning brush. If there are a number of different bone cleaning brushes, the data in field 273 identifies the specific kind of brush. A use field 274 contains data indicating whether or not the brush is useable. It is anticipated that, owing to the expenses associated with post-use sterilization, each brush is a use once brush. Accordingly, field 274 may be a single bit field that is initially set to contain data indicating that the brush 58 can be used.

Memory 272 also contains minimum, default and maximum motor speeds fields 275, 276 and 277, respectively. The data in the minimum and maximum motor speed fields 275 and 277, respectively, indicate, respectively, the preferred minimum and maximum speeds at which the base unit motor 54 should be driven to rotate the lower brush 58. The default speed field 276 indicates that speed at which the motor is to be driven in the event the personnel operating the system do not set any other speed.

A direction field 278 indicates the direction in which base unit motor 54 should be driven. Typically, the data in field 278 indicates if the motor is to be driven in a single direction or in an oscillatory mode. If the motor, actually, the lower brush 58, is to be driven in a single direction the direction of rotation is irrelevant. If the lower brush 58 is to be oscillated back and forth, field 278 may include additional data indication through which how many degrees the brush should rotate before the direction of rotation is reversed.

In some versions of the invention, field 278 may contain data indicating a sequence of rotation in which the lower brush 58 upon actuation. One sequence may include an initial rotation of the brush through 10 rotations in one direction followed by rotation in oscillatory pattern wherein in each phase of the oscillation the brush rotates 2 rotations (720°) in one direction before the direction of rotation is reversed.

Figure 15:
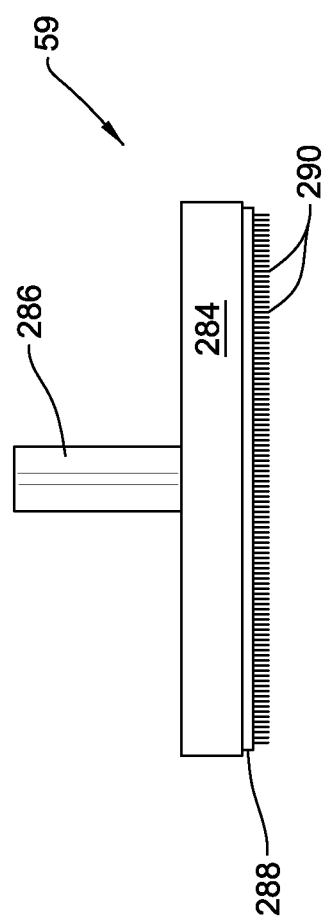
FIG. 15 is a side view of the cleaning head upper brush.

The upper brush 59, now described with reference to FIG. 15, includes a disc shaped superstrate 284. Superstrate 284 is formed from the same material from which lower brush substrate 260 is formed. The superstate 284 has an outer diameter equal to the lower brush substrate 260. A post 286 extends upwardly from the longitudinal center axis of superstrate 284. Post 286 is dimensioned to slidably fit in upper shell bore 252.

Bristles 290 extend downwardly from the bottom facing surface of superstrate 284. A layer of adhesive 288 holds the bristles 290 to superstrate 284.

A ball plunger 257 (FIG. 7) is fitted in upper shell bore 249. Ball plunger 257 is set to press against post 286 to prevent upper brush 59 from falling out of upper shell 194. In some versions of the invention, brush post 286 is formed with a detent (not illustrated) for receiving the plunger head.

IV. Mill Head

Figure 16:
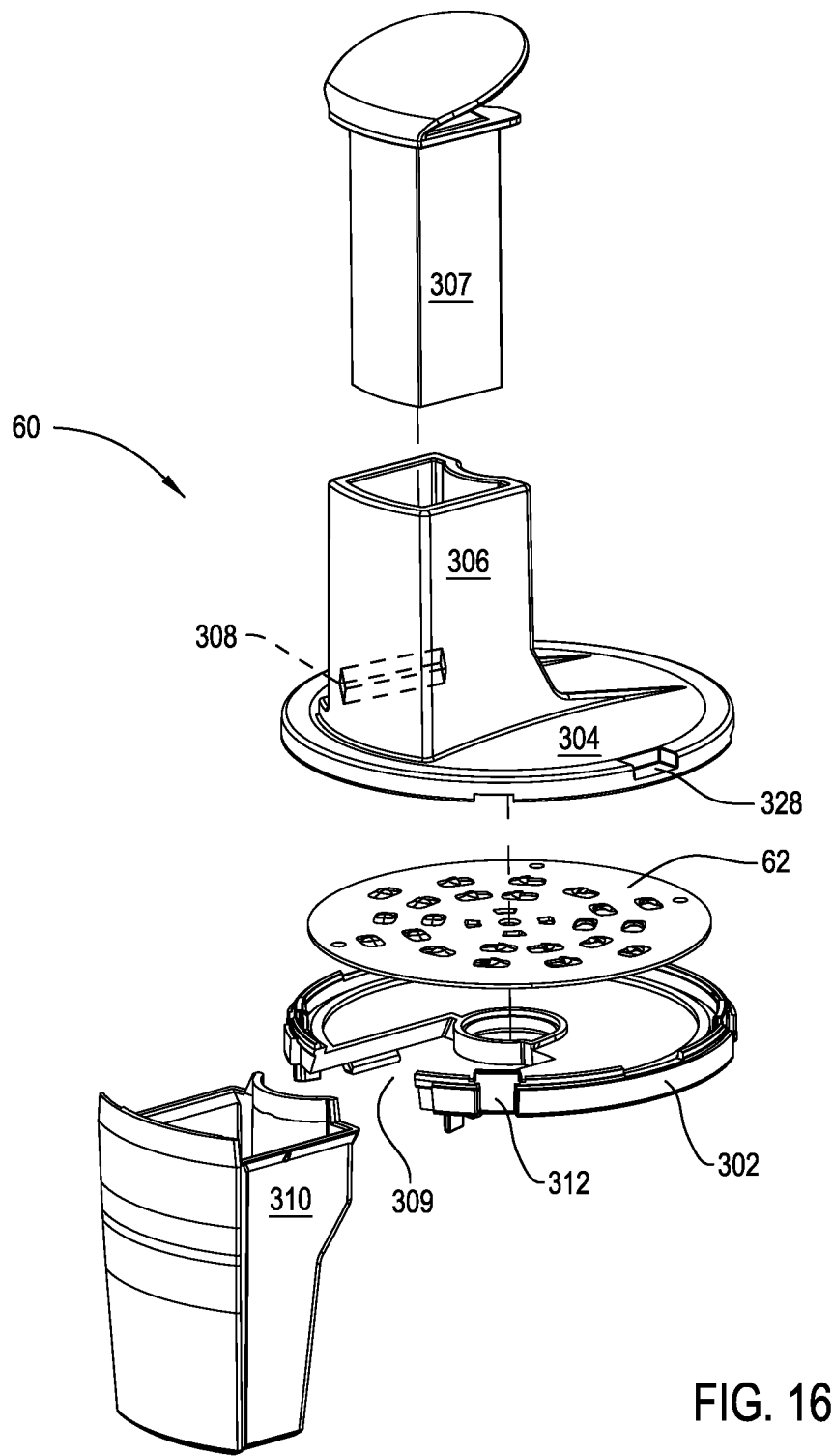
FIG. 16 is an exploded view of the system mill head.

FIG. 16 illustrates the basic components of the mill head 60. There are bottom and top shells 302 and 304, respectively. When assembled together, shells 302 and 304 form the housing of the mill head 60. Mill element 62 is a disc shaped member sandwiched between shells 302 and 304. Top shell 304 is formed to have an open ended feed sleeve 306. The center space defined by sleeve 306 opens into the space in which mill element 62 is seated. A plunger 308 is slidably fitted in feed sleeve 306.

Fitted to top shell 304 is an impingement plate 308 (shown in phantom as a rectangular bar). Impingement plate 308 is mounted to the top shell so as to be near the base of the feed sleeve and immediately above the mill element 62.

Bottom shell 302 is formed to have an opening 309 immediately bellow the feed sleeve 306. A removably catch tray 310 is slidably fitted to the bottom shell 302. Catch tray 310 is fitted to bottom sleeve 306 to receive bone chips discharged from mill head 60 through opening 309.

Figure 17:
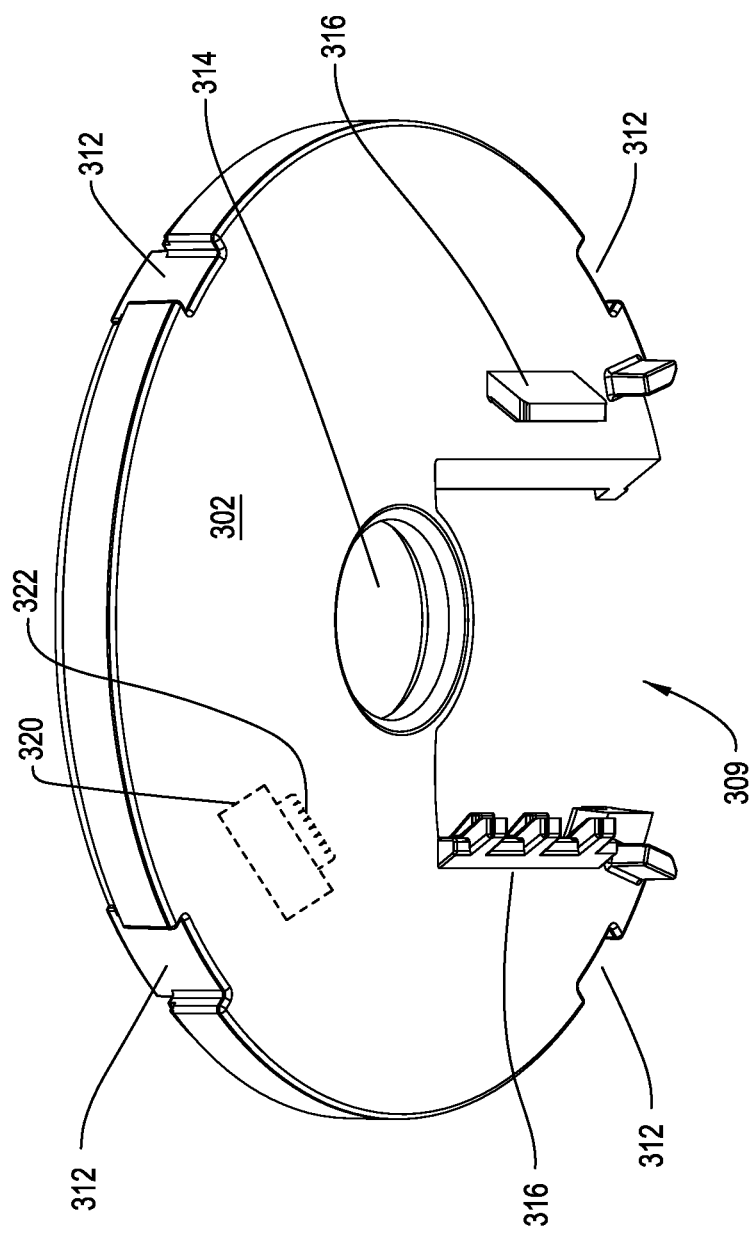
FIG. 17 is a perspective view of the bottom shell of the mill head.

Mill head bottom shell 302, seen in FIG. 17, is generally circularly shaped. More particularly, shell 302 is dimensioned to seat within the base unit void space 79. Shell 302 is formed to have four equiangularly spaced apart notches 312 that extend inwardly from the outer perimeter of the shell. Notches 312 are positioned so that when mill head 60 is seated on the base unit pedestal 74, pedestal teeth 84 seat in the notches 312. Shell 302 has a center located opening 314 dimensioned to receive base unit drive spindle 104.

Opening 309 extends inwardly from the perimeter of the bottom shell 302. The bottom shell 302 is further formed to have two rails 316 located on the opposed sides of opening 309. Rails 316 are dimensioned to allow the catch tray to be slidably held to the shell 302 below opening 309. For reasons not relevant to the present invention, the rails 316 are shaped differently from each other.

An RFID chip 320, shown as a phantom rectangle in FIG. 17, is embedded in bottom shell 302. A complementary coil 322, also shown in phantom is attached to RFID chip 320 and also embedded in shell 320. Coil 322 is located within the shell 302 so that when the mill head 60 is disposed on the base unit 52, the coil 322 is disposed over base unit coil 130. The memory of RFID 320 contains data similar to that contained in cleaning head RFID 270. Specifically, there is a data field in which data identifying the type of device, a mill head 56, are stored. There is also at least one data field indicating the speed at which the base unit motor 54 should operate when the mill head 56 is attached. Typically, the mill element 62 is intended to be driven at a single speed. Accordingly, in a number of versions of the invention, RFID 320 only contains a single data field containing data indicating the speed at which mill element 62 is to be rotated. Also, the mill element 62 is typically only rotated in a single direction. Accordingly, RFID 320 likewise typically does not contain any data containing instructions regarding a forward/reverence sequence for driving the mill element 62.

Returning to FIG. 16, it can be seen that top shell 304, like bottom shell 302 is generally disc shaped. The top shell 304 is further shaped to have the same outer diameter as the bottom shell 302. Collectively, shells 302 and 304 are shaped so that when the mill head 60 is seated in base unit void space, the outer face of the top shell 304 is slightly above the pedestal lip 78. The top shell 304 is formed so as to have two diametrically opposed notches 328; one notch seen in FIG. 16. Notches 328 are positioned so that when the mill head 60 is fitted to the base unit pedestal 74, the base unit retention arm fingers 88 are able to seat in the notches 328.

Figure 18:
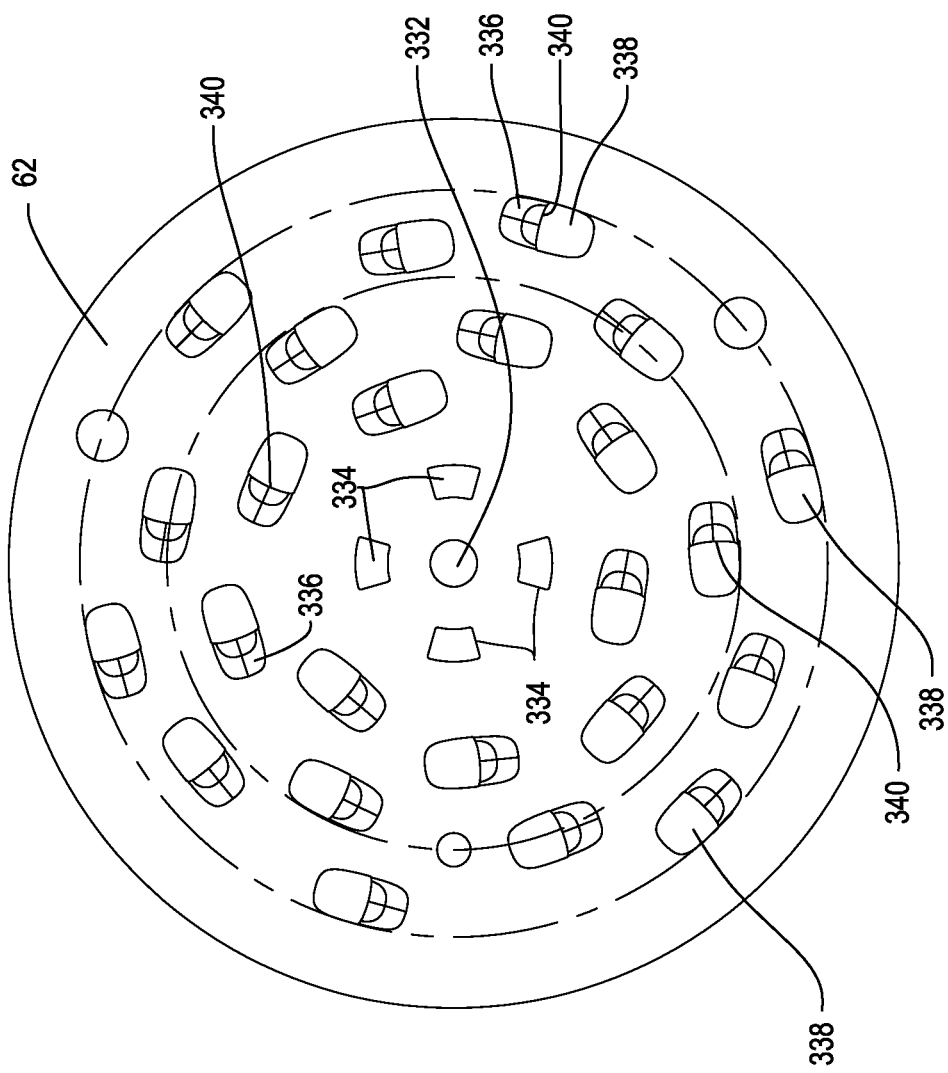
FIG. 18 is a plan view of the mill element, here a cutting disc, internal to the mill head.

Mill element 62, seen best in FIG. 18, may be formed from metal such as 410 Stainless Steel. In the illustrated version of the invention, the mill element 62 is generally in the form of a planar disc. In the illustrated version of the invention, mill element 62 is sometimes referred to as a cutting disc. Collectively, the components forming the mill head 60 are dimensioned so that the mill element 62 can engage in lateral movement, as well as some up-and-down movement, within the mill head housing.

The mill element 62 is further shaped to have a center-located hole 332. Hole 332 is dimensioned to receive the alignment pin 110 integral with the base unit drive spindle 104. Located around hole 332, mill element 62 is formed to have four equiangularly shaped apart openings 334. Each opening 334 is shaped to receive a separate one of the teeth 112 integral with spindle 104. Accordingly, openings 334 are arcuately shaped. The circle defined by the outer circumference of openings 334 is less than bottom shell opening 314.

The mill element 62 is further formed to have a number of cutting scallops 336. Integral with and longitundally axially aligned with each cutting scallop 336, the cutting disc has a through opening 338. More particularly, the mill element 62 is formed so that each cutting scallop 336 extends above the adjacent top surface of the element. The scallops 336 are milled to define a cutting edge 340 that forms a perimeter of the adjacent opening 338.

Impingement plate 308 is formed from material against which bone stock can be pressed without causing the fracture of the plate. In some versions of the invention, this material is 304 stainless steel. The impingement plate 308 is fitted to the mill head top shell 304 so as to be located to one side of the opening through feed sleeve 306 and so as to be above the mill element 62. Impingement plate 308 is further positioned so that, as the mill element 62 rotates, first an element opening 338 followed by the cutting edge-defining scallop 336 that defines the opening rotates towards and under the plate 308.

V. Operation

System 50 of this invention is used to clean and mill bone that is harvested to serve as stock from which bone chips are formed. To prepare the system for use, a lower brush 58 is fitted in lower shell 192 and an upper brush 59 is fitted in upper shell 194. The harvested bone is placed against the lower shell bristles 268. The upper shell 194 is coupled to the lower shell so that that harvested bone stock is sandwiched between the lower and upper brushes 58 and 59, respectively. To couple the shells 192 and 194 together, the upper shell pins 248 are rotating held in the lower shell slots 224. Collectively, these steps are called out as step 350 in FIG. 19A.

Once the two shells 192 and 194 are coupled together, the post 286 may be pressed downwardly to unlock the post from the ball plunger 257. This allows upper brush 59 to move longitudinally within cleaning head 56. Pins 253, which are urged against the upper brush superstrate 284 by springs 254, provide a force in addition to gravity that presses the upper brush bristles 290 against the bone to be cleaned. It should be understood that owing to the relative dimensions of the lower shell 192 and brush 58, the brush may shift laterally within the shell.

The cleaning head 56 is then mounted to base unit 52, step 351. More particularly, the cleaning head 56 is positioned so that the head lower shell 192 is positioned on pedestal top surface 76 so that pedestal teeth 84 seat in shell notches 210. Base unit retention arms 86 are set so that fingers 88 seat in pedestal notches 220. This seating of the retention arm fingers 88 in the lower shell notches 220 is what holds cleaning head 56 to the base unit 52. The seating of base unit teeth 84 in cleaning head notches 210 prevent rotation of the head 56 relative to the base unit 52.

As part of the seating of the cleaning head 56 on the base unit 52, step 351, drive spindle 108 extends through the lower shell opening 208. The spindle alignment pin 110 seats in lower brush opening 262. The seating of pin 110 in opening 262 may laterally shift the lower brush 58 in the lower shell 192 so that substrate openings 264 define a circle that is aligned over spindle drive teeth 112.

Also as part of preparing the system 50 for use, the base unit 52 is connected by a cable 67 to control console 66. The control console 66 is actuated. (Steps not illustrated.)

Figure 19A:
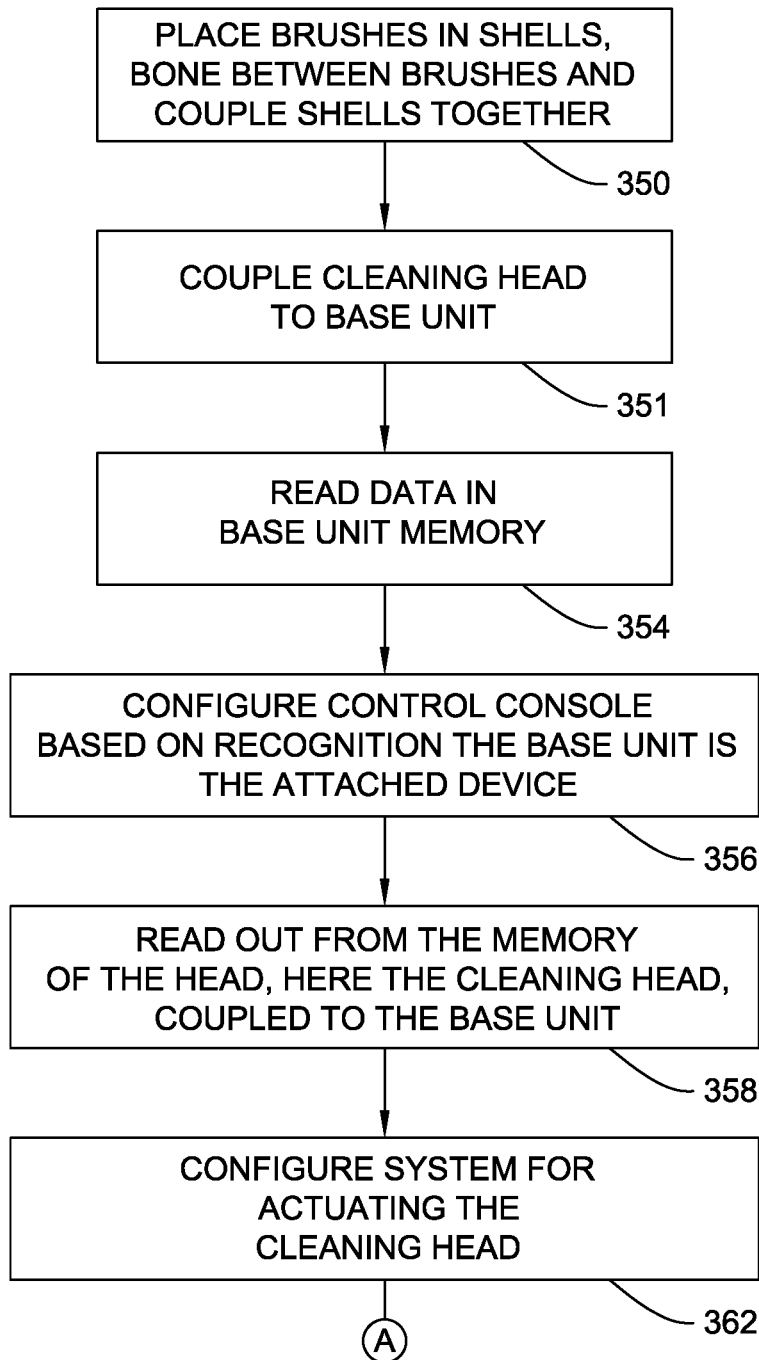
FIGS. 19A through 19C, when assembled together, form a flow chart of the steps performed to both clean bone stock and convert the bone stock into chips using the system of this invention.

Once the system is actuated, the control console display controller 164, through RFID interface 168, reads the contents of the base unit memory 126, step 354 of FIG. 19A. Base on unit-identifying data in memory 126, in step 324, display controller 164 determines that the device attached to control console 66 is a bone cleaner/bone mill base unit 52, step 356. Based on this determination, display controller 164, as part of step 356, recognizes that it must determine the type of head 56 or 60 attached to the base unit before it determines the characteristics of the energization currents that should be applied to the base unit motor 54. Accordingly, in a step 358 the display controller 164, through the RFID interface 168, reads out the data in the cleaning head brush RFID 270, step 360. These data are read as a consequence of the inductive signal exchange between base unit coil 130, shell coils 232 and 236 and brush coil 271.

It should be understood that there is always the possibility that either cleaning head 56 or mill head 60 once attached to the base unit 52 will be removed. Therefore, periodically throughout the time the base unit 52 is attached to the control console 66, the display controller 164 will request the RFID interface to conduct a basic interrogation to determine if the head 56 or 60 previously attached to the base unit 52 is still attached. This integration process often involves the outputting of a by the RFID interface 168 of a request that any attached RFID write back some basic identifying data. These data, if written back to the display controller 164 indicate that the device that was attached to the base unit 52 is still attached. Thus, as long as the base unit is connected to the console 66, data are written from the base unit memory 126 back to the console. The same read out of data occurs as long as the mill head 56 is attached to the base unit 52.

Figure 19B:
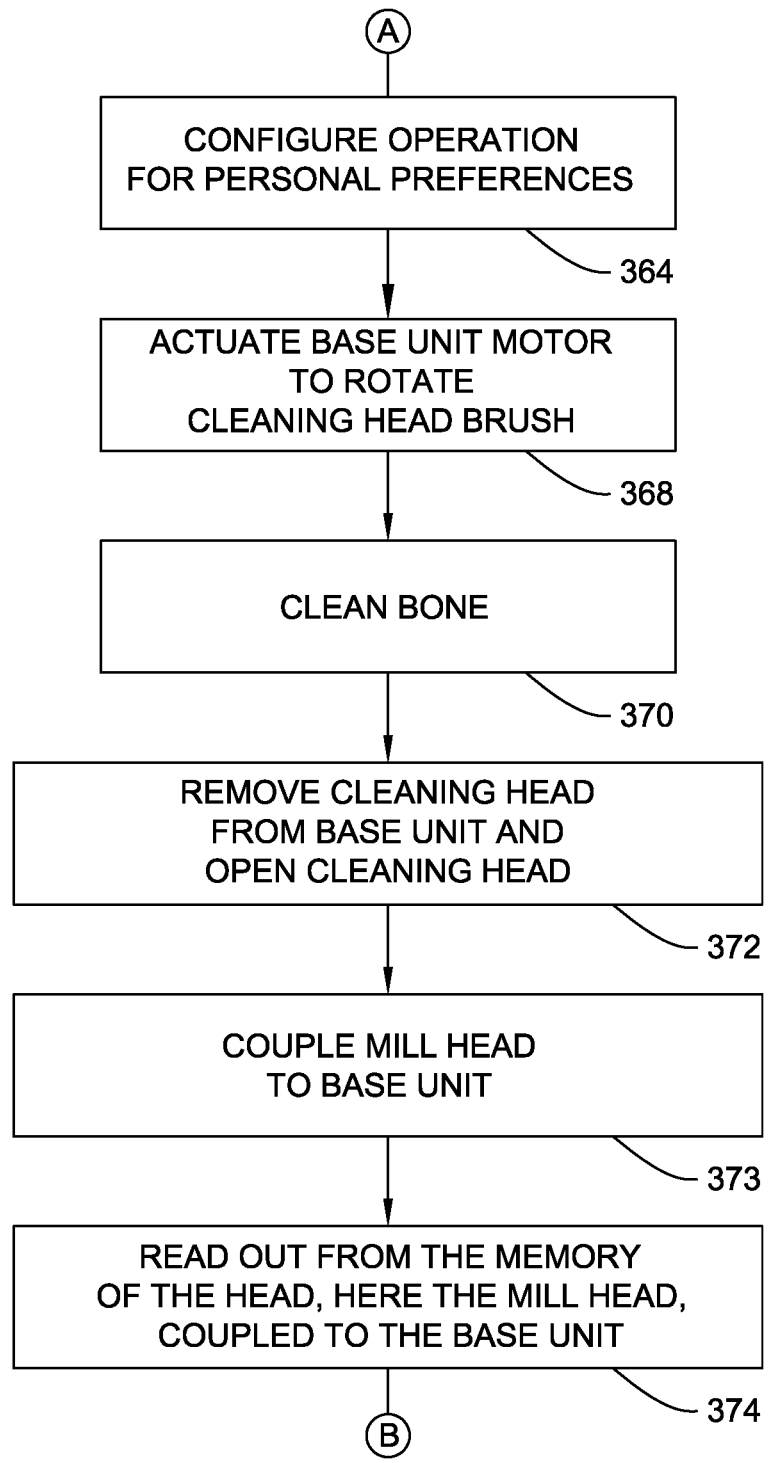
Figure 19C:
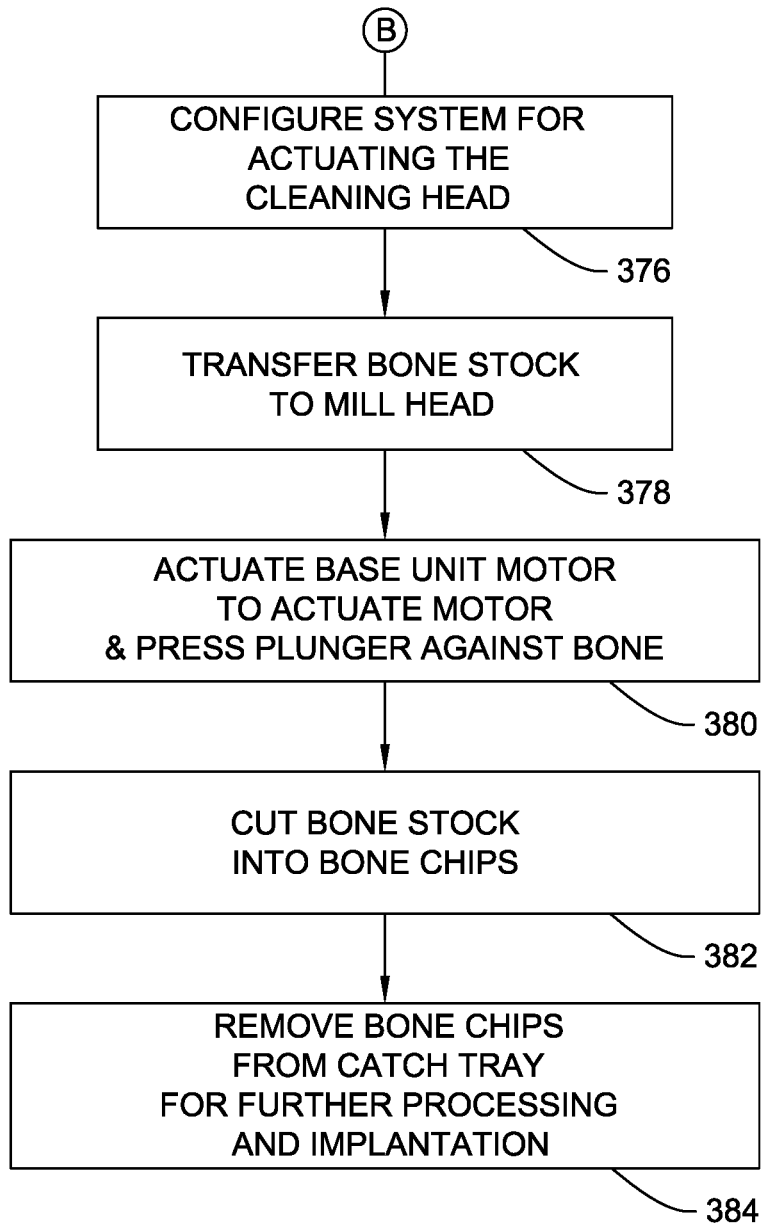

The absence of responses to these write request is interpreted by the display controller 164 that the base unit 52 is no longer attached to the console or the system component, the cleaning head or the mill head, is not longer attached to the base unit. While not represented in the flow chart of FIGS. 19A through 19C, it should be understood that these basic interrogation processes are repetitively executed as long as the control console 66 is turned on and connected to the base unit 52.

Based on the data the brush RFID 270, display controller configures system 50 for operation to clean the bone, step 362. Step 362 involves generating a sequence of instructions that indicate the speed and direction in which the motor should rotate. As part of step 362, the display controller 164 also causes to be presented on the display 174 information about the state of the system 50. These data include data indicating that the attached device is bone cleaning head, the speed range at which the base unit 54 should operate as well as the default operating speed. The surgical personnel can, if they want to, in a step 364, set the system for operating based on personal preferences of the characteristics of the bone disposed in the cleaning head 56.

The surgical personnel then actuate the cleaning head by depressing base unit button 120, (step not illustrated). In response to the depression of button 120 display controller 164, in step 368, causes motor driver 142 to apply energization signals to the base unit 54 to cause the motor to turn in the directions in which the lower brush should be turned. Initially, the spindle teeth may not be seated in the brush notches 264. However, owing to the alignment of the brush with the spindle, after less than 90° rotation of the spindle and the biasing force provided by spring 118, spindle teeth 112 seat in the brush head notches 264. Once the spindle teeth 112 are so seated, the continued rotation of the spindle 104 results in a like rotation of cleaning head lower brush 58.

As discussed above, once the cleaning head shells 192 and 194 are clamped together, the harvested bone is pressed between the bristles 268 and 290 of, respectively, the lower brush 58 and upper brush 59. The rotation of the lower brush bristles, forces the bone to rub against both sets of bristles 268 and 290. The rubbing of the bone against the bristles strips ligaments and other debris off the bone so as to clean the bone, step 370. It is believed that once actuated, cleaning head 56 of this invention can clean bone stock in 5 minutes or less and, in some circumstances, 3 minutes or less.

It should be understood that during steps 368 and 370, the motor is actuated according the sequence data specified in direction field 278 in the memory 272. Likewise, unless modified by the user, the motor is run at a speed necessary to rotate the brush according to the data specified in default speed field 276.

At the conclusion of the cleaning process, cleaning head 56 is removed from the base unit 52. The cleaning head shells 192 and 194 are unlocked from each other so as to allow removal the cleaned bone from the head 56. Both these process are called out as step 372 in FIG. 19B.

Mill head 60 is then coupled to the base unit 52, step 373. To so position the mill head 60, the mill head bottom shell is seated on the pedestal surface 76 so that pedestal teeth 84 seat in bottom shell notches 312 and catch tray 310 seats in pedestal notch 83. Mill head 60 is releasably secured to the base unit 52 by the seating of the retaining arms 86 so that the arm fingers 88 seat in the top shell notches 328. During this process, the spindle alignment pin 110 seats in the mill element opening 332. This serves to alignment the mill element 62 with the drive spindle 104 so that the element openings 334 are on a circle disposed over the spindle teeth 112. The seating of base unit teeth 84 in mill head notches 312 prevents rotation of the mill head 60 relative to the base unit 52.

As mentioned above, as long as the display controller 164 recognizes that the base unit 52 is attached to the control console 66, the display controller 164, through RFID interface 168 continues to perform interrogations to determine whether or not a device is attached to the base unit. Once the mill head 60 is fitted to the base unit 52, in response to this basic interrogation, the mill head RFID 320, writes out data indicating that the mill head is attached to the base unit. In response to this event occurring, the display controller 164, in step 374, reads out all the data in the mill head RFID 320.

Based on the data read from the mill head RFID, in a step 376, display controller 164 configures system 50 to actuate the mill head 60. This process involves generating instructions to operate the base unit motor 54 at the speed which will cause the mill element 64 to rotate at the appropriate speed. Also, the display controller 164 causes data to be presented on the console display 174 to indicate that a mill head 60 is attached to the base unit 52.

The cleaned bone stock is placed in the feed sleeve 306 and the plunger 307 placed in the sleeve over the bone, step 378. Surgical personnel start the actual milling process by depressing the base unit button 120. The personnel also press downwardly on the plunger 307 so as to press the bone stock against the mill element 62. These two steps are called out as step 380 in FIG. 19C.

As a consequence of the display controller 164 detecting the depression of button 120, (step not identified) in step 380 the display controller 164, in step 380, sends instructions to the motor driver 162 that causes the driver to actuate the base unit motor 54 at the speed necessary to rotate the mill element 62 at the desired speed. Again, it should be understood that based on the data in memory 320 this speed may be different than the speed at which the motor 54 is actuated to activate the cleaning head 56. As a consequence of the bone being pressed against the mill element 62 and the mill element rotating so that the cutting edges 340 turn towards the impingement plate 308, the bone is compressed between the mill element scallops and the impingement plate. The mill element cutting edges 340 shear the bone stock into chips. The chips fall into the catch tray 310.

After the milling process, the catch tray 310 filled with bone chips is removed from the mill head, step 384. The chips are then extracted for further processing and subsequent implantation into the patient.

System 50 eliminates the need to hand clean bone stock before it is ground into chips. Thus, the possibility that the individual charged with cleaning the bone stock, will, in the cleaning process, rip a glove so as to result in the risk of cross contamination is likewise eliminated.

Still another feature of this invention is that the most costly non-disposable components used to perform the cleaning process, the base unit 52 and the control console 66, have two functions. These components are used to activate both the mill element 62 in the mill head 60 and the brush 58 in the cleaning head 56. This reduces the costs of providing system 50 of this invention.

The memories (RFIDs) 270 and 320 provide configuration data about, respectively, the brush 58 and mill element 62, with which they are associated. Control console 66, based on these configuration data, controls actuation of the base unit motor 54 so that the motor operates at the speed for the attached brush 58 or mill element 62. This minimizes the amount of time personnel need to configure the system 50 for operation when first the cleaning head and then the mill head are mounted to the base unit. Given that the data transfer from the cleaning head and the mill head is automatic, the likelihood the human error could result in the console receiving incorrect configuration/operational data is essentially eliminated. Thus, the control console 66 ensures that the base unit motor 54 operates at the appropriate speed regardless of which head, the cleaning head 56 or the mill head 60, is attached to the base unit 52.

Still another feature of system 50 of this invention is that, in some versions of the invention, the only disposable portions of the cleaning head 56 are the brushes 58 and 59. This further reduces the costs associated with operating system 50.

VI. First Alternative Cleaning Head

Figure 20:
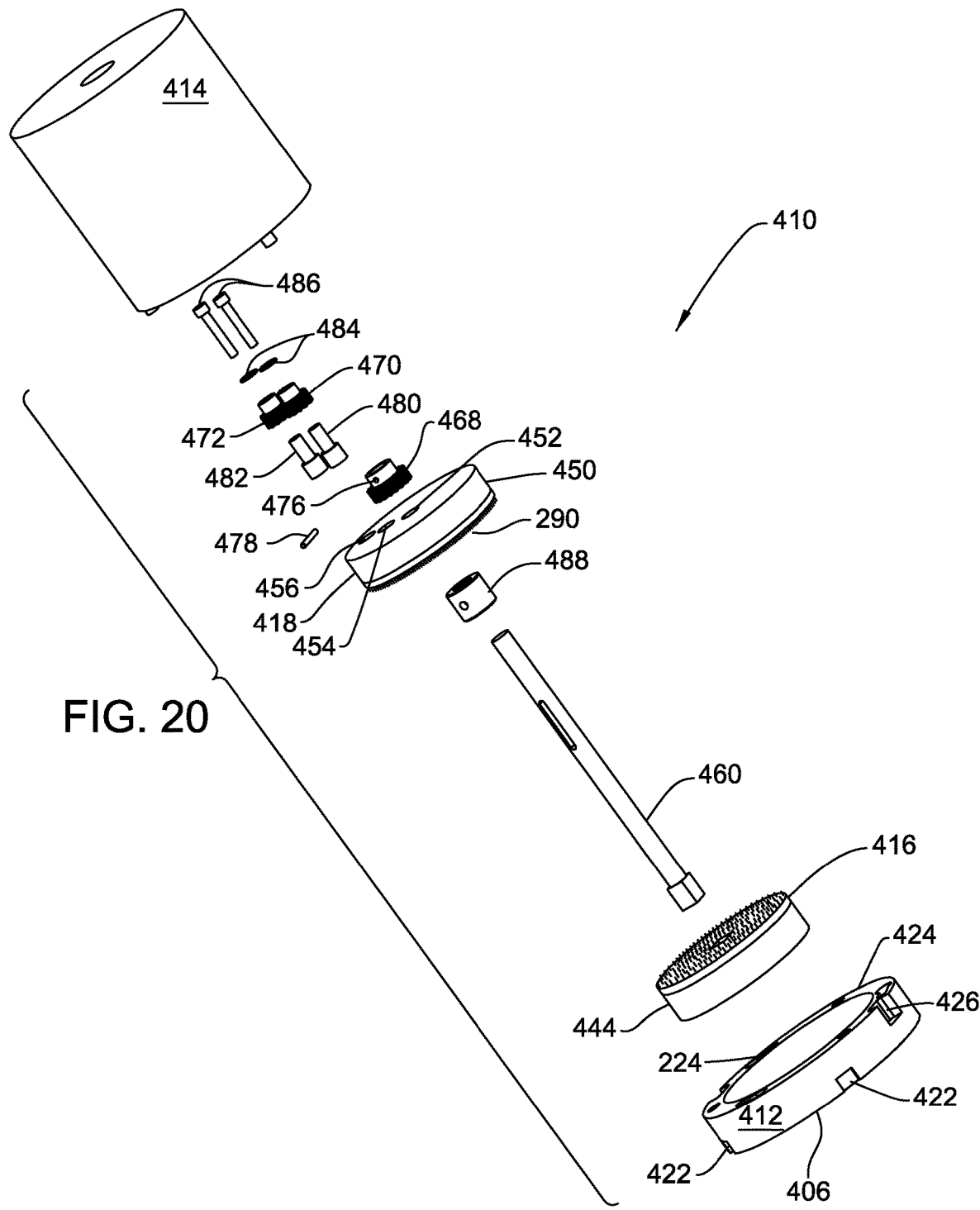
FIG. 20 is an exploded view of an alternative cleaning head of this invention.

FIG. 20 illustrates the basic features of an alternative cleaning head 410 for use with system 50 of this invention. Head 410 includes lower and upper shells 412 and 414, respectively. A lower brush 416 is disposed in the lower shell 412. An upper brush 418 is disposed in the upper shell 414. A drive assembly, the components of which are discussed below, connects the brushes for simultaneous rotation. In one version of the invention, the brushes are connected together so that when the lower brush 416 rotates in one direction, the upper brush 418 rotates in the opposite direction.

Lower shell 412 is formed from the same material from which lower shell 192 of cleaning head 56 is formed. The lower shell 412, seen best in FIG. 24, has the same basic circular shape as shell 192. More particularly, at the disk shaped base of the shell there is a center located opening (not illustrated) through which the base unit drive spindle 104 can extend. There are notches 422 in which the pedestal teeth 84 seat when cleaning head 410 is seated on the base unit 56. Lower shell 412 has a circular ring 424 that extends upwardly from the base. Ring 424 of shell 412 is shorter in height than ring 214 of shell 194. Accordingly the notches 426 formed in the ring in which the base unit retention arms 88 seat extend downwardly from the exposed outwardly directed face of the ring 426. Slots 224 are formed in the outwardly directed face of ring 424 for the same reason the slots 224 are present in shell 192.

Cleaning head upper shell 414 is formed from the same material from which the lower shell 412 is formed. Upper shell 414, like shell 194 of cleaning head 56, is cylindrically shaped. As seen best in FIGS. 20 and 21, upper shell 414 is larger in top-to-bottom height than shell 194. A number of coaxial bores extend longitudinally through upper shell 414. A bore 430 extends upwardly from the bottom of upper shell 414. Bore 430 extends approximately 50% of the distance through the shell 414 and is the largest diameter bore. A bore 432 is located immediately above and is contiguous with bore 430. Bore 432 has a diameter that is slightly less than that of bore 430. Upper shell 414 is shaped so that the outer perimeter of bore 432 is defined by a circular ring of teeth 434 that extends inwardly from an interior surface of shell 414.

Above bore 432 there is a bore 436, a bore 438 and a bore 440. Bore 436 is present for manufacturing reasons and has a diameter between that of bore 430 and bore 432. Bore 438 is immediately above bore 436. Bore 438 has a diameter less than that of bore 436. Bore 440 extends between bore 438 and the top face of shell 414. Bore 440 has a diameter less than that of bore 438.

The same pins 248 that extend downwardly from the base of upper shell 194 extend downwardly from the base of upper shell 414.

Figure 23:
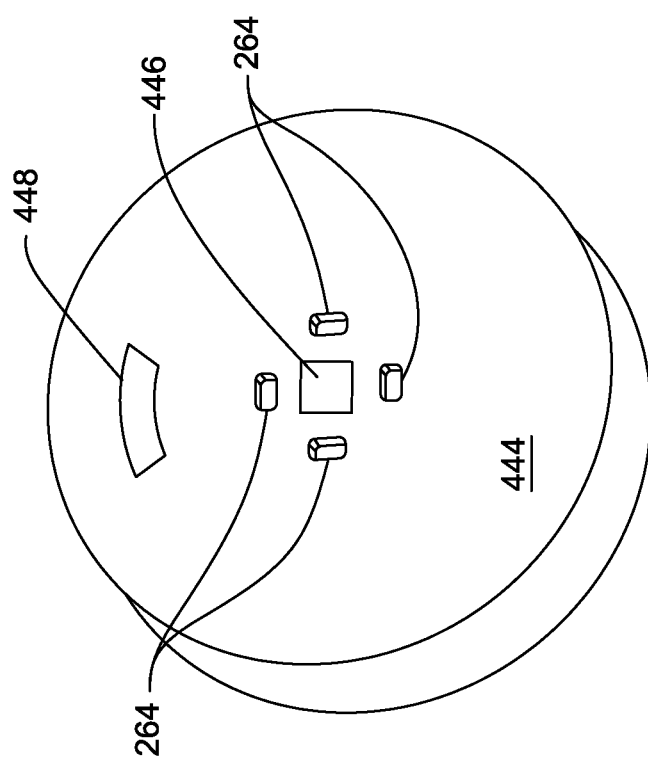
FIG. 23 is a perspective view of the underside of the lower brush substrate of the mill head of FIG. 20.

Lower brush 416 has a substrate 444 similar to substrate 260. As seen in FIG. 23, a bore 446 extends through substrate 444 along the axis around which substrate 444 rotates. Bore 446 has a square cross-sectional shape. The width across bore 446 is equal to or greater than the maximum outer diameter of the drive spindle alignment pin 110. The notches 264 present in substrate 260 are equiangularly spaced around the bore 446 of substrate 444.

Substrate 444 is further shown as having a closed end notch 448 on the underside of the substrate. This is to indicate that substrate 444, like substrate 260, holds the memory (RFID) 270 (FIG. 5) in which data regarding the identity and operation of the cleaning head 410 are stored.

Bristles 268 extend upwardly from the top directed face of substrate 444. Not identified is the adhesive layer between the substrate 444 and the bristles.

Upper brush 418 has a disc shaped superstrate 450 with an outer diameter at least 0.5 mm smaller than the diameter of shell bore 430. Superstrate 450 is formed with three bores. A through bore 452 extends axially through the substrate along the longitudinal axis of the substrate. There are also two closed end bores 454 and 456. Bores 452, 454 and 456 are linearly aligned. Bore 456 is located immediately inward of the outer perimeter of superstrate 450.

The drive assembly of cleaning head 410 includes a shaft 460, now described by reference to FIGS. 24 and 25. Shaft 460 is formed from stainless steel or other metal or, in some cases, as plastic and as a single piece unit. The shaft 460 is shaped to have a generally elongated cylindrical body 462. Body 462 has a diameter that is less than the diameter of bore 452 of upper brush substrate 450. Formed integrally with the body 462, at the bottom end of the body, shaft 460 has a foot 464. Foot 464 has a rectangular cross-sectional profile. More particularly, shaft foot 464 is shaped to closely fit in bore 446 internal to lower brush substrate 444. While not illustrated, shaft foot 464 may have a bore that extends upwardly from the base of the foot. This bore is shaped to receive the alignment pin 110 integral with the base unit drive spindle 104. Shaft 460 is further formed to have an elongated slot 466. Slot 466 is located in shaft body 462 approximately 2 to 4 cm below the top of the shaft. Slot 464 extends diametrically through the shaft body 462.

Figure 21:
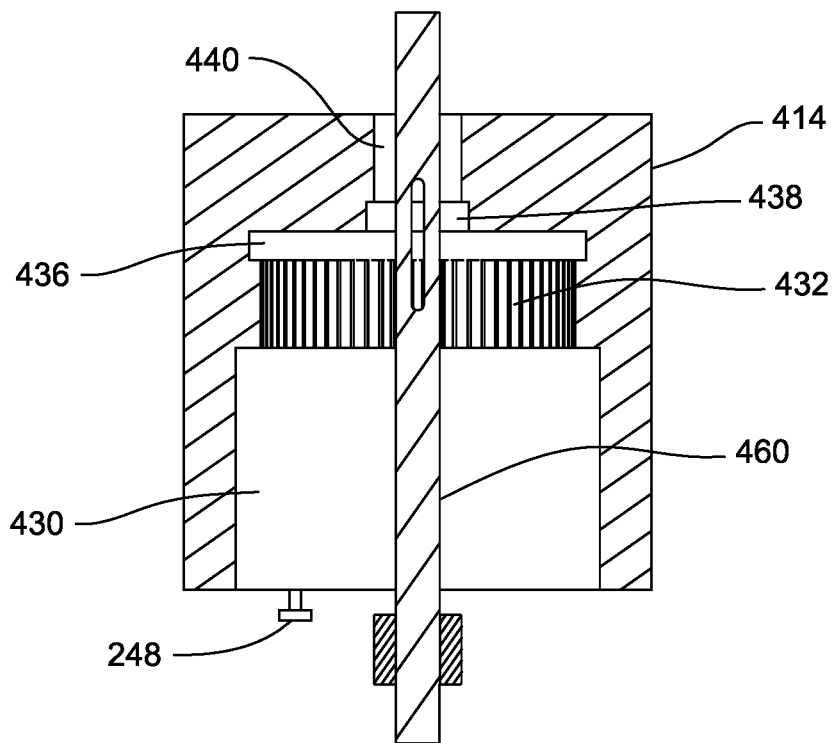
FIG. 21 is a cross sectional view of the upper shell and shaft of the mill head of FIG. 20.
Figure 22:
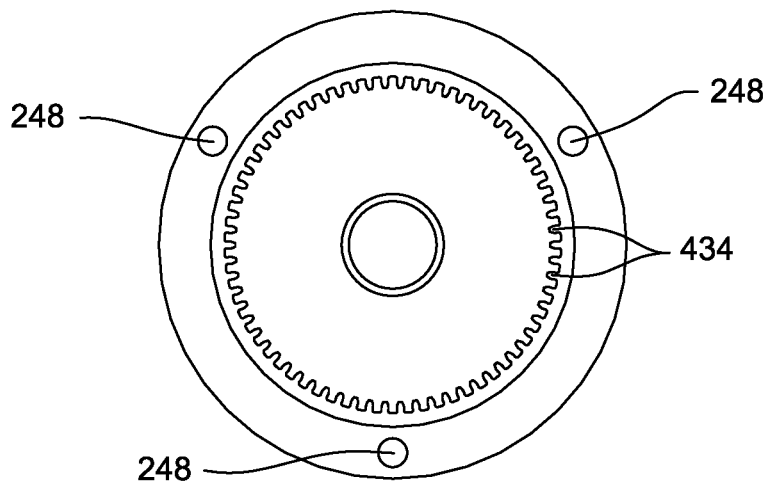
FIG. 22 is a plan view looking upwardly, of the bottom of the upper shell, shaft and spacer ring of the mill head of FIG. 20.

Shaft 460 is positioned so that foot 464 is seated in lower brush substrate bore 446. The shaft body 462 extends through and above bore 452 in the upper brush substrate 450. As seen in FIG. 21, shaft body 462 also extends through upper shell bores 436, 438 and 440.

Figure 24:
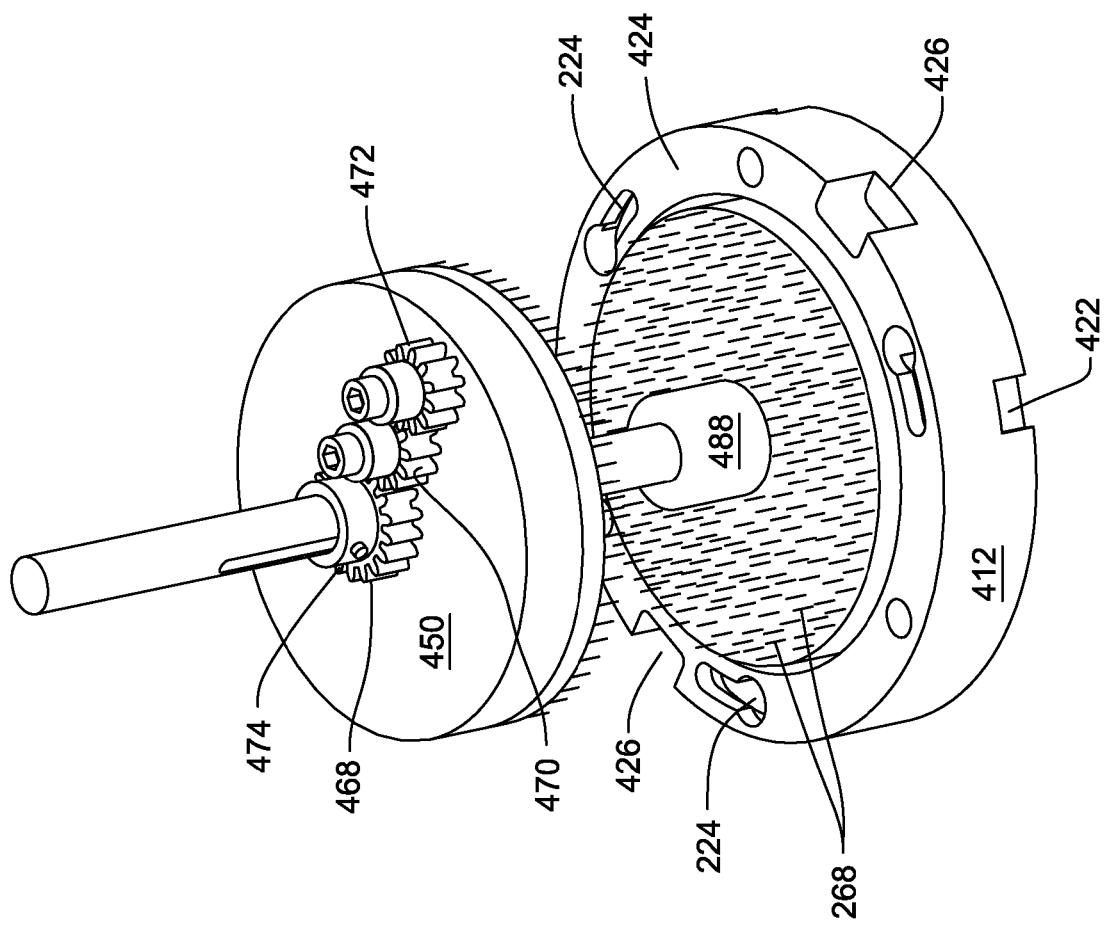
FIG. 24 is a perspective view of the drive assembly of the mill head of FIG. 20.
Figure 25:
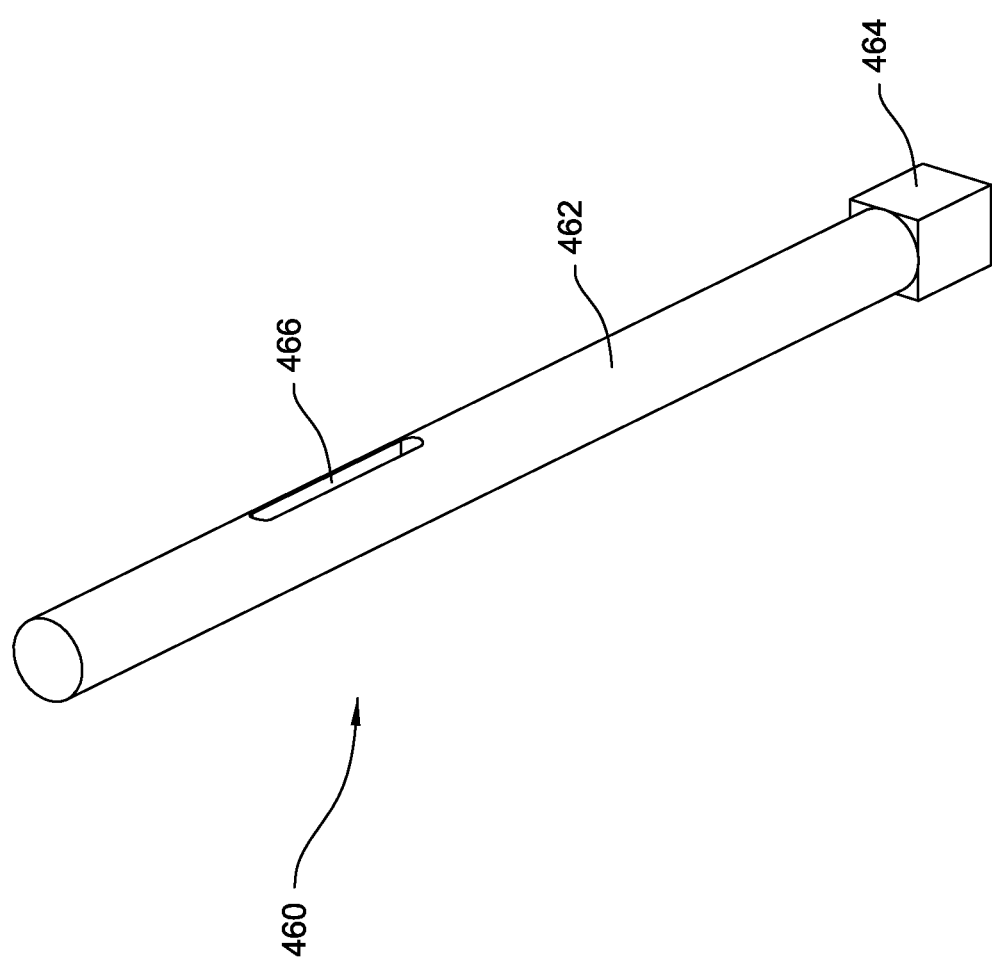
FIG. 25 is a perspective view of the drive shaft of the mill head of FIG. 20.

The cleaning head drive assembly also includes three gears 468, 470, 472 located immediately above the top of the upper brush substrate 450 as seen best in FIGS. 20 and 24. Gear 468 is slip fitted over the section of the shaft body 462 that extends above the superstrate 450. A ring shaped collar 474 integral with gear 468 extends upwardly from the gear so as to also extend around the shaft body 462. Collar 474 is formed to have diametrically opposed openings 476, one shown. A pin 478 extends through collar openings 476 and shaft slot 466 to couple gear 468 to the shaft 460 so that the gear rotates with the shaft. Given that pin 478 extends through shaft slot 466 it should be apparent the gear 468, like upper brush 418, is able to move longitudinally along shaft 462.

It should further be appreciated that when cleaning head 410 is assembled, collar 474 may extend into upper shell bore 438. Accordingly, the upper shell 414 is formed so that bore 438 is of larger diameter than collar 474.

Gears 470 and 472 are both rotationally mounted to the top surface of superstrate 450. More particularly, gear 470 is disposed over the shaft of an arbor 480 seated in superstrate bore 454. Gear 472 is disposed over the shaft of an arbor 482 seated in superstrate bore 456. Pins 486 hold the gears 470 and 472 to, respectively, arbors 480 and 482. A washer 484 is disposed between each gear 470 and 472 and the overlying pin head. Gear 470 interlocks with both gears 468 and 472. Gear 472 is positioned so the teeth of the gear project beyond the perimeter of superstrate 450.

Bristles 290 extend downwardly from superstrate 450. Not identified is the adhesive layer that holds the bristles 290 to the superstrate.

Cleaning head 410 also includes a ring 488. Ring 488 is dimensioned to slip fit over the shaft body 462. For reasons apparent below, this version of the invention may include a number of different rings of different heights.

Bone stock is cleaned using cleaning head 410 by first placing the lower brush 416 in lower shell 412. Shaft 460 is mounted to the brush 416 so the shaft foot 464 seats in substrate bore 446. A ring 488 having a height slightly less than the height of the bone stock is slipped over the shaft body 462. The bone is placed on the brush bristles 268.

Upper brush 418 is disposed over the lower brush so the shaft body extends through superstrate bore 452. It should be appreciated that the presence of ring 488 limits the extent to which the upper brush 418 is pushed down against the bone stock.

The upper shell 414 is then disposed over the lower shell 412, the bone stock and the brushes 416 and 418. As a consequence of the positioning of the upper shell 414 in place, the teeth of the gear 472 that extend beyond upper brush substrate 450 engage the teeth 434 internal to the upper shell 414.

Cleaning head 410 is then releasably coupled to the base unit pedestal 74 in the same manner in which cleaning head 56 is so attached. The cleaning head 410 is actuated in the same general process in which cleaning head 56 is actuated. If the cleaning head, more particularly, the lower brush 416 is provided with a memory 270, in which data defining the operational parameters of the cleaning head are stored, control console 66 activates the base unit motor 54 based on these data.

During the actuation of the cleaning head 410, base unit spindle 110 rotates the lower brush 416. This results in a like rotation of shaft 460. The rotation of shaft 460 results in the rotation of gears 468, 470 and 472. The engagement of the teeth of gear 472 in upper shell teeth 434 results in the rotation of upper brush 418 around the shaft 460. More particularly, superstrate 450 and the upper brush are rotated in a direction opposite that in which the lower brush 416 rotates. Thus, bristles 268 and 290 simultaneously rub against opposed surfaces of the bone stock in opposed directions. This simultaneous brushing of two surfaces of the bone stock in opposed directions rolls the bone stock between the brushes during the cleaning process. This facilitates the thorough cleaning of the bone stock and potentially reduces the overall time required to clean the bone stock.

VII. Integrated Cleaning and Mill Head

Figure 26:
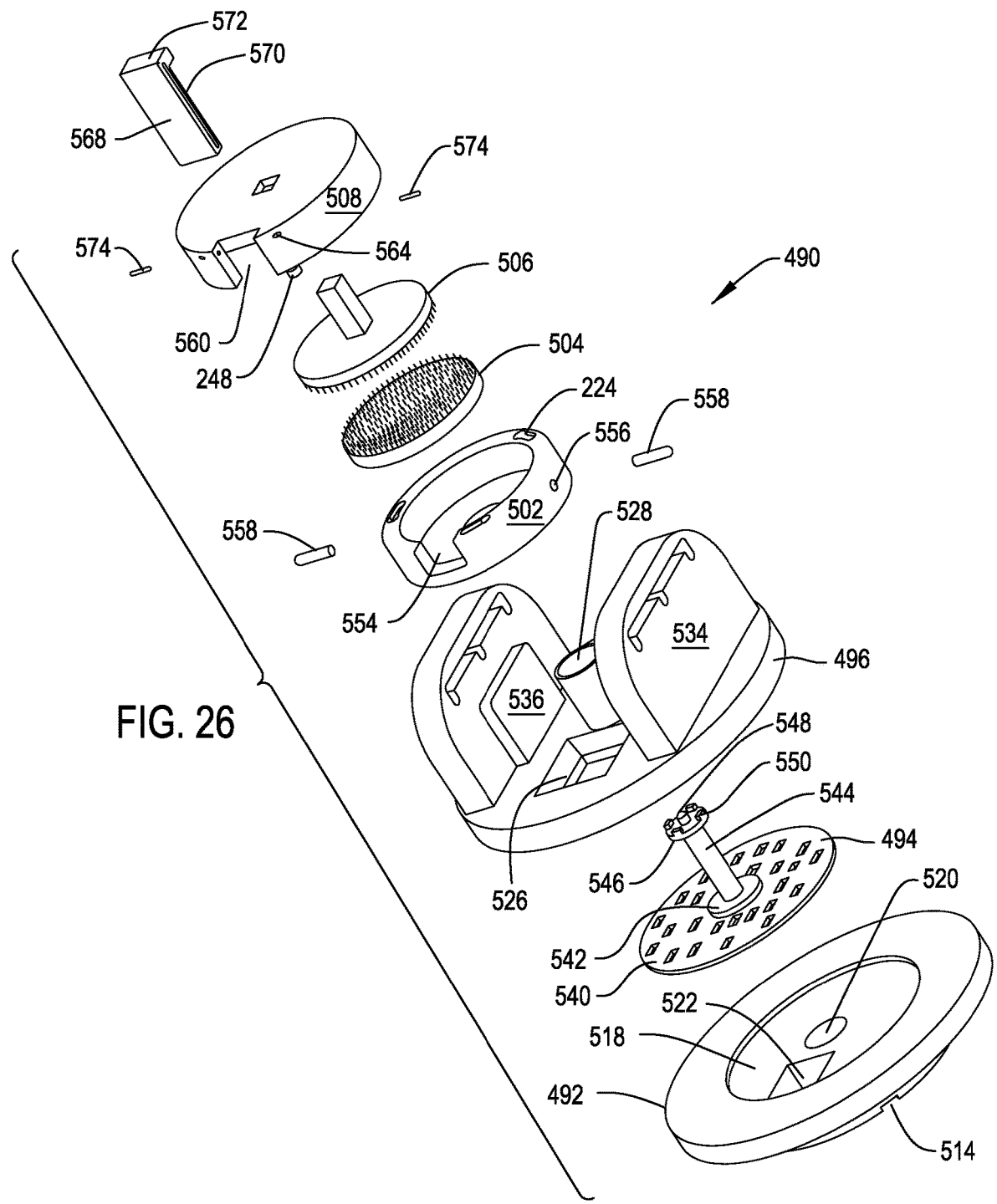
FIG. 26 is an exploded view of the integrated cleaning and mill head of this invention.

In another alternative version of this invention, the system may include a single head 490 now described by reference to FIG. 26, with components for both cleaning and milling bone stock. Head 490 includes lower and upper plates 492 and 496, respectively. Rotatably disposed between the plates 492 and 496 is a mill element 494. A cleaning module, including lower and upper shells 502 and 508, respectively is moveably mounted to upper plate 496. Lower and upper brushes 504 and 506, respectively, are disposed inside the brush housing. Lower brush 504 is provided with features that releasably couple the brush to the mill element 494 so that the brush rotates in unison with the mill element.

Figure 27:
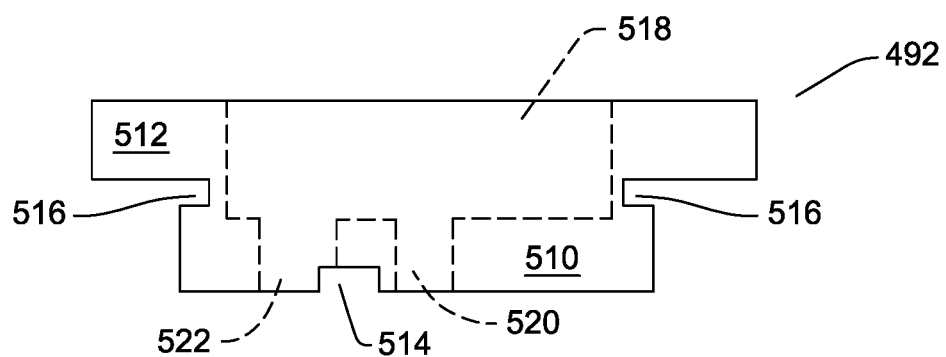
FIG. 27 is a side plan view of the lower plate of the head of FIG. 26.

The head lower plate 492, is formed from a plastic such as a sterilizable plastic such as a polycarbonate plastic. As seen in FIG. 27, the lower plate is formed to have cylindrical base 510. Base 510 has a diameter that allows it to seat on the base unit pedestal top surface 76 within lip 78. Base 510 has a height that is at least as great as that of lip 78 above surface 76. Lower plate 492 is further formed to have a rim 512 that is integral with and extends circumferentially and radially beyond base 510. The base is formed so as to have four notches 514 and two notches 516 (one notch 514 seen in FIG. 27). Notches 514 are located around the bottom surface of base 510. Notches 514 are dimensioned to receive teeth 84 when head 490 is seated on base unit 52. Notches 516 are diametrically opposed to each other. Notches 516 are located at the top of base 510 immediately below when the rim 512 projects outwardly from the base. The notches 516 are positioned and dimensioned to receive the retention arms fingers 88 to facilitate the releasable coupling of the head 490 to the base unit 52.

Lower plate 492 is further formed so as to have a circular void space 518 concentric with and located within rim 512. More specifically the lower plate 492 is formed so that the void space 518 extends through rim 512 and partially through the base 510. A circular opening 520 seen in phantom in FIG. 27, extends concentrically from the bottom of void space 518 through the plate base 510. Opening 520 has a diameter slightly greater than that of the drive spindle head 108. The lower plate is also formed with a discharge port 522. Discharge port 522 is square in cross section and extends from the bottom of the void space through the plate base 510. Port 522 is located between opening 520 and the outer perimeter of plate base 510.

While not seen in the Figures, it should be understood that a catch tray similar to catch tray 310 is removably mounted to the lower plate base 510. Also not illustrated are the rails integral with the lower plate 492 that facilitate the removable mounting of the catch tray below discharge port 522.

Upper plate 494 is formed from the same type of plastic from which lower plate 492 is formed and is generally disc-shaped. The upper plate 494 has an outer diameter equal to the outer diameter of base plate rim 512. The upper plate 494 is formed to have a center located hole 524 (shown in phantom in FIG. 28). Upper plate 496 is further formed to have a feed port 526. Feed port 526 is generally square in shape. In the illustrated version of the invention the plate is shaped so that the interior surfaces of the plate 496 that lead into the port are inwardly tapered such that the size of the port 526 decreases progressing inwardly from the top of the plate. When head 490 is assembled, the plates 492 and 496 are oriented so that the upper plate feed port 526 is in registration with the lower plate discharge port 522.

The upper plate 496 is further formed to have a center located tube-shaped sleeve 528. The plate is formed so that sleeve 528 extends around and above plate center located-hole 520.

Figure 28:
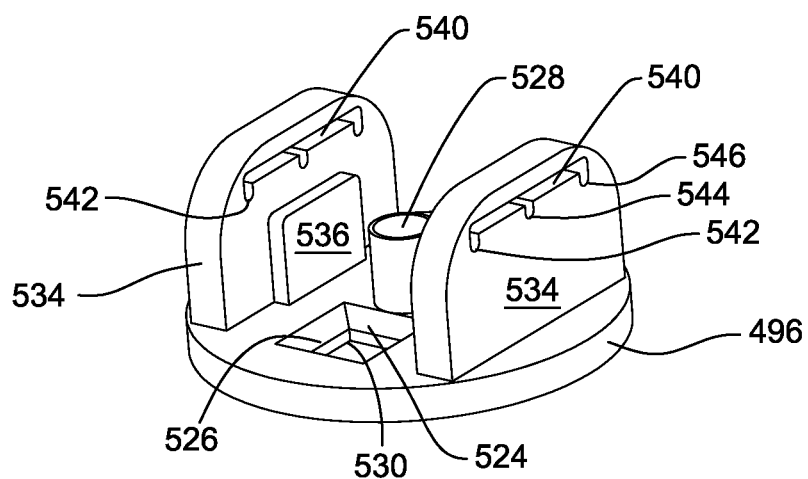
FIG. 28 is a perspective view of the upper plate of the head of FIG. 26.
Figure 29:
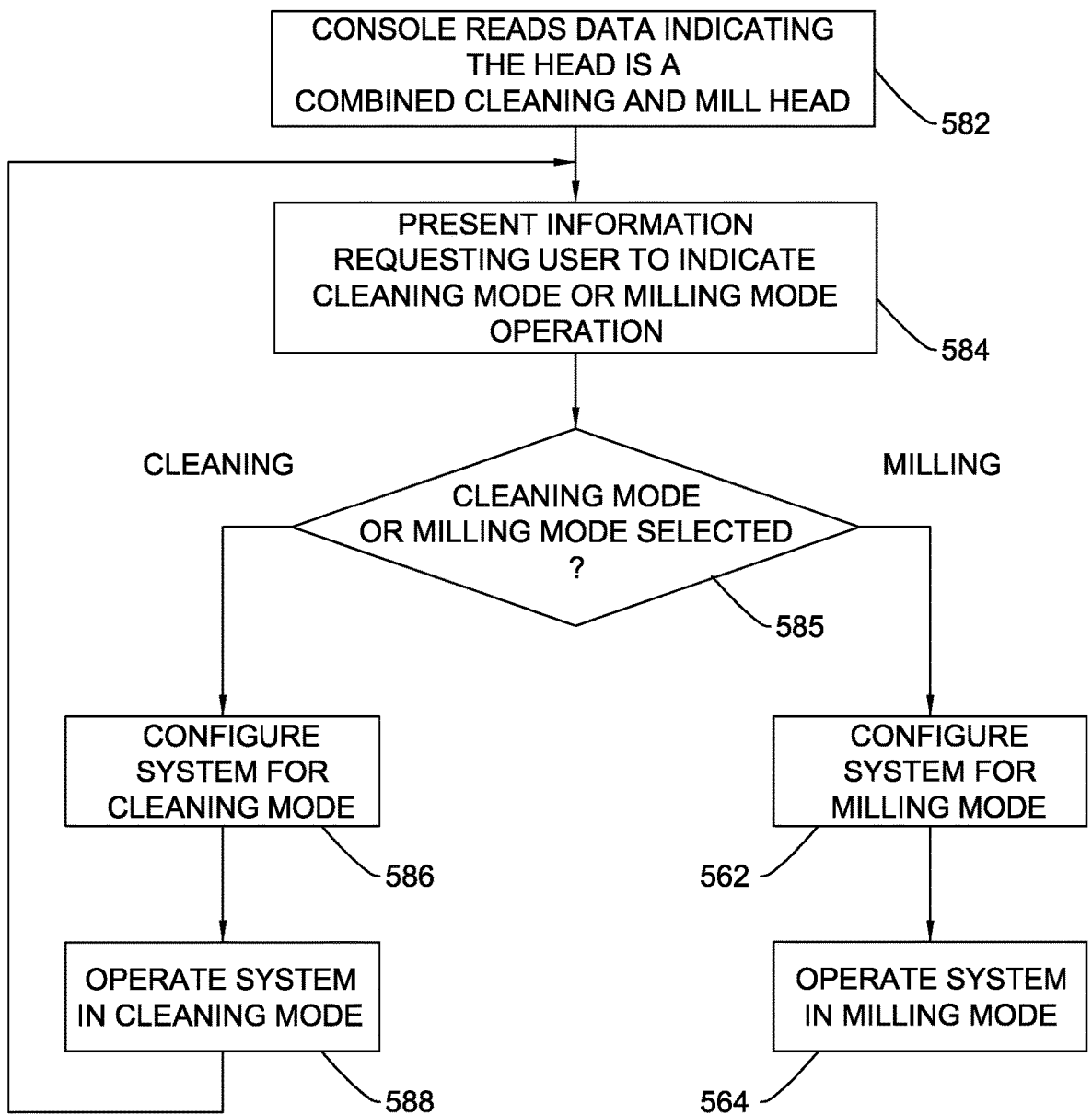
FIG. 29 are a flow chart of the process steps executed during the operation of the head of FIG. 26.

An impingement plate 530, seen as a phantom rectangle in FIG. 28, is mounted to the bottom of the upper plate 496. The impingement plate 530 is located immediately adjacent the plate feed port 526.

Two parallel webs 534 extend upwardly from upper plate 496. In some versions of the invention, webs 534 are formed integrally with the upper plate 496. The webs 534 are positioned so that the plate hole 524, feed port 526 and sleeve 528 are located between the webs. Webs 534 are spaced apart from each other a distance greater than the outer diameter of shells 502 and 508. In the illustrated version of the invention, a rectangular rib 536 is formed integrally with each web 534. Each rib 536 (one shown) extends outwardly from the face of the web that is directed toward sleeve 528. Ribs 536 provide structural strength to the webs 534.

Webs 534 are generally solid structural members. Each web 534 is further formed to have a slot 540 immediately below the top of the web that extends across the web. The slots 540, which are in registration with each other, are each formed to have three downwardly directed indentations 542, 544 and 546. Two indentations, indentations 542 and 546, are located at the opposed ends of each slot. Each indentation 544 extends downwardly from the mid-point of the slot 540 with which it is integral.

Mill element 494 includes a cutting disc 540. Disc 540 has the same basic features of mill element 62. Disc 540 has an outer diameter slightly less than the diameter of the lower plate void space 518. Mill element 494 also has a post 544 that extends upwardly from the top surface of disc 540, the surface above which the disc scallops (not identified) extend. In the illustrated version of the invention, post 544 extends upwardly from a circular base 542 welded or otherwise secured to the top of disc 540. Post 544 has a diameter less than that of the underlying base 542.

A circular head 546 is mounted to the top of post 544. Head 546 is shaped to have an alignment pin 548 similar to spindle alignment pin 110. The head 546 also has teeth 550 similar in drive teeth 112 integral with drive spindle 112. Teeth 550 are disposed equiangularly around and are smaller in height than pin 548. Mill element 494 is dimensioned so that when head 490 is assembled, the cutting disc 540 is disposed in the lower plate void space 518, post 544 extends through sleeve 528 and element head 546 is spaced above the sleeve.

Lower shell 502 has the same basic shape of shell 192 of cleaning head 56. Shell 502 does not have notches that facilitate the seating of the shell or the coupling of the shell to the base unit 52. Shell 502 has a notch 554 that extends downwardly from the outer lip of the shell. In some versions of the invention, notch 554 extends to the base of the shell 502. Lower shell 502 is further formed to have two diametrically opposed, linearly aligned closed end bores 556.

Pins 558 moveably mount the lower shell 502 to webs 534 integral with upper plate 494. Each pin 558 has an end that is seated in one of the shell bores 556. The end of the pin 558 that extends outwardly of the shell 502 extends into the adjacent web slot 540. Pins 558 are dimensioned relative to the slots 540 so that the pins can slidably move in the slots and indentations 542-546. It should therefore be appreciated that the pins 558 allow the lower shell 502, and the components mounted to the shell, to both move over the upper plate 496 and to pivot.

Upper shell 508 has the same basic cylindrical shape as shell 194 of cleaning head 56. A rectangularly shaped notch 560 extends through the downwardly extend skirt of the shell 194 (skirt not identified). Collectively, shells 502 and 508 are shaped so that, when assembled together to form the cleaning module housing, upper shell notch 560 is in registration with lower shell notch 554. It should also be understood that notches 554 and 560 share a common width. Two linearly aligned laterally extending bores 564 are also formed in upper shell 508. Bores 564 are positioned to open into notch 560.

Pins 248 (one shown) integral with upper shell 508 seat in slots 224 formed in the lower shell 502 to facilitate the releasable coupling of the shells together. Again, collectively, shells 502 and 508 form the housing of the cleaning module of head 490.

Lower brush 504 has the same basic features of brush 58. Upper brush 506 has the same basic features of brush 59.

Head 490 of this version of the invention also includes a slide plate 568. Plate 568 is mounted in contiguous notches 554 and 560 integral with the cleaning module housing. Plate 568 has a generally rectangular shape. The width of the plate 568 is selected to facilitate the sliding movement of the plate 568 in the notches 554 and 560. The opposed side surfaces of the plate 568 are each formed to have longitudinally extending groove 570 (one shown). A tab 572 extends perpendicularly away from the plate 568. In the illustrated version of the invention, the plate 568 is constructed so that when the head 490 is assembled, tab 572 extends over the top of the upper shell 508.

Two pins 574 hold the plate 568 to the cleaning module housing. More particularly, each pin 574 is partially seated in one of the bores 564 formed in the upper shell 508. The exposed end of the pin 574 seats in the adjacent groove 570 integral with the plate 568. Pins 574 thus hold the plate to the cleaning module housing while allowing the plate to slide so as to selectively cover and expose notches 554 and 560.

While not illustrated, a memory similar to memory 320 may be disposed in the lower plate base 510. This memory includes data indicating the speeds at which both the mill element 494 and lower brush 504 should be rotated.

To use head 490, the head is initially mounted on the base unit 52. As a consequence of the seating of the lower plate base 510 on base unit pedestal surface 76, the drive spindle alignment pin 110 causes mill element 494 to align with the drive spindle 104.

To load bone stock for cleaning in the cleaning module, the module is first moved so that pins 558 seat in web slot indentations 546. The cleaning module is thus positioned so it is spaced furthest away from the upper plate feed port 526. The cleaning module is then pivoted so notches 554 and 560 and plate 568 are upwardly directed. Plate 568 is opened to expose notches 554 and 560. The bone stock is passed through the notches, between the brushes 504 and 506. To ensure sufficient clearance between the notches, the person perform this process may pull on the post integral with brush 506 to hold it away from brush 504. Plate 568 is returned to the closed state.

The cleaning module is then moved so that pins 554 seat in web slot indentations 544. As a consequence of the cleaning module being so positioned, the alignment pin 548 integral with mill element 494 in the complementary opening formed in brush 504 aligns the drive openings internal to the brush with the circle in which teeth 550 are disposed. Collectively, the components of head 490 may further be constructed so that when pins 558 seat in indentations 544, the undersurface of lower shell 502 seats against sleeve 528.

The memory integral with head 490 contains data that informs the control console display controller 164 that the head is a combined cleaning and mill head, step 582 of FIG.

29A. In response to this information, display controller 164 presents on display 174 buttons requesting the user to indicate if the device is to be operated in the cleaning mode or the milling mode, step 584. Upon entry of a command, step 585, that the device is to be operating in the cleaning mode, display controller, in step 586, prepares the instructions to cause the motor driver 162 to actuate the motor 54 in a manner appropriate to rotate brush 504 at the appropriate speed and in the appropriate direction. Once button 120 is depressed, (step not shown) control console 66 actuates the motor 54 so as to cause the appropriate actuation of the cleaning module, step 588.

In step 588 the actuation of the motor 54 and drive spindle 108 result in a like actuation of the mill element 494. The cutting disc 540, post 544 and head 546 are all rotated. If teeth 550 are not already seated in the brush openings, identical to openings 264 of FIG. 12, they seat in these openings during the initial rotation of the head 546. As a consequence of the engagement of teeth 550 in the brush openings, the brush undergoes a like rotation. As with the rotation of brush 58, this action results in the cleaning of the bone stock.

Once the cleaning processes is terminated, the control console may return to step 584 to await an indication if, the next time the motor is actuated, it is actuated to actuate the mill element 494 or the brush 504

Once the bone is cleaned, the cleaning module is moved so that pins 554 seat in web slot indentations 542, the indentations adjacent feed port 526. The cleaning module is pivoted so that the module notches 554 and 560 face the feed port 526. Plate 568 is slide to the open state. Gravity causes the cleaned bone stock to fall into the feed port 526. To facilitate this process, it may be necessary to pull on the post integral with brush 506 so as to hold the brushes apart.

Once the bone stock is transferred to the lower plate, essentially the mill assembly, the cleaning module is moved away from the feed port 526. This provides clearance for the subsequent insertion of a plunger into the feed port.

The user depresses the appropriate button presented on the control console display 174 to indicate that head 490 is now to be operated in the cleaning mode, step 585 is reexecuted. In response to this button being depressed, in step 562, the display controller 164 readies the instructions to cause the base unit motor 54 to be actuated at a speed appropriate for rotating the cutting disc 540, step 562.

When the bone is to be milled the button 120 is depressed, (step not illustrated). This results in the control console 66 actuating the base unit motor 54 at the appropriate speed, step 564. Simultaneously with the actuation of the motor a plunger, such as the plunger 307 of FIG. 16, is used to force the bone stock against the rotating cutting disc 540. The rotating cutting disc 540 and impingement plate 530 cooperate to convert the bone stock into bone chips.

One advantage of head 490 of this invention is that a single unit includes the components that first clean the bone stock and then mill the stock into chips. The need to change heads between these processes is eliminated. A further advantage of a system of this invention including head 490 is that the transfer of the cleaned bone from the cleaning module to the mill module occurs using gravity. The need to have an individual perform this transfer is eliminated.

It should of course be appreciated that there may procedures in which it may be appropriate to use one of the cleaning module or the milling module of this invention but not both the modules of head 490.

VIII. Alternative Brush

Figure 30:
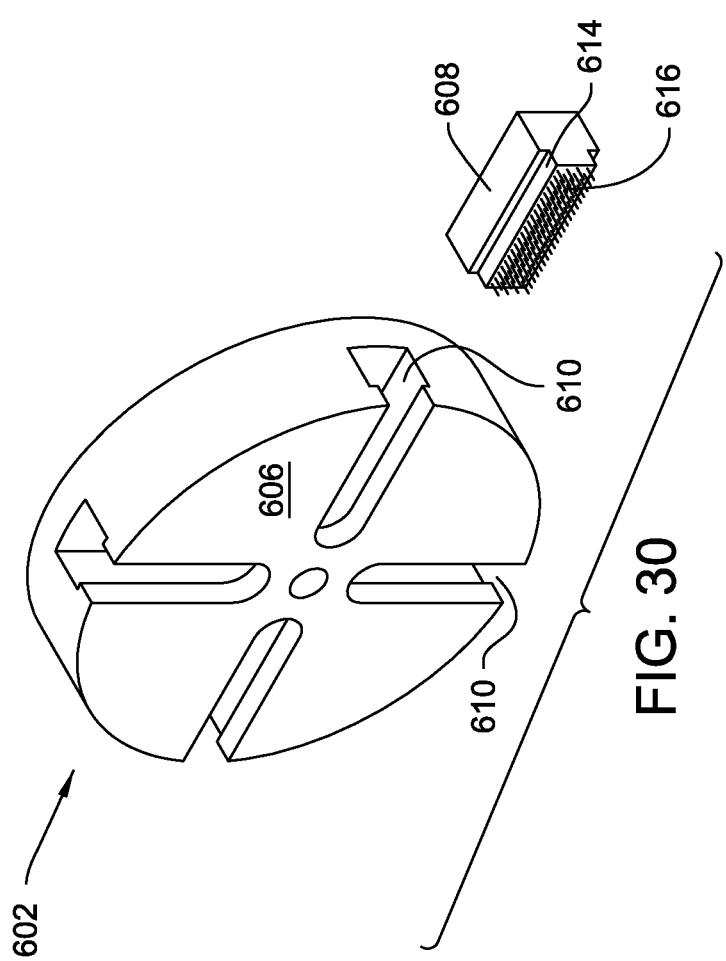
FIG. 30 is an exploded view of an alternative brush of the system of this invention.
Figure 31:
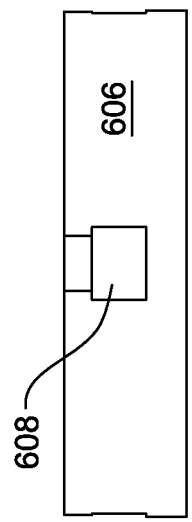
FIG. 31 is a side plan view of the substrate/superstrate of the brush of FIG. 30.

FIGS. 30 and 31 illustrate an alternative brush 602 that can be employed with the system of this invention. The illustrated brush 602 is a lower brush. Versions of the brush can be configured as an upper brush. Brush 602 includes a disc substrate 606. A number of brush heads 608 (one shown) are removably attached to the substrate 606.

Substrate 606 is dimensioned to fit in and rotate in the head/module in which the brush 602 is seated. Not shown is the opening on the underside of the substrate for receiving the alignment pin 110 or 548. Also not shown are the openings in the underside of substrate 606 for receiving the drive teeth 112 or 550. Substrate 606 is formed to have four equiangularly spaced apart slots 610. Each slot 610 starts from a location radially spaced from the center of the substrate and extends radially outwardly to the outer perimeter of the substrate. While not identified, it can be seen in the Figures that each slot 610 includes a wide width lower section and an upper section with narrower width. The slot lower section, it is observed, form the closed end base of the slot 610. Slot 610 upper section is open to the surface of substrate 606.

Each brush head 608 includes a rectangular base 614. Base 614 has a width that allows the base to slide in the lower section of substrate slot 610. Bristles 616 extend upwardly from the top surface of base 614. Bristles 616 may be adhesively secured to the base 614. Alternatively, the bristles may be compression packed in closed end bores (not illustrated) in the base. Regardless of how the bristles 616 are mounted to the base 614, the bristles are extend across the base a distance approximately equal to that of the width of the upper section of slot 610. Bristles 616 are of sufficient length that the bristles extend above and out of the upper section of slot 610.

Brush 602 of this invention is prepared for use by sliding a brush head 608 in each one of the substrate slots 610. Brush 602 is then mounted the cleaning head/module and used in the same manner as the previously described brushes 58, 59, 416, 418, 504 or 506.

Once a system of this invention in which one or more brushes 602 is employed, the brush heads 608 can be removed from the substrate (or superstrate) for cleaning or disposal and replacement. The substrate (or superstrate) can be independently sterilized. Thus use of brushes 602 of this version of the system of the invention thus eliminate the need to, after each use, discard the whole of the brush.

IX. Second Alternative Cleaning Head

Figure 32:
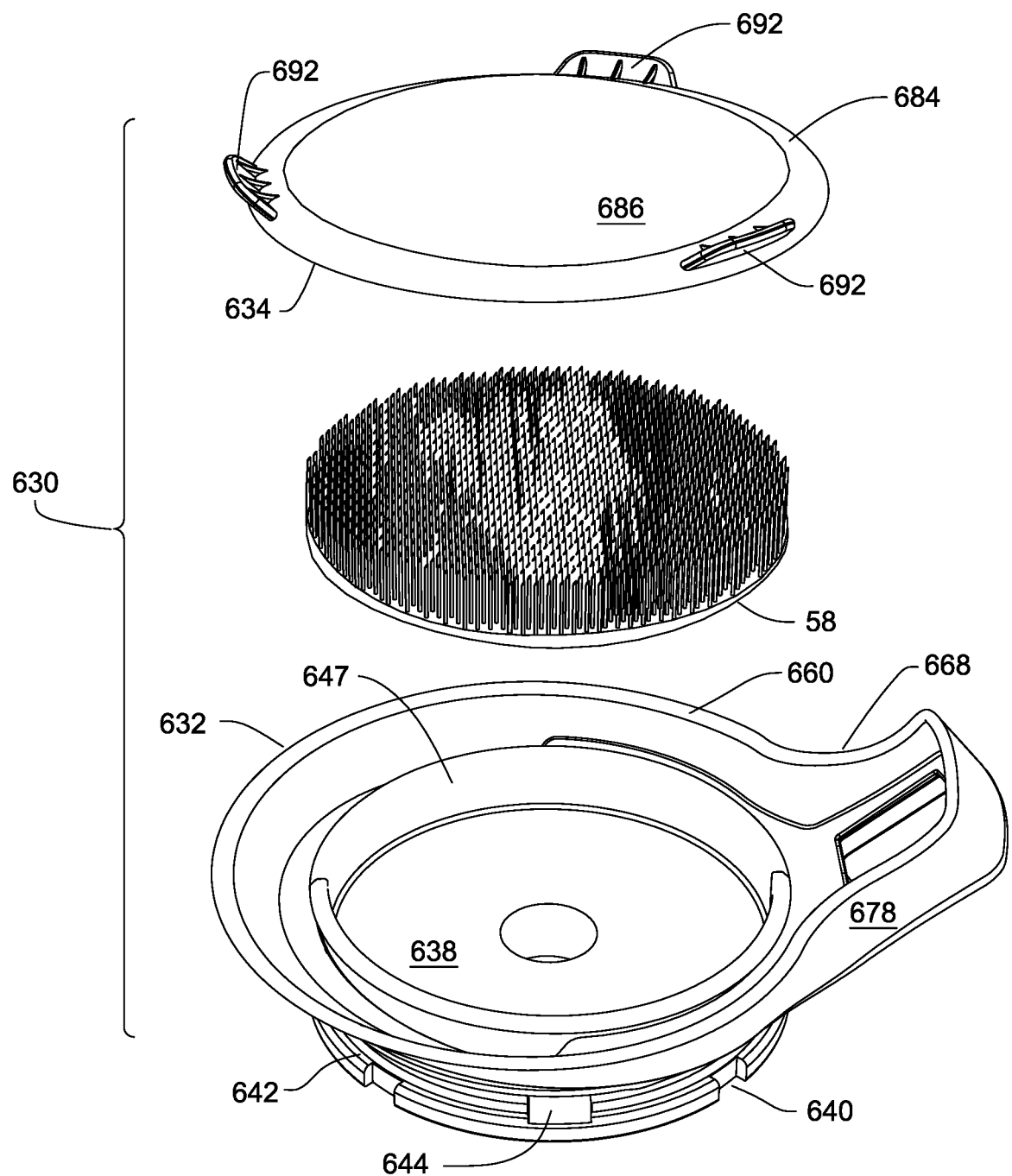
FIG. 32 is a exploded view of a second alternative cleaning head of this invention.

A second alternative cleaning head 630 of this invention is now described by initial reference to FIG. 32. Cleaning head 630 includes a base 632. Base 632 is dimensioned to be seated over the base unit top surface 76. Brush 58 (or brush 602) is rotatably disposed within the base 632. A flexible cap 634 is fitted to the base 632 so as to extend over the brush 58.

Figure 34:
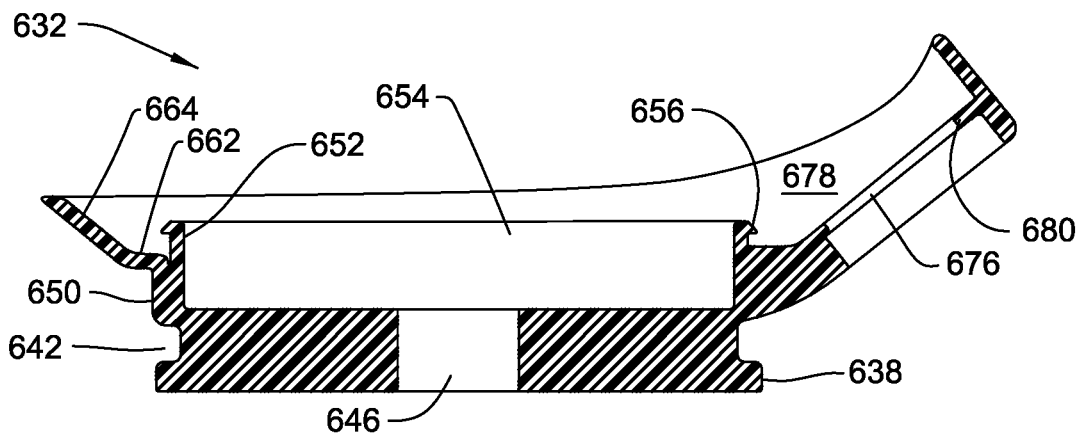
FIG. 34 is a cross sectional view along line 34-34 of the base of FIG. 33.
Figure 33:
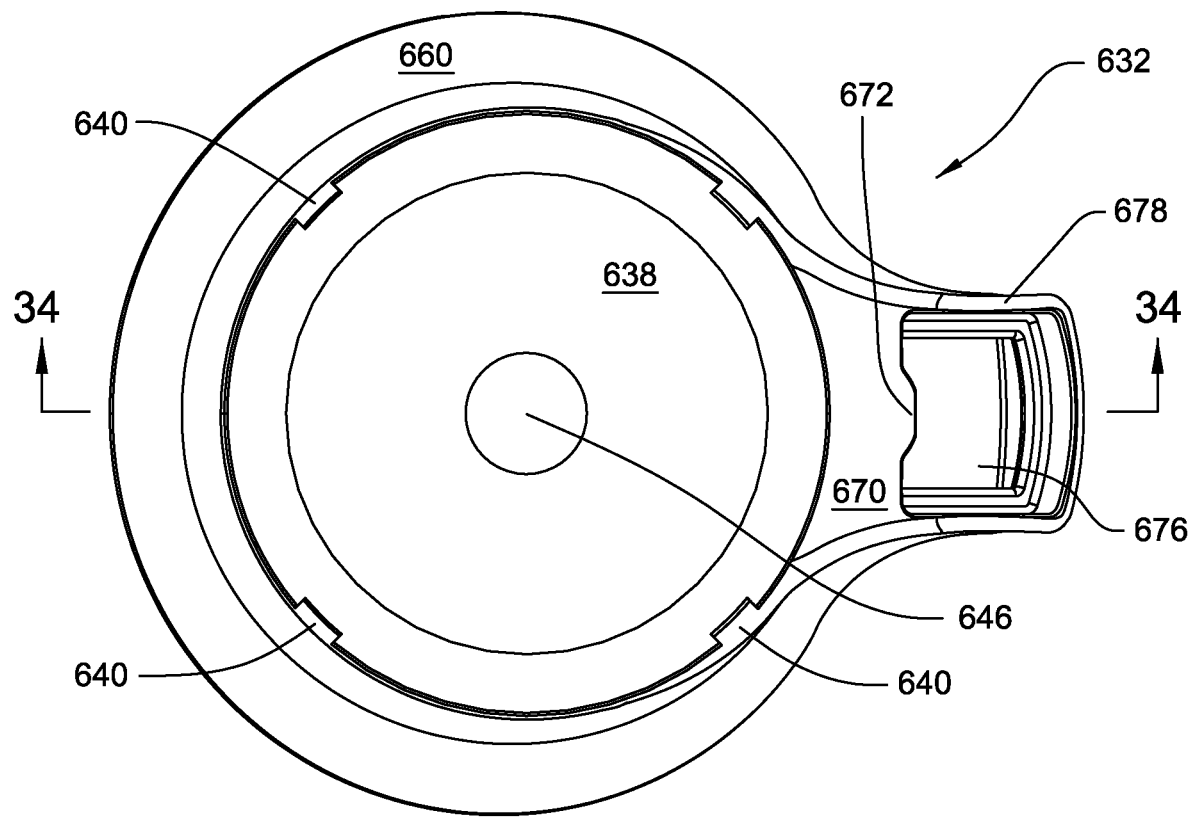
FIG. 33 is a top plan view of the base of the alternative cleaning head of FIG. 32.

Cleaning head base 632 can be formed from the same material from which the shells 192 and 194 of head 56 are formed. Alternatively, if cleaning head 630 is a use-once unit, base 632 may be formed from a sterilizable plastic such as a polycarbonate plastic. As best seen in FIGS. 33 and 34, base 632 is formed to have a cylindrical foot 638 dimensioned to seat on base unit surface 76. Foot 638 has an outer diameter that allows the foot to be slip fitted within the circular void space defined by the base unit lip 78. Four equiangularly spaced notches 640 extend upwardly from the bottom of the foot 638 around the outer perimeter of the foot. Notches receive pedestal teeth 84 when the cleaning head 630 is seated on the base unit 52. In the illustrated version of the invention, a groove 642 extends inwardly around the circumferential outer surface of the foot 638. Foot 638 is further formed to have two diametrically opposed notches 644 (one shown in FIG. 32) that extend inwardly from the outer circumferential surface of the foot. Notches 644 intersect groove 642. Each notch 644 is dimensioned to receive a separate one fingers 88 integral with the base unit retention arms 86. Base foot 638 also has a through hole 646 that extends top-to-bottom through the foot. Hole 646 is centered along the top to bottom longitudinal axis of the foot 638. Hole 646 is dimensioned to allow the base unit spindle head 108 freely move therein.

While not illustrated, it should be understood that RFID 270 and coil 271 (FIG. 5) are embedded in the foot 638 of cleaning head base 632. The data in RFID 270 are used by control console 66 to regulate the operation of the system base unit 52 when cleaning head 630 is attached.

Base 632 is further formed to have a multi-section ring 647 that extends upwardly from the outer perimeter of foot 638. The ring has a lower section, section 650, with a relatively thick cross sectional width. The ring has an upper section, section 652, with a narrower cross sectional width. Ring 647 is shaped so that the inner walls of the lower and upper sections 650 and 652, respectively, form a shell that defines a void space 654 above foot 638 of constant diameter. Void space 654 has a diameter that is at least 0.5 mm greater than that of brush 58. Thus, around the outer surface of the ring the ring upper section 652 is stepped inwardly from the lower section 650. The ring is of sufficient height so that void space 654 is able to receive all of the brush; both the substrate 260 and the bristles 268. The ring is further formed to have a flange 656 that projects radially outwardly from the top of the upper section 652. While not called out, it can be seen in FIG. 34 that the outer surface of the flange is outwardly tapered.

Cleaning head base 632 is further formed to have a lip 660 that extends substantially circumferentially around and above the ring. Lip 660 is formed to have a horizontal section 662 that extends radially away from the top of the ring lower section 650. Lip 660 also has a vertical section 664 integral with the outer end of the horizontal section 662. More particularly, the lip 660 is formed so that vertical section 664 extends both outwardly and upwardly away from the horizontal section. In many versions of the invention, including the illustrated version, lip 660 is formed so that the top edge of the vertical section 664 is located above the top of the ring upper section 652.

The cleaning head base 632 is further formed to have a spout 668. The spout 668 includes a finger 670 that extends radially and upwardly from an arcuate section of the ring lower section 650. The face of this finger 670 is flush with the adjacent arcuate step between the ring upper and lower sections 652 and 650, respectively. Finger 670 is formed with a tip 672 that extends radially outwardly beyond the portion of the finger on either side of the tip. Spout 668 also has a three-wall chute 678 that extends radially beyond finger 672. The walls that form the chute 678, two opposed side walls as well as a wall between the side walls are extensions of the lip vertical section 664 that are extend vertically upwardly more than the vertical section itself. Collectively, the outer end of the spout finger 670 and the adjacent though spaced away chute walls defining an opening 676 through the spout 668. In the illustrated version of the invention a three-sided lip 680 extends inwardly from the inner faces of the chute walls into the opening 676. Opening 676 is dimensioned to allow the seating thereon of mill head feed sleeve 306.

While not identified, it is observed from FIG. 32 that the upwardly directed portion of the cap lip 660 that leads to spout 668 is recessed relative to the adjacent surface of the lip 660.

Figure 36:
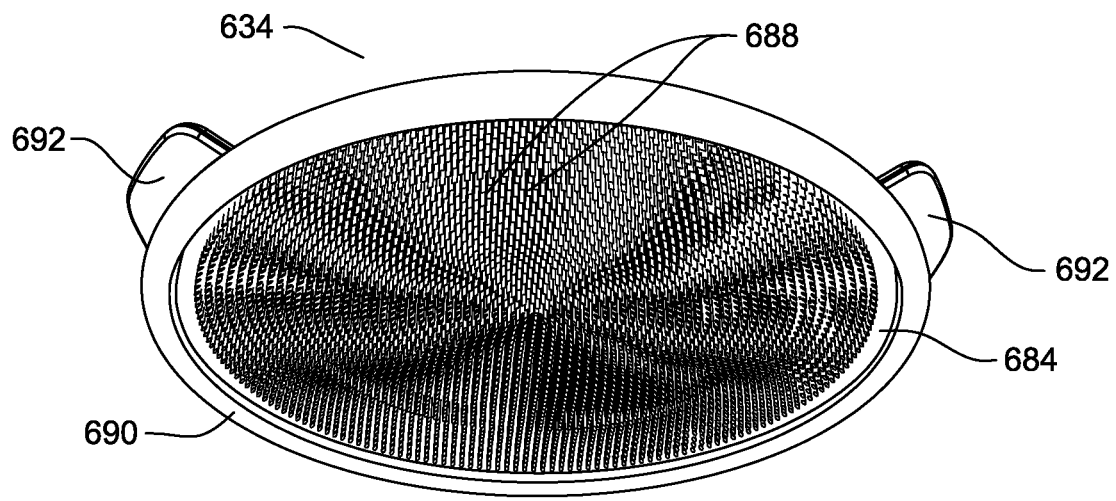
FIG. 36 is a perspective view of the bottom of the cap of the cleaning head of FIG. 32.
Figure 35:
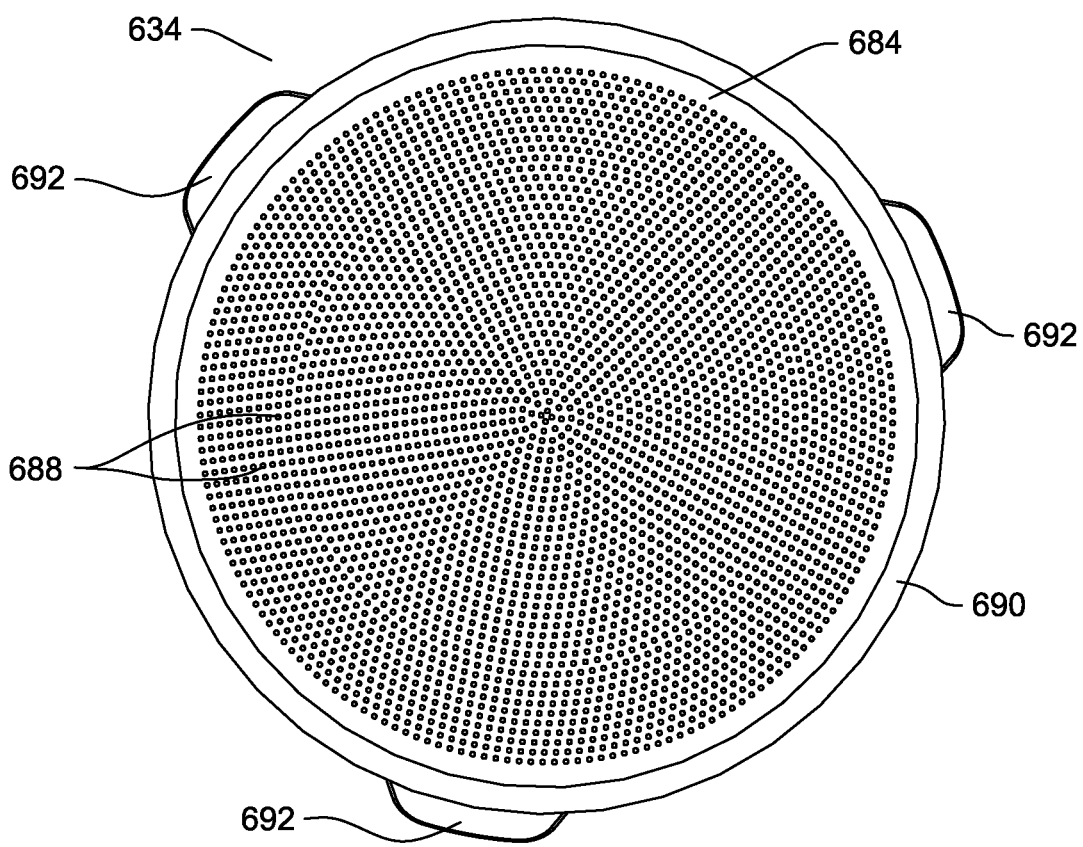
FIG. 35 is a bottom plan view of the cap of the cleaning head of FIG. 32.

The cap 634 of cleaning head 630 is formed from a flexible material such as a thermoplastic resin. The cap 634, shown best in FIGS. 32, 35 and 36 has a ring shaped rim 684. A concavo-convex dome 686 extends inwardly from the inner edge of the rim 684 and forms the center of the cap 634. The cap 634 is shaped so that the dome 686 extends upwardly away from the outer surface of rim, away from the outer surface of the underlying brush 58. Bristles 688, also part of cap 634, extend downwardly from the surface of the dome 686 directed towards brush 58.

A C-shaped lip 690 extends outwardly from the outer perimeter of the cap rim 684. One end of the lip 690 is contiguous with the outer edge of the rim 684. The cap 634 is shaped so that the lip 690 curves under the side of the rim that faces base 632. The cap 634 is formed so that the lip 690 can snap fit over flange 656 integral with base 632. Cap 634 is further formed to have a number of flexible tabs 692. Tabs 692 project radially and upwardly away from the outer surface of the cap lip 690 adjacent where the lip starts to curve under the rim 684. Tabs 692 serve as finger holds for stretching the cap over and removing the cap from the base ring upper section 652.

Cleaning head 630 of this invention is used by seating the brush 58 (or brush 602) in the base void space 654. The bone stock to be cleaned and milled is placed on brush bristles 268. Cap 634 is snap fitted over the base ring upper section 652. The cleaning head 630 is then fitted and secured to the base unit 52.

The base unit motor 54 is actuated as previously described in order to actuate the brush 58. During the time the brush 58 is rotated, the individual responsible for the cleaning process may press down on the cap dome 686. This action presses the caps bristles 688 against the bone. The bone is therefore compressed between both the brush bristles 268 and the cap bristles 688. The rotation of the brush 58 rotates the bone stock against both sets of bristles 268 and 688 to result in the striping of ligaments and other debris away from the bone.

Figure 37:
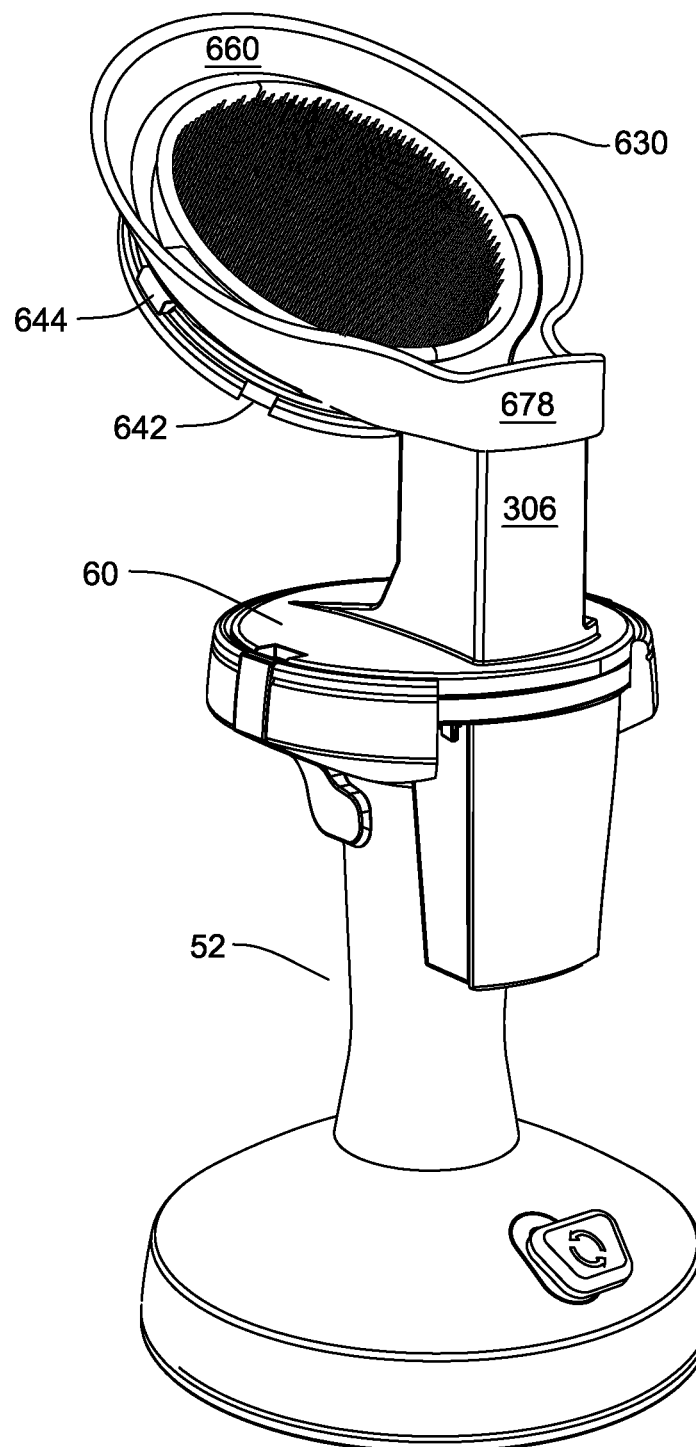
FIG. 37 depicts how the cleaning head of FIG. 32 is mated to the complementary mill head to facilitate the transfer of cleaned bone stock from the cleaning head to the mill head.

Once the bone is cleaned, the cleaning head 630, possibly with cap 634 still attached, is removed from the base unit 52. Mill head 60 is attached to the base unit 52. As seen in FIG. 37, the cleaning head 630 is then positioned so that chute 678 extends on the top of the mill head feed sleeve 306. The underside of lip 680 that surrounds spout opening 676 abuts the top edge surfaces of the feed sleeve 306. This lip-to-sleeve contact prevents from the cleaning head 630 from sliding down the mill head feed sleeve 306

The cleaning cap 634 is removed from the rest of the head 630. The presence of lip 660, which flares outwardly, prevents the cleaned bone stock from falling out of the base 632. Assume the bone stock passes inspection, a hand held instrument, such as forceps, are used to guide the cleaned bone stock off the brush 58 through the spout 668 and into the feed sleeve 306. During this process, both lip 660 and the walls of chute 678 prevent the bone stock from falling out of the cleaning head base 632.

In the described version of the invention, once the bone is transferred into the feed sleeve 306, plunger 307 can then be fitted into the feed sleeve without first having to remove cleaning head 630.

Cleaning head 630 and mill head 60 of this embodiment of the system of this invention do more than, respectively, clean and mill the bone stock. These components are designed to be coupled to each between the cleaning and milling processes. In the described version of the invention this mating occurs without having to provide supplemental components such as a set screws or ball pins with moving components. This component mating minimizes the extent the cleaned bone stock needs to be handled before it is transferred to the mill head 60. This simplifies the transfer of the bone stock to the mill head and reduces the likelihood that, during the transfer process, the bone stock will be inadvertently mishandled.

Lip 660 and chute 668 of cleaning head 630 do more than function as structural members that prevent the bone stock from inadvertently fall out of the head base 632. The lip 660 and chute 668 function as features of the base 632 an individual can hold when handling the base. These features are both spaced away from the brush 58. Thus, an individual by holding onto either the base lip 660 or chute 668 can handle the base while having his/her fingers spaced from the brush 58. This reduces the likelihood that the individual may inadvertently touch the brush 58 and the possible problems caused by such contact.

X. Third Alternative Cleaning Head

Referring to FIGS. 38-47, a third alternative cleaning head 700 is shown. The cleaning head 700 comprises a base 702. A shell 704 is mounted to the base 702. The shell 704 defines a void space 706 for receiving the bone to be cleaned. A cap 707, (shown only in FIG. 39,) is removably mounted on top of the shell 704 to enclose the void space 706. The base 702, shell 704, and cap 707 can be formed from the same material from which the shells 192 and 194 of head 56 are formed. Alternatively, if cleaning head 700 is a use-once unit, base 702, shell 704, and cap 707 may be formed from a sterilizable plastic such as a polycarbonate plastic.

Figure 38:
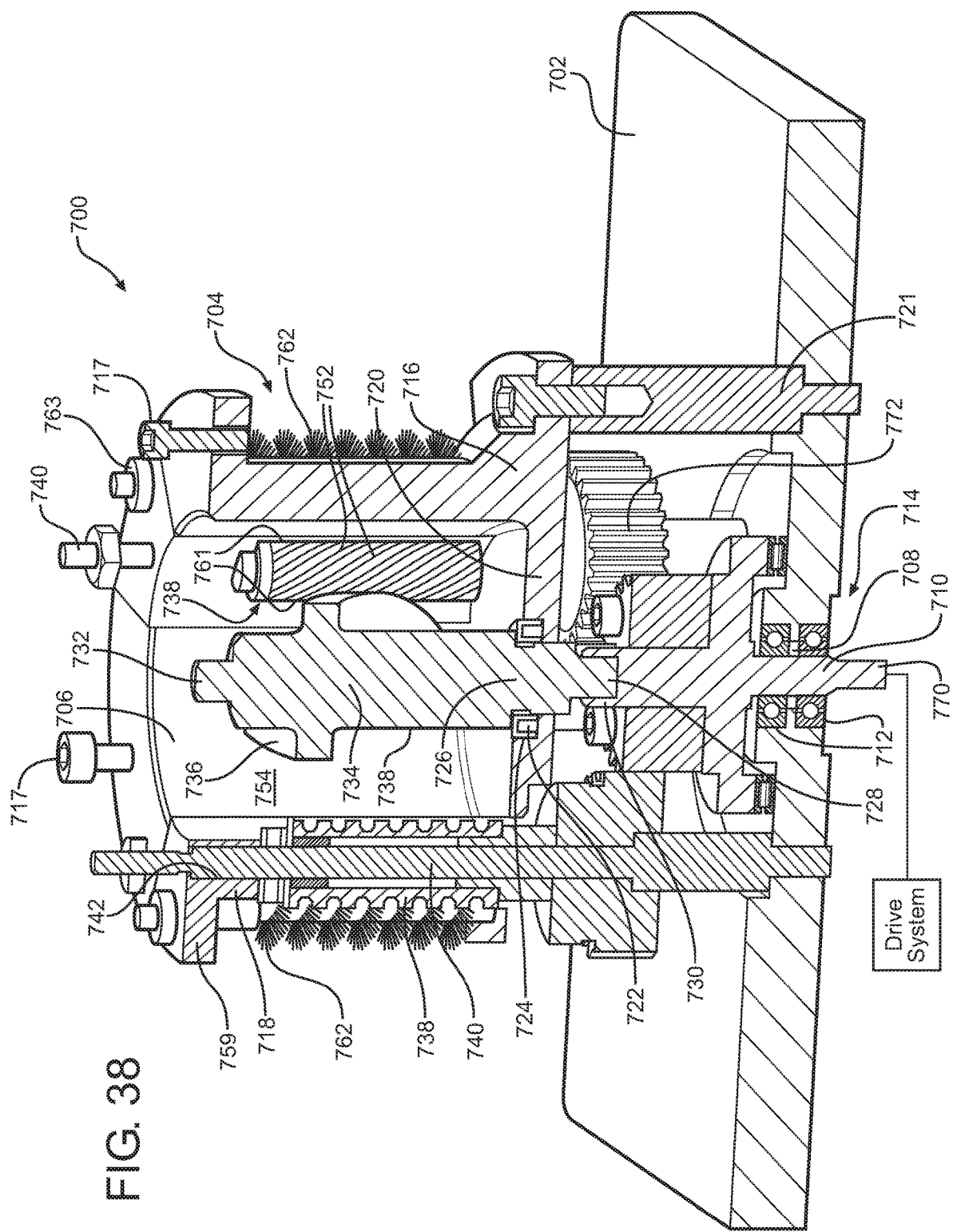
FIG. 38 is a cross-sectional perspective view of a third alternative cleaning head of this invention comprising a plurality of rotating fluted screws and a central agitator.
Figure 39:
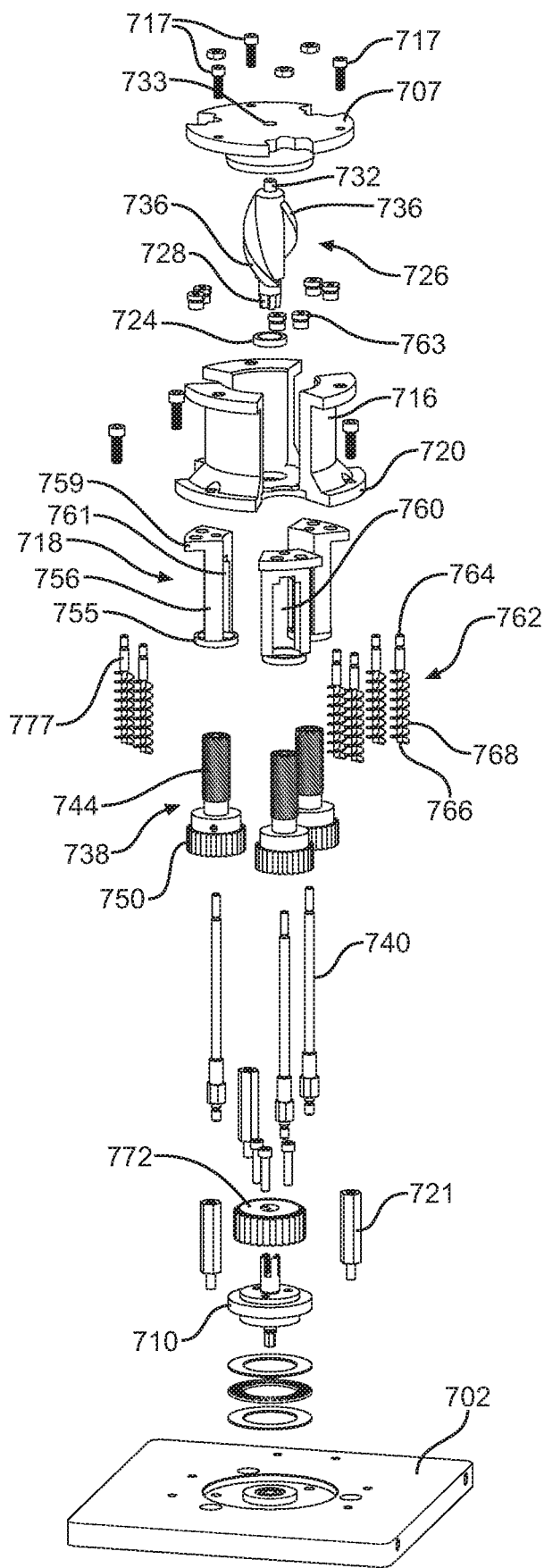
FIG. 39 is an exploded view of the alternative cleaning head of FIG. 38.

The base 702 is shown in FIGS. 38 and 39 as being rectangular in shape without any features for engaging the base unit 52. Accordingly, the cleaning head 700 may be a stand-alone unit for cleaning bone in which the base 702 is simply attached to a separate drive system (shown but not numbered). However, in other embodiments the base 702 has an outer diameter that allows the base 702 to be slip fitted within the circular void space defined by the base unit lip 78. As a result, the cleaning head 700 can be operated by the base unit 52. In this case, like the second alternative cleaning head 630, the base 702 is circular in shape (not shown) and four equiangularly spaced notches (not shown) extend upwardly from the bottom of the base 702 around the outer perimeter of the base 702. The notches receive the pedestal teeth 84 when the cleaning head 700 is seated on the base unit 52. A groove (not shown), like groove 642, extends inwardly around the circumferential outer surface of the base 702. Base 702 has two diametrically opposed notches (not shown), like notches 644 (one shown in FIG. 32) that extend inwardly from the outer circumferential surface of the base 702. Each notch being dimensioned to receive a separate one of the fingers 88 integral with the base unit retention arms 86.

Referring back to the embodiment of FIG. 38, the base 702 has a through hole 708 that extends top-to-bottom through the base 702. The hole 708 is centered along the top to bottom longitudinal axis of the base 702. The hole 708 is occupied by a spindle 710. The spindle 710 forms part of a drive assembly 714 of the cleaning head 700. The spindle 710 is rotatably supported by bearings 712 mounted to the base 702. A needle bearing assembly, shown in exploded view, is disposed between base 702 and the overlying surface of the spindle 710. The needle bearing assembly absorbs the thrust load of the spindle and the attached components. In alternative embodiments in which the cleaning head 700 is operated by the base unit 52, the spindle 710 is not present and the hole 708 is dimensioned to allow the base unit spindle head 108 to freely move therein and engage the cleaning head 700.

Referring to FIGS. 38 and 39, the shell 704 includes a shell base 716 to which a plurality of shaving blocks 718 are mounted. Alternatively, the shell 704 may be formed in one-piece with the shaving blocks 718 being integrated with the shell base 716. The cap 707 is mounted to the shell base 716 by a plurality of fasteners 717, (seen only FIG. 39). Alternatively, the cap 707 may be releasably locked to the shell base 716 by locking features (not shown) or the cap 707 may be simply fitted on top of the shell 704 temporarily during bone cleaning. The shell base 716 includes a bottom 720 that is generally circular in shape. A plurality of spacers 721 space the bottom 720 from the base 702. The bottom 720 defines a through bore 722 that is generally centrally located within the bottom 720. A bushing 724 is mounted to the bottom 720 in the through bore 722 and rotatably supports an agitator 726.

The agitator 726 includes a cross-shaped first end 728 that engages a correspondingly cross-shaped grooved end 730 of the spindle 710. The ends 728 and 730 mate such that rotation of the spindle 710 results in direct rotation of the agitator 726. The agitator 726 extends from the first end 728 disposed beneath the bottom 720, through the through bore 722 and upwardly into the void space 706 to a second free end 732. When the cap 707 is attached, the agitator second end 732 is seated in closed end bore formed in cap 707. Cap 707 thus supports the agitator second end 732.

The agitator 726 is generally cylindrical in shape and is elongated between its ends 728, 732. The agitator 726 includes a stem 734 disposed about a rotational axis and a pair of fins 736 extending radially outwardly from the stem 734. The fins 736 extend helically about the rotational axis from the first end 728 toward the second end 732. When bone is placed in the void space 706 the fins 736 rotate to pick up and tumble the bone and press the bone outwardly away from the rotational axis of the agitator 726. The fins 736 may be tapered from the first end 728 toward the second end 732 such that the fins 736 increase in radially outward dimension from the stem 734 as the agitator 726 extends from the second end 732 toward the first end 728.

Cleaning elements 738 in the form of fluted screws 738 clean soft tissue from the bone placed in the void space 706. Axles 740 rotatably support the fluted screws 738 in the shaving blocks 718. The axles 740 are supported and fixed at a first end in the base 702 and extend upwardly from the base 702 to a second end. The second end is disposed in a top opening 742 in a top plate 759 of the shaving blocks 718.

Figure 41:
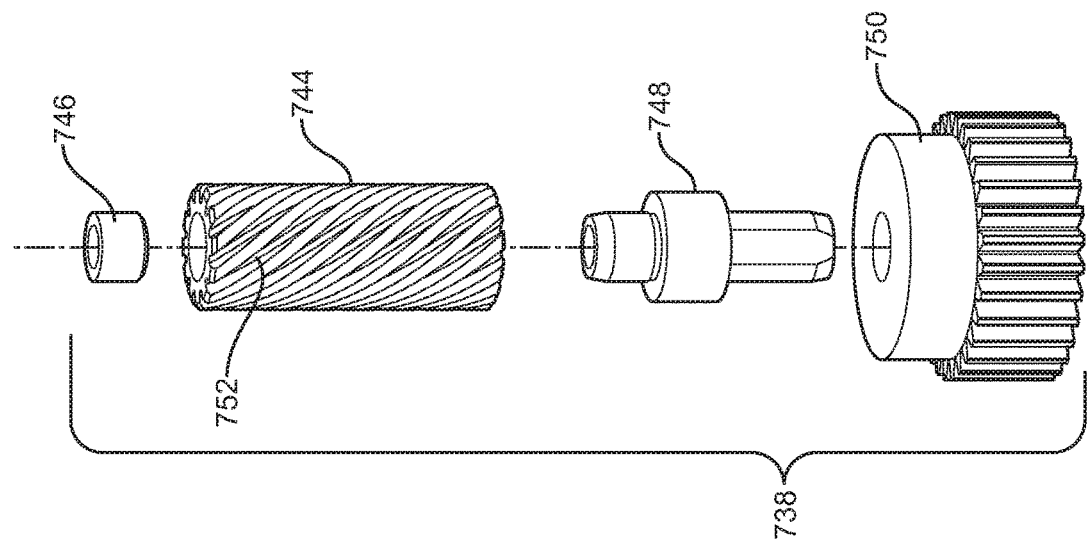
FIG. 41 is an exploded view of the rotating fluted screw of FIG. 40.
Figure 40:
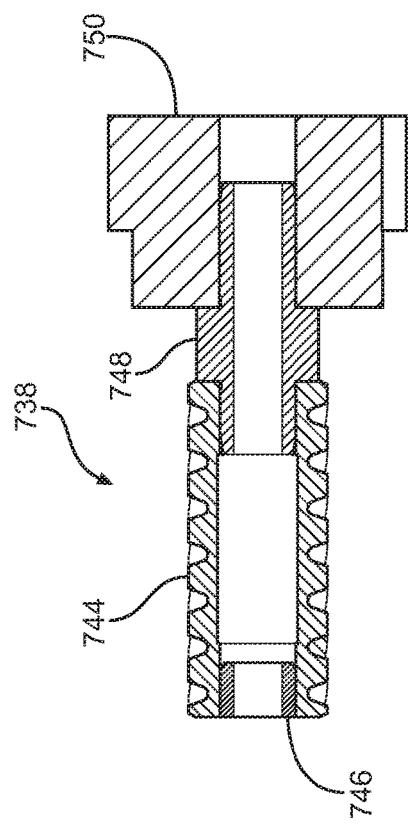
FIG. 40 is cross-sectional view of one of the rotating fluted screws of the alternative cleaning head of FIG. 39.
Figure 43:
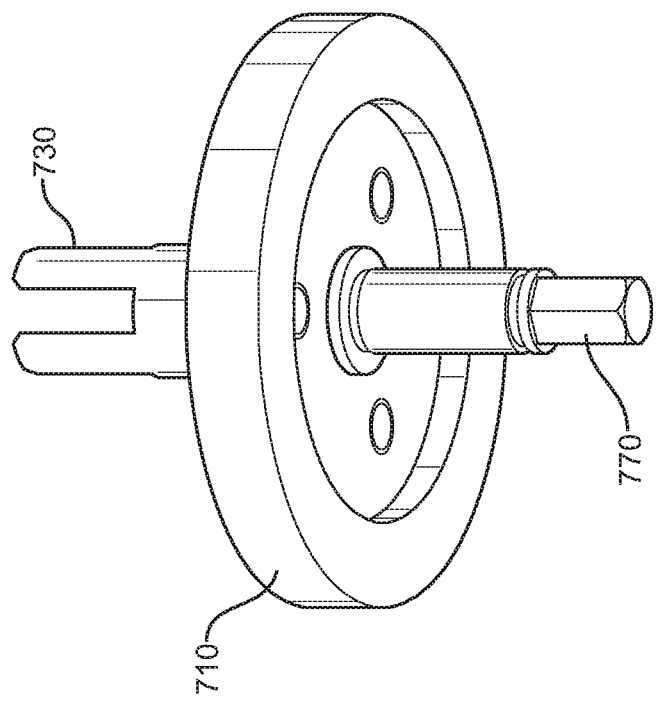
FIGS. 42 and 43 are top and bottom perspective views of the spindle used to drive the rotating fluted screws of the alternative cleaning head of FIG. 38.
Figure 42:
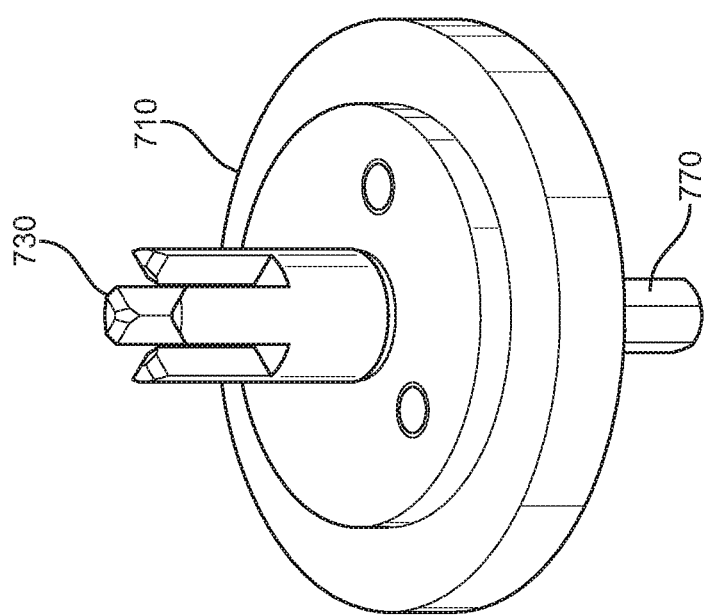
Figure 44:
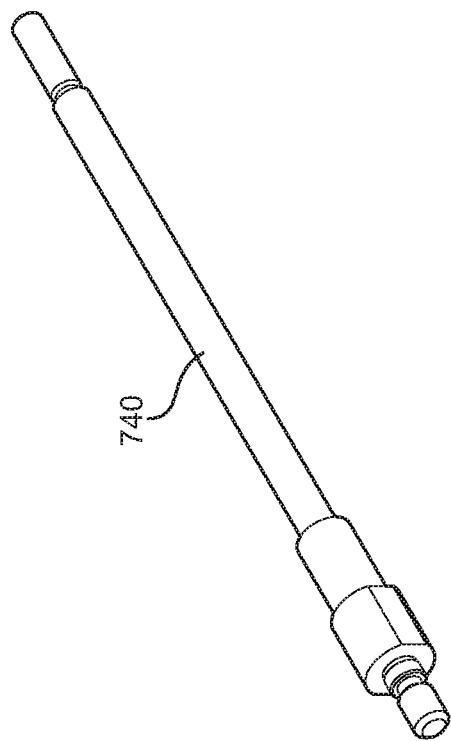
FIG. 44 is a perspective view of an axle on which the rotating fluted screws rotate in the cleaning head of FIG. 38.
Figure 46:
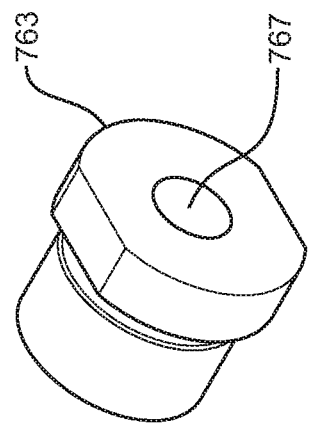
FIG. 46 is a perspective view of a plug for the alternative cleaning head of FIG. 38.

Referring to FIGS. 40 and 41, each of the fluted screws 738 include a sleeve 744, a pair of couplings 746, 748 for press-fitting into opposing ends of the sleeve 744 to rotate about the axle 740, and a pinion gear 750 for engaging the drive assembly 714 of the cleaning head 700. Each sleeve 744 has an axially extending through bore, (not identified). Each sleeve 744 is further shaped to have a plurality of flutes 752 that extend helically around the outer surface of the sleeve. Flutes are formed with adjacent surfaces that meet at defined edges 761 discussed below. This flute geometry facilitates gripping and tearing of soft tissue from the bone as part of the cleaning process. As shown in FIG. 39, each fluted screw 738 is rotatably mounted to a separate one of the shaving blocks 718. Sleeves 744 are preferably formed of stainless steel.

Figure 45:
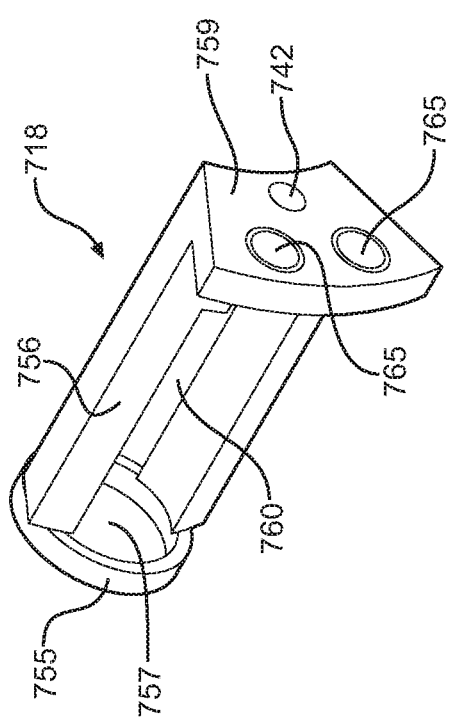
FIG. 45 is a perspective view of shaving block of the alternative cleaning head of FIG. 38.
Figure 47:
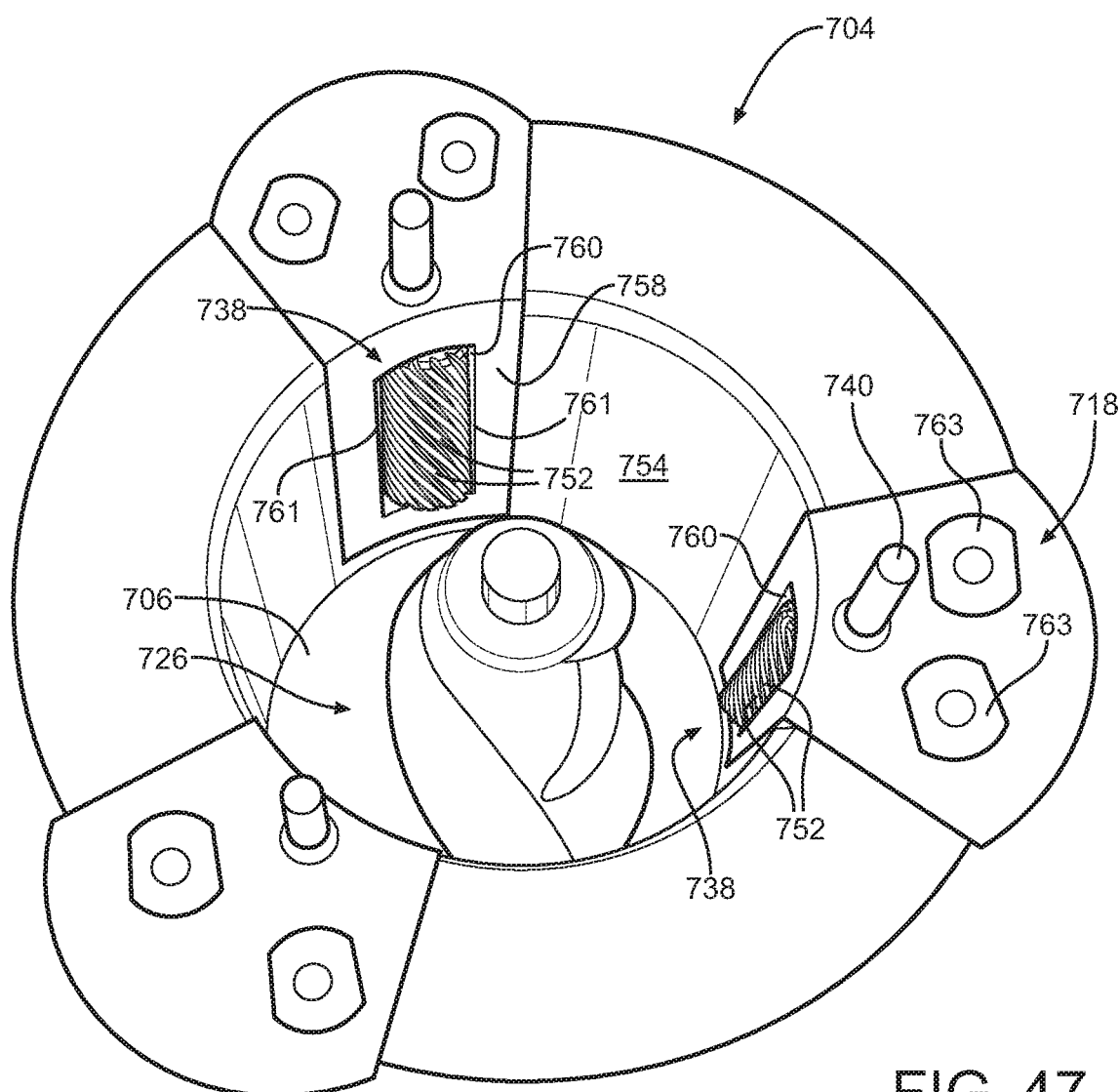
FIG. 47 is a partial perspective view illustrating the void space and shaving block with rotating flute screw of the alternative cleaning head of FIG. 38.

Referring to FIGS. 45 and 47, the shaving blocks 718 are preferably formed of stainless steel. The shaving blocks 718 are mounted adjacent the shell base 716 to form part of a generally cylindrical inner surface 754 of the shell 704. The inner surface 754 further defines the void space 706. Bone is compressed against the inner surface 754 by the agitator 726. Each shaving block 718 includes a ring shaped collar 755. The collar 755 defines an opening 757 that receives the associated fluted screw 738. A front post 756 extends upwardly from the collar 755 to the top plate 759. Top plate is longitudinally supported by a thrust bearing (not illustrated). Post 756 has a front surface 758 forming part of the inner surface 754. An elongated space 760 is defined in the front post 756 to receive the fluted screw 738. The fluted screw 738 rotates in the elongated space 760 in the front post 756. A portion of the sleeve 744 extends radially inwardly toward the agitator 726 a distance away from the front surface 758 to grip soft tissue attached to bone disposed in the void space 706.

Each sleeve flute 752 is shaped to define a pair of cutting edges 761 disposed on opposing sides of the elongated space 760 (see FIG. 47). These cutting edges 761 are sharp enough to cut soft tissue that the associated sleeve 744 grips or captures during rotation. Each sleeve 744 engages the soft tissue still attached to bone and impinge that soft tissue against the cutting edges 761 during rotation to cut the soft tissue away from the bone. The agitator 726 forces the bone with soft tissue attached thereto toward the sleeves 744 to facilitate gripping of the soft tissue by the fluted screws 738 and corresponding cutting of the soft tissue by the cutting edges 761. Fluted sleeves 744 also separately act to cut the soft tissue from the bone although to a limited extent.

A plurality of wire brushes 762 are fixed to each shaving block 718 to clean the associated fluted screws 738. In the embodiment shown two wire brushes 762 are attached to each shaving block 718. Each brush 762 has a first end 764 fixed to the top plate 759 of the shaving block 718 and a second end 766 disposed adjacent the base collar 755. A plug 763 (see FIG. 46) is inserted into an opening 765 in the top plate 759 of the shaving block 718. The first end 764 of the wire brush is press fit into a bore 767 in the plug 763. The plug 763 is press fit into the opening 765 and snugly holds the first end in the opening 765 so that the brushes 762 remain fixed relative to the rotating fluted screws 738.

Referring to FIG. 39, each of the wire brushes 762 includes an elongated cylindrically shaped substrate 777 formed of metal or a sterilizable plastic such as a glass-filled nylon. The bristles 768 are preferably made of metal such as stainless steel. The bristles 768 clean out soft tissue trapped in the flutes 752 of the fluted screws 738 as the fluted screws 738 are rotating in the void space 706. Accordingly, the bristles 768 are positioned such that they penetrate into the flutes 752 of the fluted screws 738. The bristles 768 remain fixed to the shell 704 while the rotating flute screws 738 rotate relative to the shell 704 and the fixed bristles 768.

As previously discussed, the hole 708 extending through the base 702 is occupied by spindle 710. The spindle 710 extends from the first end 730 that engages the first end 728 of the agitator 726 to a second end 770 having features (such as a square shaft configuration) for mating with a drive system such as a drive motor (shown but not numbered). In the embodiment shown, the drive assembly 714 further includes a pinion gear 772 that is fixedly mounted to the spindle 710. The gear 772 is adapted to mate with the gears 750 of the fluted screws 738 to transmit power to the screws 738. This causes the fluted screws 738 to rotate when the drive system is actuated. Simultaneously, the spindle 710 also transfers power from the drive system to the agitator 726 so as to rotate the agitator.

Alternatively, the first end 728 of the agitator 726 and the gear 772 could be configured to engage and be rotatably fixed to the base unit spindle head 108 via the alignment pin 110 and teeth 112 so as to be operated by the base unit 52.

In the embodiment shown, the gear ratio of the gear 772 to gears 750 is 1:1. In alternative embodiments, different gear ratios could be employed such as 1:2 or 1:3 and vice versa depending on the particular desired relative rotational speeds of the agitator 726 and fluted screws 738.

During operation, uncleaned bone is first placed in the void space 706 for cleaning and the cap 707 is then placed to cover the void space 706. The uncleaned bone includes soft tissue attached thereto that requires removal prior to processing by the mill head 60. The drive system or base unit 52 (if the cleaning head 700 is mounted to the base unit 52) is then actuated to start rotation of the drive assembly and simultaneous rotation of the agitator 726 and fluted screws 738. The agitator 726 then acts to tumble the bone and forces the bone against the fluted screws 738. The fluted screws 738 grip soft tissue attached to the bone and cut the soft tissue away from the bone either by the nature of the flutes 752 on the fluted screws 738 or by impinging the soft tissue against the cutting edges 761 of the shaving blocks 718. The wire brushes 762 continuously act to clean the fluted screws 738 by removing material out from the flutes 752. Once the cleaning head 700 has sufficiently removed soft tissue from the bone, the cap 707 is removed and the cleaned bone is grabbed by forceps or other device for further processing. The cleaning head 700 may then be cleaned or discarded.

While not illustrated, it should be understood that RFID 270 and coil 271 (FIG. 5) may be embedded in the base 702 of cleaning head 700. The data in RFID 270 are used by control console 66 to regulate the operation of the system base unit 52 when cleaning head 700 is attached.

XI. Fourth Alternative Cleaning Head

Figure 48:
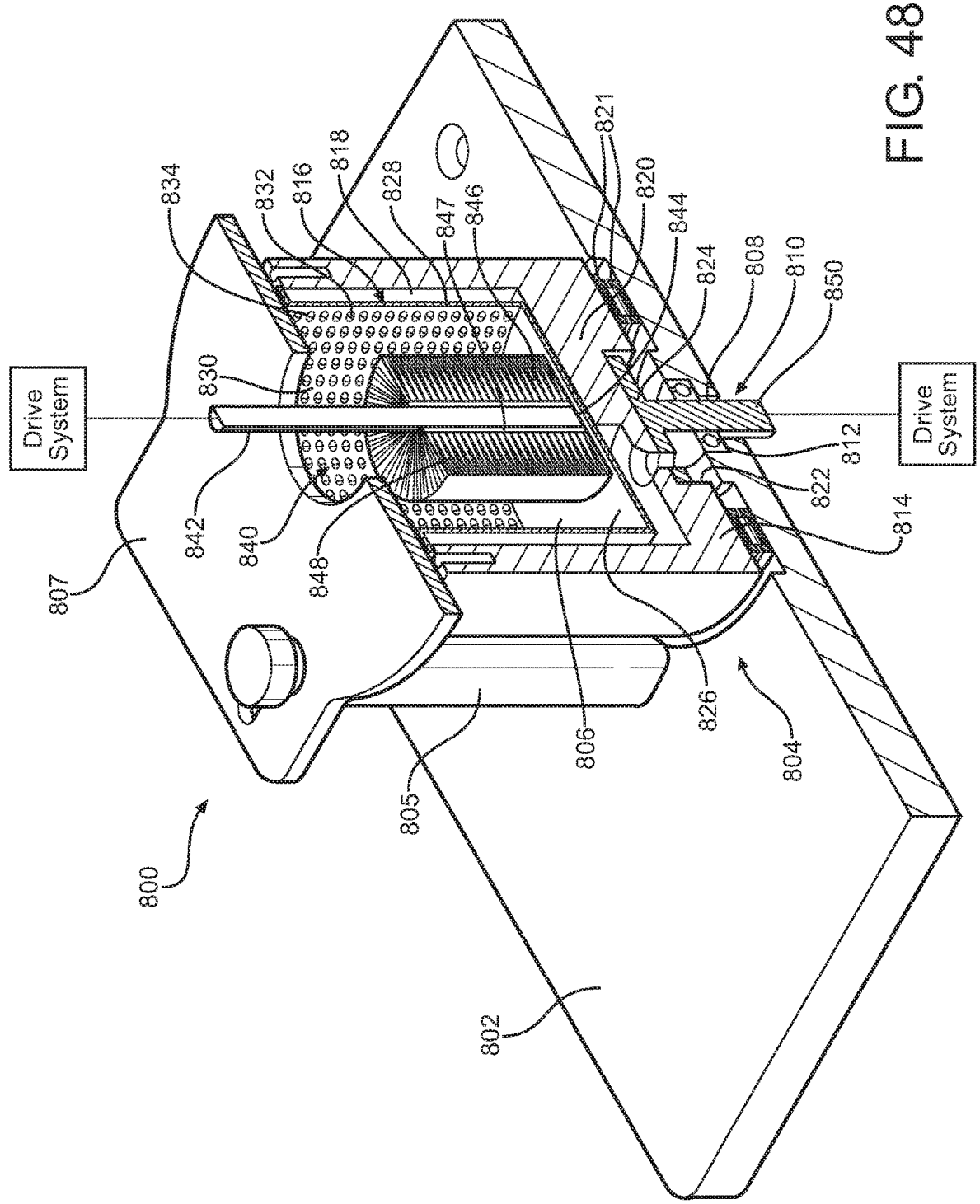
FIG. 48 is a cross-sectional perspective view of a fourth alternative cleaning head of this invention comprising a rotating inner basket and a rotating brush.
Figure 49:
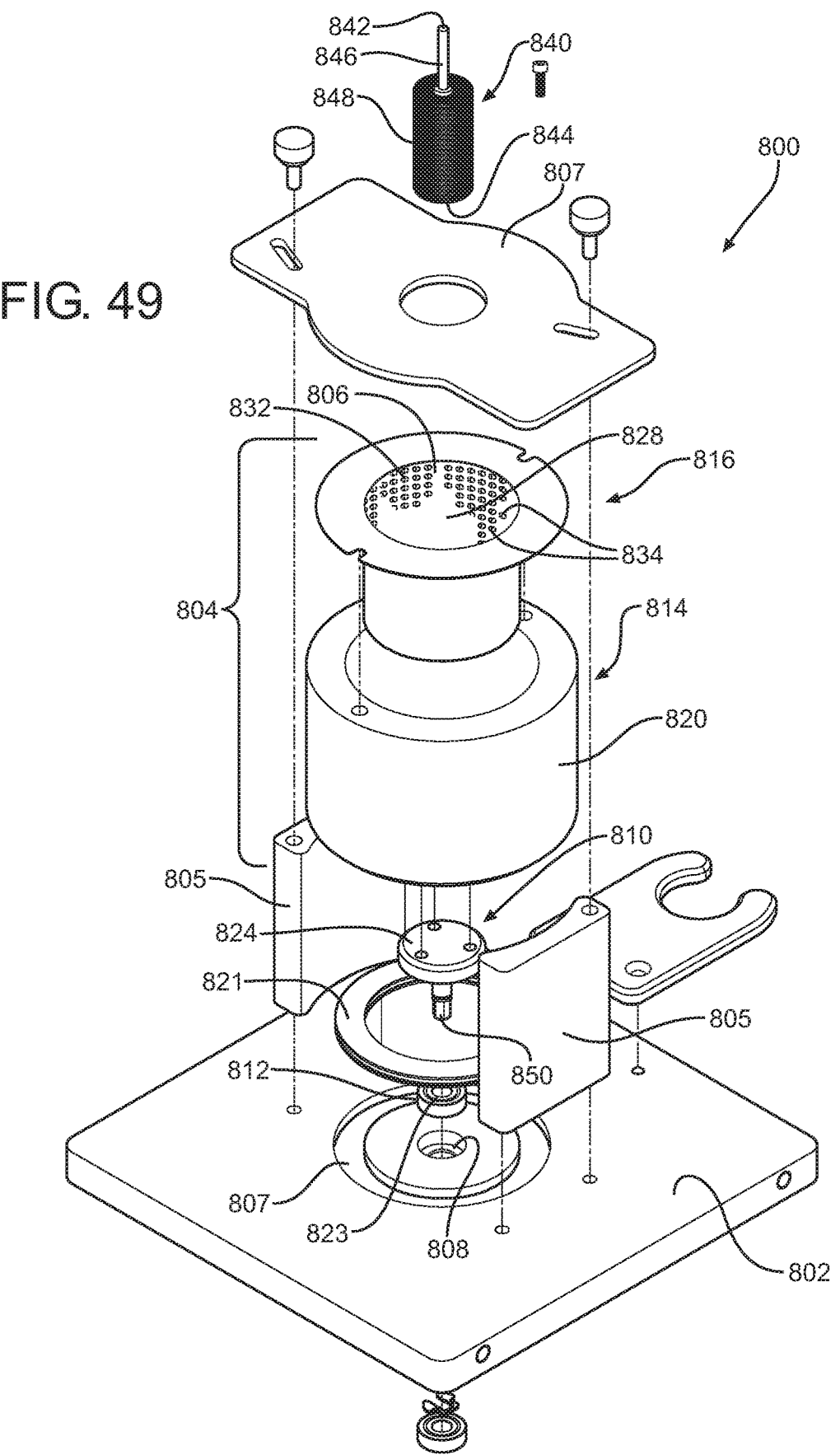
FIG. 49 is an exploded view of the alternative cleaning head of FIG. 48.

Referring to FIGS. 48 and 49, a fourth alternative cleaning head 800 is now described. Cleaning head 800 includes a base 802. A shell 804 is mounted to the base 802. The shell 804 defines a void space 806 for receiving the bone to be cleaned. A pair of shields 805 are fixed to the base 802 on opposing sides of the shell 804. A cap 807 is mounted to each of the shields 805 above the shell 804 to cover the void space 806. The base 802, shell 804, and cap 807 can be formed from the same material from which the shells 192 and 194 of head 56 are formed. Alternatively, if cleaning head 800 is a use-once unit, base 802, shell 804, and cap 807 may be formed from a sterilizable plastic such as a polycarbonate plastic.

The base 802 is shown in FIGS. 48 and 49 as being rectangular in shape without any features for engaging the base unit 52. Accordingly, the cleaning head 800 may be a stand-alone unit for cleaning bone in which the base 802 is simply attached to a separate drive system (shown but not numbered). However, in alternative embodiments, the cleaning head 800 is operated by the base unit 52. In these embodiments, the base 802 has an outer diameter that allows the base 802 to be slip fitted within the circular void space defined by the base unit lip 78. In this case, like the second alternative cleaning head 630, the base 802 is circular in shape and four equiangularly spaced notches (not shown)

extend upwardly from the bottom of the base 802 around the outer perimeter of the base 802. The notches receive the pedestal teeth 84 when the cleaning head 800 is seated on the base unit 52. A groove (not shown), like groove 642, extends inwardly around the circumferential outer surface of the base 802. Base 802 is further formed with two diametrically opposed notches (not shown), like notches 644 (one shown in FIG. 32) that extend inwardly from the outer circumferential surface of the base 802. Each notch being dimensioned to receive a separate one of the fingers 88 integral with the base unit retention arms 86.

Referring back to the embodiment of FIGS. 48 and 49, the base 802 has a through hole 808 that extends top-to-bottom through the base 802. The hole 808 is centered along the top to bottom longitudinal axis of the base 802. The hole 808 is occupied by a spindle 810. The spindle 810 forms part of a drive assembly of the cleaning head 800. The spindle 810 is rotatably supported in a bearing 812 mounted to the base 802. In the alternative embodiments in which the cleaning head 800 is operated by the base unit 52, the spindle 810 is not present and the hole 808 is dimensioned to allow the base unit spindle head 108 to freely move therein and engage the cleaning head 800.

Referring to FIG. 48, the shell 804 includes an outer basket 814 and an inner basket 816 spaced from the outer basket 814 to define a gap 818 therebetween. In the embodiment shown, the outer 814 and inner 816 baskets are fixed to one another and to the spindle 810 such that rotation of the spindle 810 results in rotation of both of the baskets 814, 816. Outer basket 814 has a bottom 820 with an annular cavity 822 defined therein for receiving a circular plate 824 of the spindle 810. The circular plate 824 is secured to the outer basket 814 with fasteners (not shown). The base 802 defines a pocket 807 for receiving the bottom 820 of the outer basket 814. A pair of washers 821 with roller bearings (not shown) disposed therebetween are seated in the pocket 807 between the base 802 and the outer basket 814 to rotatably support the outer basket 814 for rotation relative to the base 802. Shields 805 protect users from the rotating shell 804.

The inner basket 816 has a bottom plate 826. A tube-shaped sleeve 828 extending upwardly from plate 826. Sleeve 828 has an open end 830 through which the bone to be cleaned is deposited in the basket 816. Sleeve 828 includes a plurality of openings 832. Each opening 832 is defined by a raised, inwardly directed scallop (not illustrated). Each scallop, which is similar to mill element scallop 336, has a sharp edge, that defines the adjacent opening 832. Thus, the opening 832—defining scallops give the sleeve 828 a shape similar to that of a grater. Here, since the scallops are inwardly directed, towards the longitudinal axis of the basket, the inner wall of the sleeve 828 is the grating surface of the inner basket 816. The openings 832 are sized and configured to be small enough to prevent the bone from falling therethrough, but large enough to grasp or at least partially capture and temporarily hold the bone and tumble the bone about an inner surface 834 of the inner basket 816. The plate 826 may include similar openings in alternative embodiments, but is solid in the embodiment shown.

A cleaning element 840, in the form of a brush 840, is rotatably supported in the void space 806 for engaging the bone tumbling against the inner surface 834 of the inner basket 816. The brush 840 has a first end 842 disposed outside of the void space 806 and a second end 844 disposed inside the void space 806. The brush 840 includes an elongated cylindrically shaped substrate 846 formed of metal or a sterilizable plastic such as a glass-filled nylon. Bristles 848 are attached to the substrate 846 by an adhesive 847 such as an epoxy adhesive. In manufacture, adhesive 847 is initially applied over an outer cylindrical face of substrate 846. Before the adhesive cures, the bristles 848 are planted in the adhesive 847. The bristles 848 are preferably made of metal such as stainless steel. The bristles 848 grab and tear soft tissue from the bone while the bone is frictionally grabbed by the inner basket 816 via the openings 832. Soft tissue that is removed by the openings 832 is captured in the gap 818 between the outer 814 and inner 816 baskets. In FIG. 48 the brush 840 is shown generally centrally disposed in the void space 806 for rotating about a central axis. In other embodiments, the brush 840 is disposed about an axis offset from the central axis of the void space 806 and the brush 840 can likewise be disposed at an acute angle to the shell 804.

As previously discussed, the hole 808 extending through the base 802 is occupied by the spindle 810. The spindle 810 extends from the circular plate 824 to an end 850 having features (such as a square shaft configuration) for mating with a drive system such as a drive motor (shown but not numbered). In the embodiment shown, the spindle 810 is rotatably fixed to both the outer 814 and inner 816 baskets to transmit power from the drive system to the baskets 814, 816 thereby causing the baskets 814, 816 to rotate when the drive system is operational. Alternatively, the circular plate 824 could be configured to engage and be rotatably fixed to the base unit spindle head 108 via the alignment pin 110 and teeth 112. As a result, the cleaning head 800 could be operated by the base unit 52.

In the embodiment shown, a separate drive system (shown but not numbered) engages the first end 842 of the brush 840 to rotate the brush 840 in the void space 806. The separate drive system rotates the brush 840 in a direction opposite the direction of rotation of the baskets 814, 816. Alternatively, the brush 840 could rotate in the same direction as the baskets 814, 816, either at the same rotational speed or at different rotational speeds. This separate drive system could be a stationary head fixed to the base 802 above the void space 806 with a motor disposed in the stationary head above the void space 806.

Figure 49A:
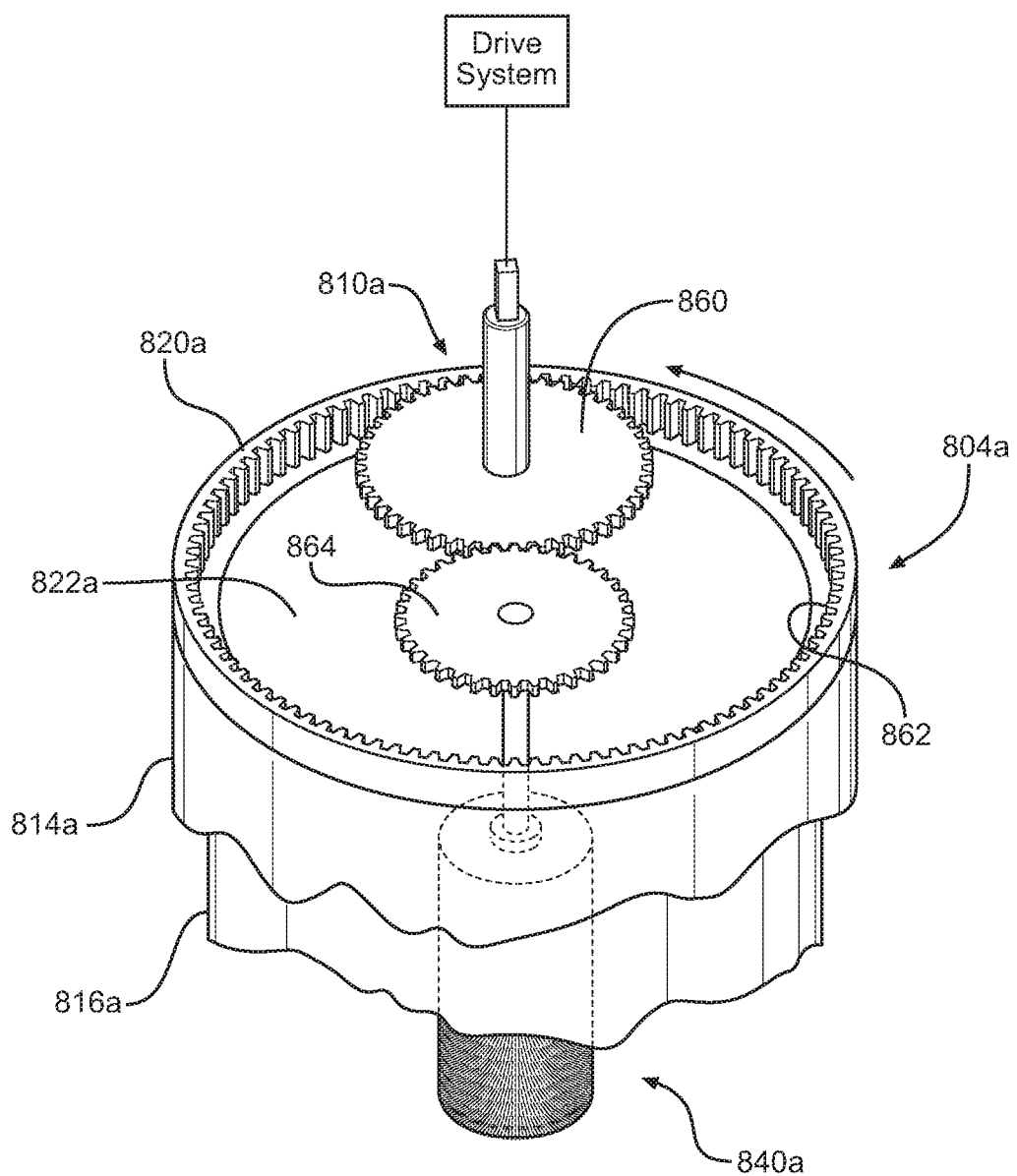
FIG. 49A is a partial perspective view an alternative gear train for the alternative cleaning head of FIG. 48.

In other embodiments the same drive system rotating the baskets 814, 816 also rotates the brush 840. Referring to FIG. 49A, in such an embodiment, the spindle 810a could be offset from the center of the shell 804a and include a pinion gear 860 that engages teeth 862 in the annular cavity 822a defined in the bottom wall 820a to rotate the outer 814a and inner 816a baskets. A separate pinion gear 864 is attached to the first end 842a of the brush 840a. Thus, when the spindle 810a rotates in a first direction, the outer 814a and inner 816a baskets also rotate in the first direction, while the brush 840a rotates in a second direction, opposite the first direction. Thus, the spindle 810a, gear 860, teeth 862, and gear 864 would form a drive assembly of the cleaning head 800. The gear ratio between the gears 860, 864 and teeth 862 are selected such that the rotational speed of the brush 840a is substantially faster than the rotationally speed of the baskets 814a, 816a. In some cases the rotational speed of the brush is 5,000 to 10,000 RPM and the rotational speed of the baskets 814a, 816a is less than 1000 RPM, often less than 500 rpms, and possible 100 rpms or less. Thus, the ratio of rotational speeds of the brush 840, 840a to the baskets 814, 814a, 816, 816a is from about 5:1 to about 100:1.

During operation, uncleaned bone is first placed in the void space 806 for cleaning and the cap 807 is then placed to cover the void space 806. The uncleaned bone includes soft tissue that requires removal prior to processing by the mill head 60. The drive system or base unit 52 (if the cleaning head 800 is mounted to the base unit 52) is then actuated to start rotation of the spindle 810, 810*a* and subsequent rotation of the shells 814, 814*a*, 816, 816*a*. If the brush 840*a* is connected to the spindle 810*a*, then rotation of the brush 840*a* is also actuated. Alternatively, the brush drive system is actuated simultaneously to rotate the brush 840 in a direction preferably opposite to the baskets 814, 814*a*, 816, 816*a*. The inner basket 816, 816*a* and the openings 832 in the inner basket 816, 816*a* operate to grab and tumble the bone. The bristles 848 of the brush 840, 840*a* grip and tear away soft tissue attached to the bone. Once the cleaning head 800 has sufficiently removed soft tissue from the bone, the cap 807 is removed and the cleaned bone is grabbed by forceps or other device for further processing. The cleaning head 800 may then be cleaned or discarded. In some cases only the inner basket 816, 816*a* and the brush 840, 840*a* is discarded while the remaining components are sterilized and reused.

While not illustrated, it should be understood that RFID 270 and coil 271 (FIG. 5) may be embedded in the base 802 of cleaning head 800.

XII. Fifth Alternative Cleaning Head

Figure 50:
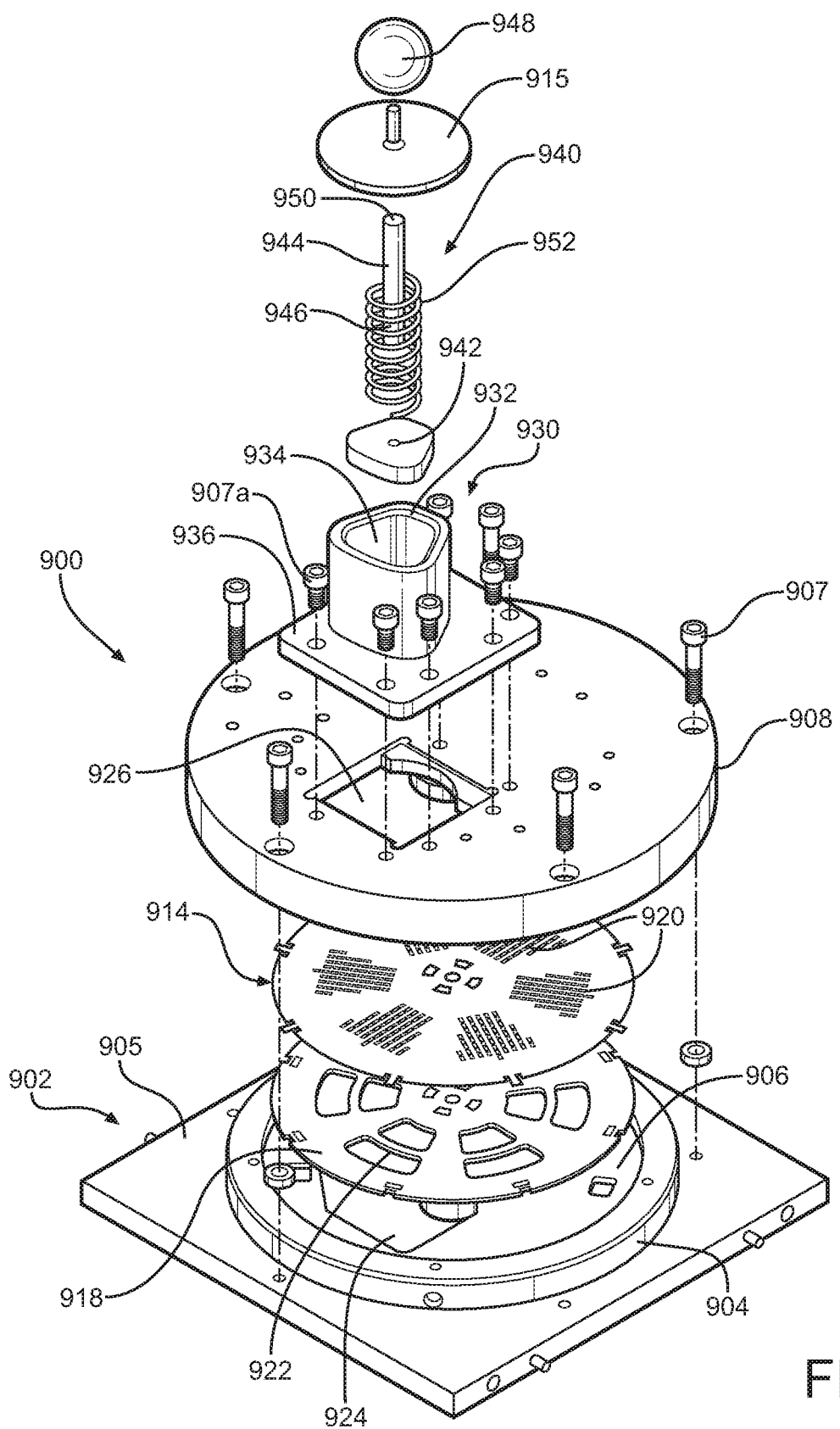
FIG. 50 is an exploded view of a fifth alternative cleaning head with a rotating grater and a plunger.
Figure 51:
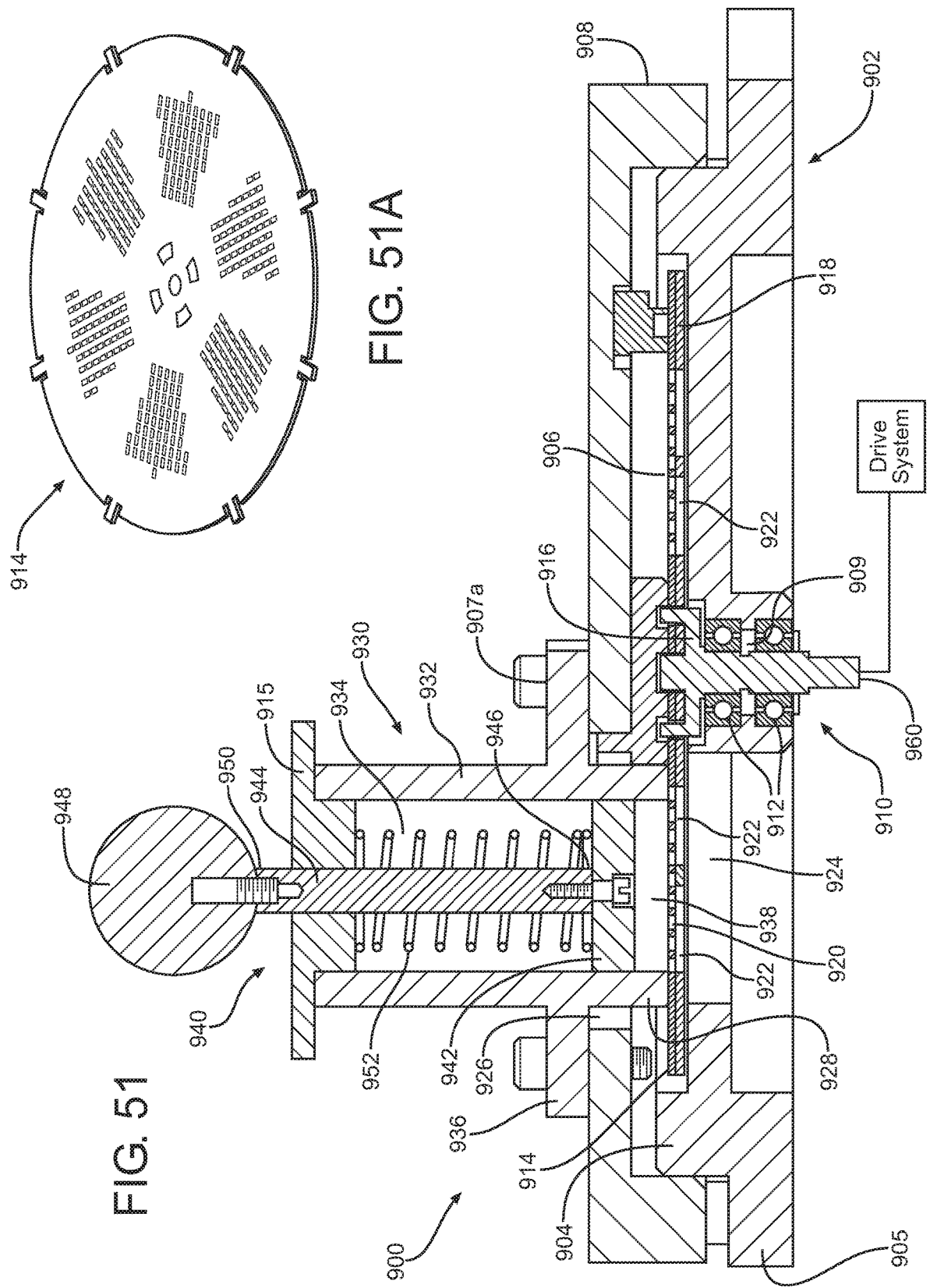
FIG. 51 is a cross-sectional view of the alternative cleaning head of FIG. 50.

Referring to FIGS. 50 and 51, a fifth alternative cleaning head 900 is now described. The cleaning head 900 comprises a base 902. A ring-shaped section 904 of the base 902 protrudes upwardly from a bottom section 905 of the base 902. A cavity 906 is defined radially inwardly from the protruding ring-shaped section 904. A shell 908 is mounted to the base 902 about the ring-shaped section 904 and above the cavity 906 using a plurality of fasteners 907. The base 902 and shell 908 can be formed from the same material from which the shells 192 and 194 of head 56 are formed. Alternatively, if cleaning head 900 is a use-once unit, base 902 and shell 908 may be formed from a sterilizable plastic such as a polycarbonate plastic.

The bottom section 905 of the base 902 is shown in FIGS. 50 and 51 as being rectangular in shape without any features for engaging the base unit 52. Accordingly, the cleaning head 900 may be a stand-alone unit for cleaning bone in which the base 902 is simply attached to a separate drive system (shown but not numbered). However, in other embodiments, the base 902 is attached to the base unit 52 for operation by the base unit 52. In this case, the base 902 has an outer diameter that allows the base 902 to be slip fitted within the circular void space defined by the base unit lip 78. Like the second alternative cleaning head 630, the base 902 is circular in shape and four equiangularly spaced notches (not shown) extend upwardly from the bottom of the base 902 around the outer perimeter of the base 902. The notches receive the pedestal teeth 84 when the cleaning head 900 is seated on the base unit 52. A groove (not shown), like groove 642, extends inwardly around the circumferential outer surface of the base 902. The base 902 is further formed to have two diametrically opposed notches (not shown), like notches 644 (one shown in FIG. 32) that extend inwardly from the outer circumferential surface of the base 902. Each notch being dimensioned to receive a separate one of the fingers 88 integral with the base unit retention arms 86.

Referring to FIG. 51, it can be seen that base 902 has a through hole 909 that extends top-to-bottom through the base 902. The hole 909 is centered along the top to bottom longitudinal axis of the base 902. The hole 909 is occupied by a spindle 910. The spindle is rotatably supported by bearings 912 mounted to the base 902. The spindle 910 forms part of the drive assembly of the cleaning head 900. In embodiments in which the cleaning head 900 is attached to the base unit 52, the spindle 910 is not present and the hole 909 is dimensioned to allow the base unit spindle head 108 to freely move therein and engage the cleaning head 900.

Cleaning head 900 includes a rotating grater disc 914 that functions as the cleaning element. Grater disc 914 is preferably formed of stainless steel. The grater 914 is disc shaped and has openings (not identified) around the center of the disc. The openings are positioned and shaped to engage the teeth integral with spindle plate 916, (teeth not identified). The engagement of disc 914, along with disc 918, to the spindle 910 causes the discs to rotate in unison with the spindle. A reinforcing disc 918 is disposed between the circular plate 916 and the grater disc 914. Grater disc 914 includes a plurality of openings 920 configured to file away soft tissue from bone. Reinforcing disc 918 includes larger openings 922 sized to allow filed off pieces of soft tissue to fall therethrough and out of the cleaning head 900 via a chute 924 in the base 902. Both discs 914, 918 are rotatably fixed to the spindle 910 to rotate with the spindle 910.

Grater disc openings 920, seen best in FIG. 51A, are arranged in arcuate groups on the disc 914 that are angularly spaced apart from each other. Thus, grater disc 914 has a number of arcuate sections that are free of openings 920. This increases the mechanical strength of the grater disc 914. The sections of the grater disc 914 in which openings 920 are formed extend over the sections of reinforcing disc 918 in which larger openings 922 are located. Thus, the grated off tissue falls through both grater disc openings 920 and reinforcing disc openings 922. The dimension(s) of the openings 920 are such that the soft tissue and debris present on the uncleaned bone is filed away and removed to clean the bone, but the bone itself is not damaged or diminished beyond a usable state. In other words, the openings 920 are sized and configured not to result in milling the bone like the mill element 62 of the mill head 60. In one embodiment, the openings 920 are rectangular in shape with a larger length than width (see FIG. 51A). In a more specific embodiment, the openings 920 are 0.39 cm (0.1 inches) or less long by 1.3 cm (0.5 inches) or less wide. Adjacent openings 920 are spaced in parallel columns and rows with approximately 0.2 cm (0.08 inches) or less between rows and 0.1 cm (0.04 inches) or less between columns.

While not identified, it is seen from FIG. 51A that grater disc 914 is formed with a number of arcuately spaced apart and radially outwardly extending tabs. During the assembly of disc 914, grater disc 914 is placed over reinforcing disc 918. The grater disc tabs are bent over and against the exposed face of the underlying reinforcing disc 918. The tabs hold discs 914 and 918 together as a unitary assembly.

An opening 926 is defined through the shell 908 above the grater disc 914. A plunger housing 930 is mounted to the shell 908 around the opening 926 using a plurality of fasteners 907*a*. Plunger housing 930 has a chute 932 that defines a plunger passage 934. One end of chute 932 extends into and around the outer perimeter of shell opening 930. A flange 936 extends outwardly from the chute above the end of the chute disposed against shell 908. The flange 936 is mounted to the shell 908. Chute 932 defines a void space 938 above shell opening 926 for receiving the bone stock to be cleaned. A cap 915 covers the plunger passage 934.

A plunger 940, seated in chute 932 presses the bone against the grater disc 914 to facilitate removal of soft tissue from the bone. The plunger 940 includes a plunger head 942 that is sized with an outer perimeter slightly smaller than the inner perimeter of the plunger passage 934 to slidably fit in the plunger passage 934. A shaft 944 has a first end 946 fixed to the plunger head 942. A handle 948 is fixed to a second end 950 of the shaft 944. The shaft 944 extends from the plunger head 942 in the passage 934 to handle 948. Shaft 944 extends through and is able to slide within cap 915.

A spring 952 is disposed about the shaft 944 between the cap 915 and the plunger head 942. Spring 952 urges the plunger head 942 downwardly toward the bone to press the bone against the grater disc 914. The plunger 940 is either manually or automatically operated.

As previously discussed, the hole 909 extending through the base 902 is occupied by the spindle 910. The spindle 910 extends from the circular plate 916 to an end 960 having features (such as a square shaft configuration) for mating with a drive system such as a drive motor (shown but not numbered). In the embodiment shown, the spindle 910 is rotatably fixed to both the discs 914, 918 to transmit power from the drive system to the discs 914, 918 thereby causing the discs 914, 918 to rotate when the drive system is operational. Alternatively, in the embodiments in which the cleaning head 900 is mounted to the base unit 52, the spindle 910 is not present and the discs 914, 918 engage and are rotatably fixed to the base unit spindle head 108 via the alignment pin 110 and teeth 112.

During operation, uncleaned bone is first placed in the void space 938 for cleaning and the cap 915 is then placed to cover the void space 938. The uncleaned bone includes soft tissue attached thereto that requires removal prior to processing by the mill head 60. The drive system or base unit 52 (if the cleaning head 900 is mounted to the base unit 52) is then actuated to start rotation of the spindle 910 and subsequent rotation of the discs 914, 918. Spring 952 presses the plunger 936 downwardly so that the plunger head 942 presses the bone against the grater disc 914. The grater disc 914 relies on the scallop edges that define the openings 920 to cut away the soft tissue from the bone.

During operation of the mill head 900, the user periodically pulls on handle 948 in order to overcome the force of the spring 952 that holds the plunger head 952 against the bone. The bone stock then rotates with the discs 914 and 918. Almost as soon as the bone stock rotates, the bone presses against the interior wall of the shell 908 that defines opening 926. This abutment of the bone stock against the shell and the rotation of the underlying grating disc 914 causes the bone to tumble in the opening 926. When manual force on the plunger 940 is released, spring 942 causes the plunger head 942 to return to its position against the bone. Since the bone has tumbled, at this time a different surface of the bone should be pressed against the grating disc for cleaning.

Once the cleaning head 900 has sufficiently removed soft tissue from the bone, the cap 915 is removed and the cleaned bone is grabbed by forceps or other device for further processing. The cleaning head 900 may then be cleaned or discarded. In some cases only the discs 914, 918 and the plunger 940 is discarded while the remaining components are sterilized and reused.

Again, RFID 270 and coil 271 (FIG. 5) may be embedded in the cleaning head base 902 to perform their previously defined functions.

Also, alternative structures may be employed to sequentially and repetitively press the bone against the grating disc 914 and tumble the bone so that each surface is pressed against the disc. For example, in some versions of the invention, spring 946 may be eliminated. In these versions of the invention, when the cleaning head 900 is actuated, the technician performing the cleaning operation will repetitively depress and retract the plunger 940. The depression of the plunger causes the plunger head 942 to press the bone against the grating disc 914. The retraction of the plunger 940 allows the bone to tumble. A mechanical device, such as a cam assembly may be used to lift and depress the plunger 940. This mechanical device may be used in versions of the invention that both include and do not include the spring 946 that acts against the plunger 940.

In versions of the invention in which manual force is used to press the bone against the cleaning disc, there may be a mechanism to limit the amount of this force. This may be desirable to minimize the likelihood that, due to the bone being pressed against the disc 914, the bone is inadvertently milled. One such force-limiting component may be a spring connected at one end to the cap and at the second end to the plunger head. This spring is sized such that, instead of forcing the plunger head against the disc, it holds the head above the disc. Manual force is then required to overcome the spring force to push the plunger head downwardly in order to press the bone against the disc. The spring thus attenuates the manual force the technician is able to apply to the plunger head during the cleaning process.

In still another version of the invention, the grating disc 940 may be formed to have one or ribs. Each rib projects upwardly from the surface of the disc against which the bone stock is depressed. As the disc rotates, the rib/ribs rotate under the bone stock. The movement of a rib under the bone stock serves to force the bone to at least partially rotate, tumble, within the shell opening 926. Again, this version of the invention may or not include the spring 946 that acts against the plunger 940. Should the spring be present, the spring is selected so that the spring force exerted can be overcome by the action of a disc rib pushing up against the bone.

Alternatively, the grater disc may be formed with one or more flexible tabs. A tab may, for example, be formed in an arcuate section of the disc that is free from of openings. The surface of the tab angles upwardly from the opening defining section of the disc. As the disc rotates, the bone rides over the inclined surface of the tab. The flexible nature of the tab allows the tab and bone to at least partially overcome any force holding the bone against the grating disc. As the disc continues to rotate, the bone drops of the elevated edge of the tab. This dropping off, rolling off, of the bone serves to rotate the bone so as to present another surface of the bone against the grater disc for cleaning.

XIII. Sixth Alternative Cleaning Head

Figure 52:
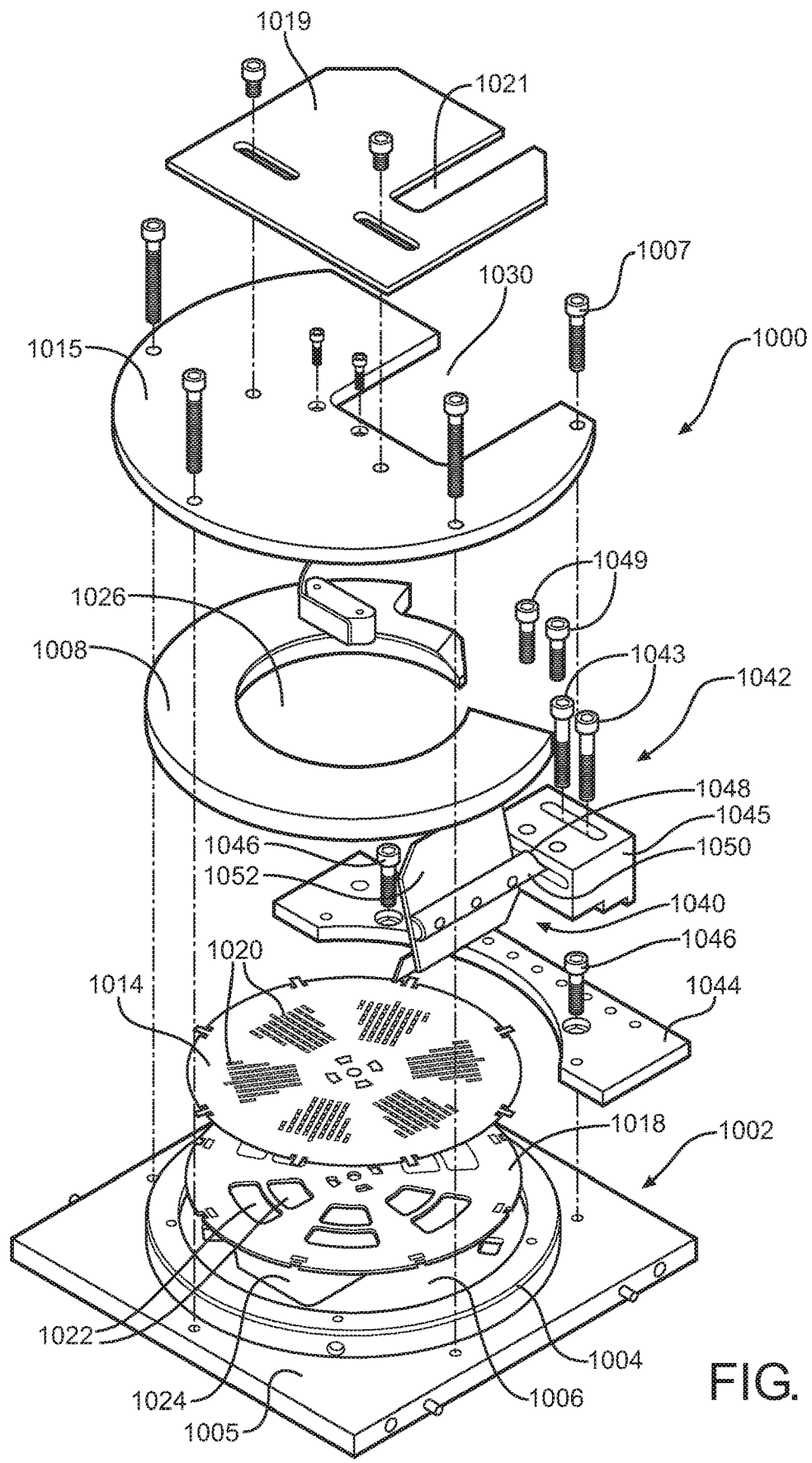
FIG. 52 is an exploded view of a sixth alternative cleaning head of this invention comprising a rotating grater and an impingement plate.
Figure 53:
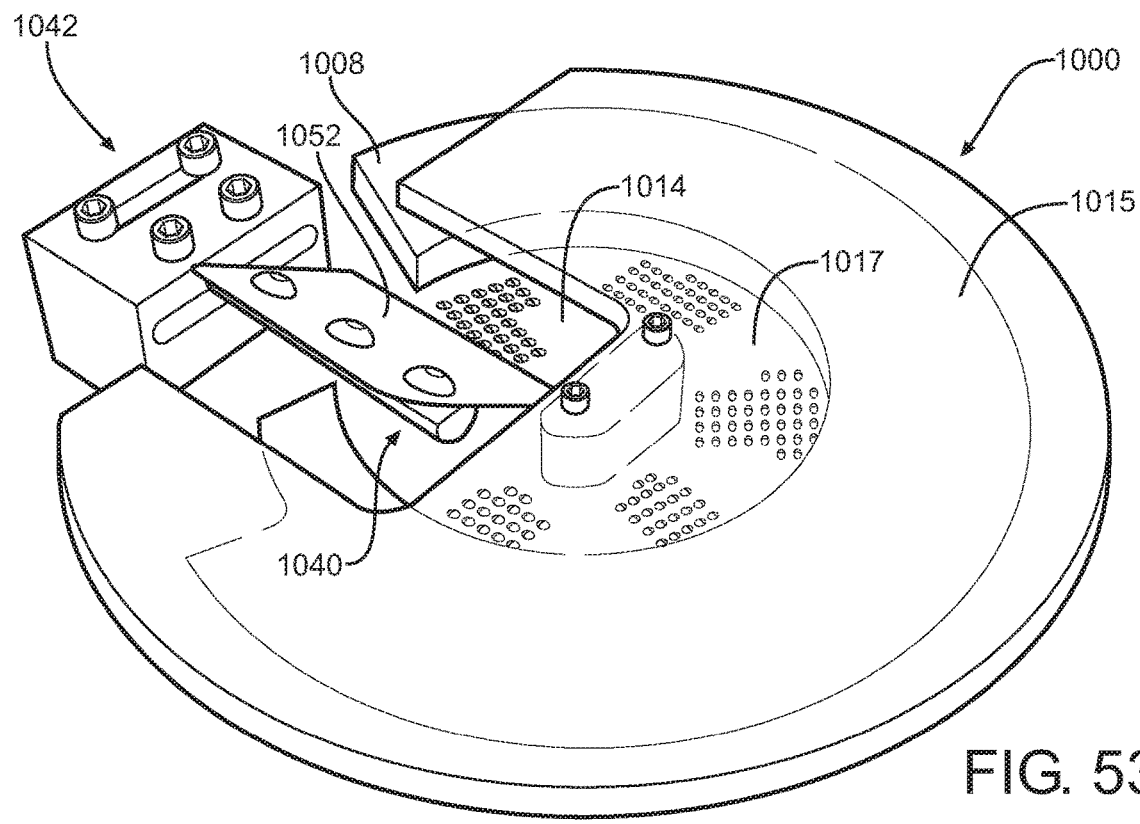
FIG. 53 is a top perspective view of the alternative cleaning head of FIG. 52 illustrating the rotating grater and the impingement plate.

FIGS. 52 and 53 depict a sixth alternative cleaning head 1000. Cleaning head 1000 is similar to the cleaning head 900 except that the plunger 940 is replaced with an impingement plate 1052. Impingement plate 1052 compresses the bone against grater openings. The cleaning head 1000 comprises a base 1002. A ring-shaped section 1004 of the base 1002 protrudes upwardly from a bottom section 1005 of the base 1002. A cavity 1006 is defined radially inwardly from the protruding ring-shaped section 1004. A shell 1008 is mounted to the base 1002 on top of the ring-shaped section 1004 and above the cavity 1006. The base 1002 and shell 1008 can be formed from the same material from which the shells 192 and 194 of head 56 are formed. Alternatively, if cleaning head 1000 is a use-once unit, base 1002 and shell 1008 may be formed from a sterilizable plastic such as a polycarbonate plastic.

The bottom section 1005 of the base 1002 is similar to that of base 902 bottom section 905 described with respect to FIGS. 50 and 51. Accordingly, the cleaning head 1000 may be a stand-alone unit for cleaning bone in which the base 1002 is simply attached to a separate drive system (shown but not numbered). Alternatively, base 1002 may also be configured for use with the base unit 52 so that the cleaning head 1000 is operated by the base unit 52. In this embodiment, the base 1002 has an outer diameter that allows the base 1002 to be slip fitted within the circular void space defined by the base unit lip 78. Like the second alternative cleaning head 630, the base 1002 is circular in shape and four equiangularly spaced notches (not shown) extend upwardly from the bottom of the base 1002 around the outer perimeter of the base 1002. The notches receive the pedestal teeth 84 when the cleaning head 1000 is seated on the base unit 52. A groove (not shown), like groove 642, extends inwardly around the circumferential outer surface of the base 1002. The base 1002 is formed to have two diametrically opposed notches (not shown), like notches 644 (one shown in FIG. 32) that extend inwardly from the outer circumferential surface of the base 1002. Each notch being dimensioned to receive a separate one of the fingers 88 integral with the base unit retention arms 86.

Referring back to the FIGS. 52 and 53, base 1002 has a through hole (not shown, but same as the hole 909 shown in FIG. 51) that extends top-to-bottom through the base 1002. The hole is centered along the top to bottom longitudinal axis of the base 1002. The hole is occupied by a spindle (not shown, but same as the spindle 910 shown in FIG. 51). The spindle is rotatably supported in bearings (not shown, but same as the bearings 912 shown in FIG. 51) mounted to the base 1002. The spindle forms part of the drive assembly of the cleaning head 1000. In the embodiments in which the cleaning head 1000 is mounted to and operated by the base unit 52, the spindle is not present and the hole is dimensioned to allow the base unit spindle head 108 to freely move therein and engage the cleaning head 1000.

A cleaning element 1014 in the form of a rotating grater 1014 is disposed in the cavity 1006. The grater 1014 is preferably formed of stainless steel. The grater 1014 is disc shaped and has features for engaging a circular plate (not shown, but same as the circular plate 916 shown in FIG. 51) of the spindle to rotate with the spindle. An reinforcing disc 1018 is disposed between the circular plate and the grater disc 1014. The grater disc 1014 includes a plurality of openings 1020. The perimeter of each opening 1120 is defined by a raised scallop (not identified). The edges of the scallops that define the openings file away soft tissue from bone. Reinforcing disc 1018 includes larger openings 1022 sized to allow filed off pieces of soft tissue to fall therethrough and out of the cleaning head 1000 via a chute 1024 in the base 1002. Both discs 1014, 1018 are rotatably fixed to the spindle 1010 to rotate with the spindle 1010 during operation.

The openings 1020 are preferably confined to circumferentially spaced areas on the grater disc 1014 such that the entire grater disc 1014 is not formed with the openings 1020. This increases the strength of the grater disc 1014. These spaced areas coincide with the larger openings 1022 in the reinforcing disc 1018 to further facilitate movement of the filed off soft tissue through the discs 1014, 1018. The dimension(s) of the openings 1020 are such that the soft tissue and debris present on the uncleaned bone is filed away and removed to clean the bone, but the bone itself is not damaged or diminished beyond a usable state. In other words, the openings 1020 are sized and configured not to result in milling the bone like the mill element 62 of the mill head 60. In one embodiment, the openings 1020 are rectangular in shape with a larger length than width (see FIG. 51A). In a more specific embodiment, the openings 920 are 0.39 cm or less long by 1.3 cm or less wide. Adjacent openings 1020 are spaced in parallel columns and rows with approximately 0.2 cm or less between rows and 0.1 cm or less between columns.

An opening 1026 is defined through the shell 1008 above the grater disc 1014. A cap 1015 partially covers the opening 1026 to define a void space 1017 for the bone. The cap 1015 is mounted to the base via fasteners 1007 with the shell 1008 captured between the cap 1015 and the base 1002. The void space 1017 in this embodiment is defined radially inwardly of the shell 1008, below the cap 1015 and above the grater disc 1014. The cap 1015 further has an opening 1030 coinciding with a portion of the void space 1017.

An impingement mechanism is disposed in the opening 1030 above the grater disc 1014. The impingement mechanism includes a plate 1052 that presses the bone against the grater disc 1014. Plate 1052 is flexible. The impingement mechanism includes a block 1045 that is mounted to a bracket 1044 by fasteners 1043. Bracket 1044 is fixed to the base 1002 by fasteners 1046. Block 1045 is formed with an elongated slot 1048 for receiving a shaft 1050 to which plate 1052 is mounted. One end of shaft 1050 is seated in block slot 1048. Set screws 1049 hold the shaft 1050 in a fixed rotational position in slot 1048. The impingement plate 1052 is fixed fitted over the second end of the shaft 1050. Set screws 1049 allows the angular relationship between the impingement plate 1052 and the grater disc 1014 to be altered for different applications and different sizes of bone. A secondary cap 1019 extends over block 1045. The secondary cap 1019 is formed with a slot 1021 sized to receive a section of the impingement plate 1052.

As previously discussed, the hole extending through the base 1002 is occupied by the spindle. The spindle extends from the circular plate to an end (not shown, but same as the end 960 in FIG. 51) having features (such as a square shaft configuration) for mating with a drive system such as a drive motor (shown but not numbered). In the embodiment shown, the spindle is rotatably fixed to both the discs 1014, 1018 to transmit power from the drive system to the discs 1014, 1018 thereby causing the discs 1014, 1018 to rotate when the drive system is operational. Alternatively, in the embodiments in which the cleaning head 1000 is operated by the base unit 52, the discs 1014, 1018 are configured to engage and be rotatably fixed to the base unit spindle head 108 via the alignment pin 110 and teeth 112.

To clean bone stock, the bone is initially placed in the void space 1017. Cap 1015 is then placed to cover the void space 1017. The drive system or base unit 52 (if the cleaning head 1000 is mounted to the base unit 52) is then actuated to start rotation of the spindle and subsequent rotation of the discs 1014, 1018. The bone rotates with the grater until the bone rotates below the impingement plate 1052, the surface of the impingement plate that is directed towards the disc 1014. Initially, the impingement plate holds the bone against the grater disc 1014. This holding action presses the bone against the cleaning disc so the disc removes the soft tissue from the bone. However, the impingement plate is flexible. As a result, the disc is able to push the bone below and across the impingement plate 1052. It should be appreciated that during this transit of the bone, the impingement plate flexes. As the bone travels under the impingement plate, the bone is momentarily caught by the bottom edge of the impingement plate 1052. As the impingement plate 1052 snaps back to the static state, the plate rotates the bone over the grater disc. This presents a different surface of the bone is disposed against the disc. Once the cleaning head 1000 has sufficiently removed soft tissue from the bone, the cap 1015 is removed and the cleaned bone is grabbed by forceps or other device for further processing. The cleaning head 1000 may then be cleaned or discarded. In some cases only the discs 1014, 1018 are discarded while the remaining components are sterilized and reused.

XIV. Seventh Alternative Cleaning Head

A seventh alternative cleaning head 1100 is now described by reference to FIGS. 54 through 56. Cleaning head 1100 includes a base 1102. A ring-shaped section 1104 of the base 1102 protrudes upwardly from a bottom section 1105 of the base 1002. A cavity 1106 is defined radially inwardly from the protruding ring-shaped section 1004. A shell 1108 is mounted to the base 1102 on top of the ring-shaped section 1104 and above the cavity 1106. The base 1102 and shell 1108 can be formed from the same material from which the shells 192 and 194 of head 56 are formed. Alternatively, if cleaning head 1100 is a use-once unit, base 1102 and shell 1108 may be formed from a sterilizable plastic such as a polycarbonate plastic.

Figure 54:
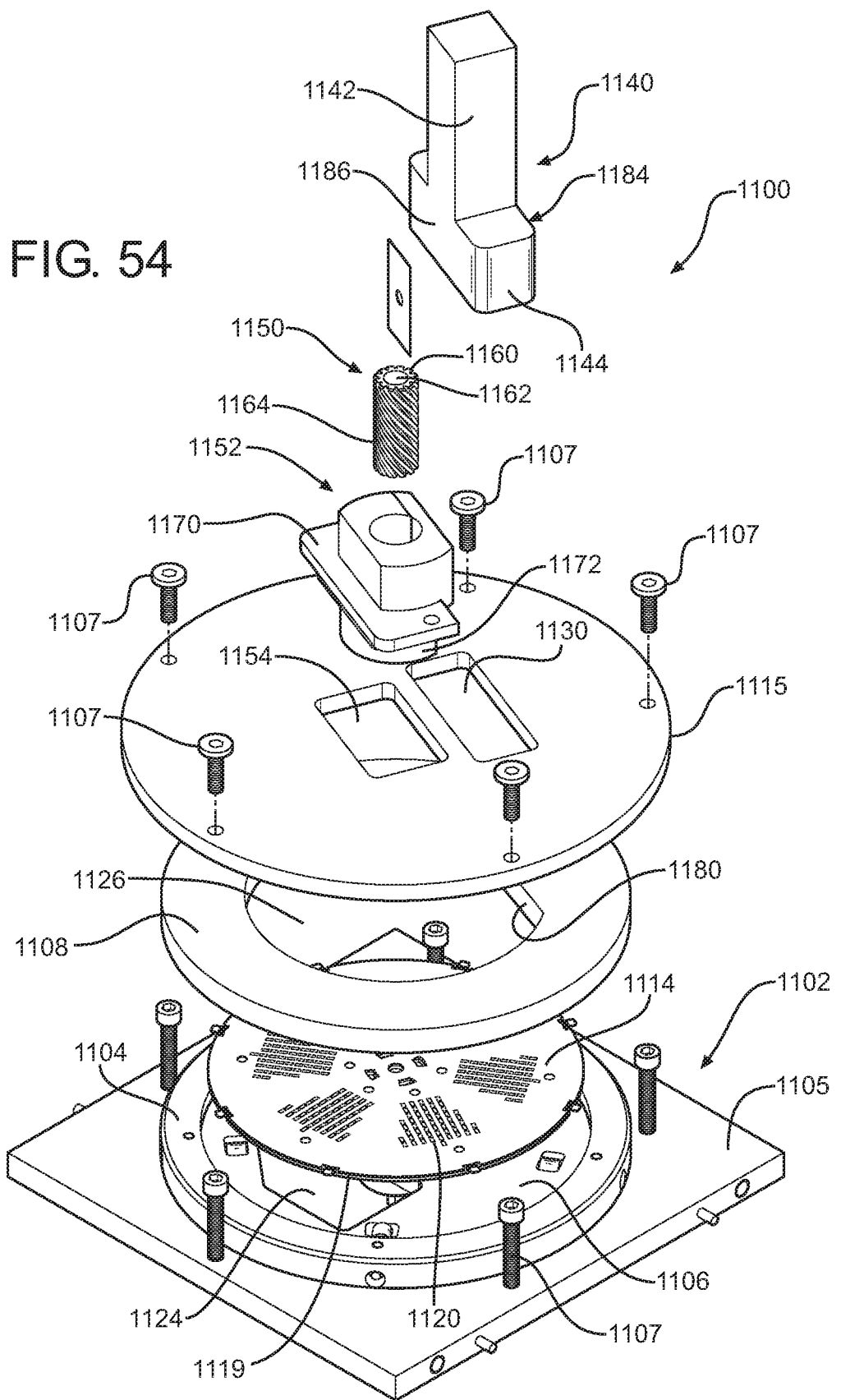
FIG. 54 is an exploded view of a seventh alternative cleaning head of this invention comprising a rotating grater, rotating fluted screw, and plunger.
Figure 55:
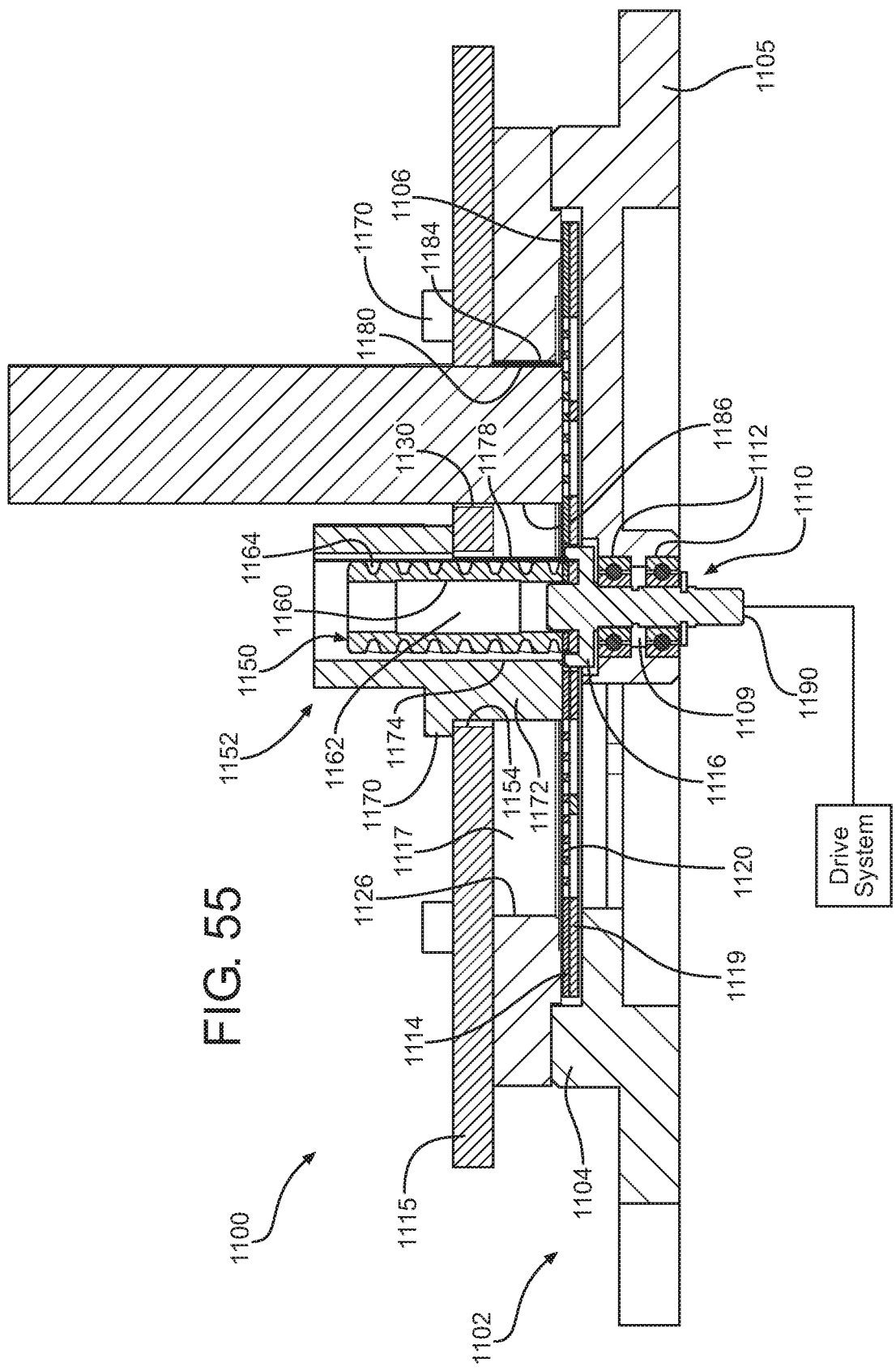
FIG. 55 is a cross-sectional view of the alternative cleaning head of FIG. 54.

The bottom section 1105 of the base 1102 is shown in FIG. 54 as being rectangular in shape without any features for engaging the base unit 52. Accordingly, the cleaning head 1100 may be a stand-alone unit for cleaning bone in which the base 1102 is simply attached to a separate drive system (shown but not numbered). However, the base 1102 may be configured to be seated in the base unit 52 and operated by the base unit 52 in other embodiments. In these embodiments, the base 1102 has an outer diameter that allows the base 1102 to be slip fitted within the circular void space defined by the base unit lip 78. In this case, like the second alternative cleaning head 630, the base 1102 is circular in shape and four equiangularly spaced notches (not shown) extend upwardly from the bottom of the base 1102 around the outer perimeter of the base 1102. The notches receive the pedestal teeth 84 when the cleaning head 1100 is seated on the base unit 52. A groove (not shown), like groove 642, extends inwardly around the circumferential outer surface of the base 1102. The base 1102 is further formed with two diametrically opposed notches (not shown), like notches 644 (one shown in FIG. 32) that extend inwardly from the outer circumferential surface of the base 1102. Each notch being dimensioned to receive a separate one of the fingers 88 integral with the base unit retention arms 86.

Returning to FIGS. 54-56, base 1102 has a through hole 1109 that extends top-to-bottom through the base 1102. The hole 1109 is centered along the top to bottom longitudinal axis of the base 1102. The hole 1109 is occupied by a spindle 1110. The spindle 1110 is rotatably supported in bearings 1112 mounted to the base 1102. The spindle 1110 forms part of the drive assembly of the cleaning head 1100. In the embodiments in which the cleaning head 1100 is mounted to the base unit 52, the hole 1109 is dimensioned to allow the base unit spindle head 108 to freely move therein and engage the cleaning head 1100.

A cleaning element, in the form of a rotating grater 1114 is disposed in the cavity 1106. Grater 1114 is preferably formed from stainless steel. The grater 1114 is disc shaped and has features for engaging a circular plate 1116 of the spindle 1110 to rotate with the spindle 1110. A reinforcing disc 1119 may be disposed between the circular plate 1116 and the grater disc 1114. The grater disc 1114 includes a plurality of openings 1120 configured to file away soft tissue from bone. The filed off tissue thereafter falls through the openings 1120 and out of the cleaning head 1100 through an opening 1124 in the base 1102. The disc 1114 is rotatably fixed to the spindle 1110 to rotate with the spindle 1110 during operation.

The openings 1120 are preferably confined to circumferentially spaced areas on the grater disc 1114 such that the entire grater disc 1114 is not formed with the openings 1120. This increases the strength of the grater disc 1114. The dimension(s) of the openings 1120 are such that the soft tissue and debris present on the uncleaned bone is filed away and removed to clean the bone, but the bone itself is not damaged or diminished beyond a usable state. In other words, the openings 1120 are sized and configured not to result in milling the bone like the mill element 62 of the mill head 60. In one embodiment, the openings 1120 are rectangular in shape with a larger length than width (see FIG. 51A). In a more specific embodiment, the openings 1120 are 0.39 cm or less long by 1.3 cm or less wide. Adjacent openings 1120 are spaced in parallel columns and rows with approximately 0.2 cm or less between rows and 0.1 cm or less between columns.

An opening 1126 is defined through the shell 1008 above the grater disc 1114. A cap 1115 partially covers the opening 1126 to define a void space 1117 for the bone. The cap 1115 is mounted to the base via fasteners 1107. The shell 1108 is captured between the cap 1115 and the base 1102. The void space 1117 in this embodiment is defined radially inwardly of the shell 1108, below the cap 1115 and above the grater disc 1114. The cap 1115 further has an opening 1130 coinciding with a portion of the void space 1117.

A plunger 1140 is moveably mounted to cleaning head 1100. The plunger 1140 has a handle 1142 to which, at one end, a head 1114 is attached. The plunger head 1144 is sized slightly smaller and has a shape similar to that of opening 1130 to fit through the opening with minimal clearance. The plunger head 1144 is manually (shown) or mechanically (not shown) reciprocated in the opening 1130 to press bone against the grater disc 1114. The plunger 1140 is preferably formed of stainless steel or sterilizable plastic.

A second cleaning element, a fluted screw 1150 is disposed in the void space 1117. A shaving block 1152 rotatably supports the fluted screw 1150. The shaving block 1152 is located through another opening 1154 in the cap 1115. The shaving block 1152 is generally centrally located in the void space 1117 but in other embodiments may be located about the periphery of the void space 1117 similar to the third alternative cleaning head 700. Additional fluted screws 1150 may also be employed. In the embodiment shown, the fluted screw 1150 comprises a sleeve 1160 defining a through bore 1162. The sleeve 1160 is preferably fixed to rotate with the spindle 1110. The sleeve 1160 defines a plurality of flutes 1164 that facilitate gripping and tearing of soft tissue from the bone in the void space 1117 during rotation to clean the bone. The fluted screw 1150 is preferably formed of stainless steel.

Figure 56:
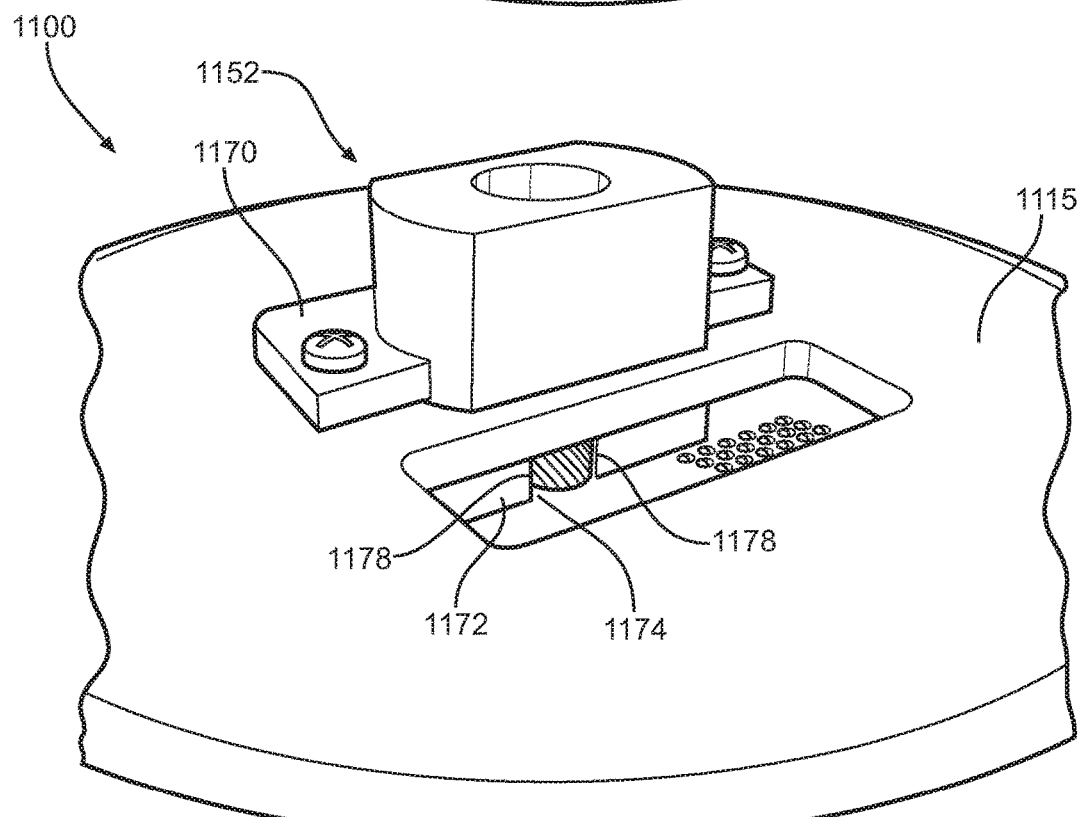
FIG. 56 is a top perspective view of the alternative cleaning head of FIG. 54 illustrating the rotating grater and rotating fluted screw.

Referring to FIG. 56, the shaving block 1152 is preferably formed of stainless steel. The shaving block 1152 has a flange 1170 mounted to the cap 1115 about the opening 1154. A wall 1172 of the shaving block 1152 extends through the opening 1154 and is suspended slightly above the grater disc 1114 so as not to disrupt rotation of the grater disc 1114. The spacing between a bottom of the wall 1172 and the grater disc 1114 is too small for any bone to pass thereunder. An elongated space 1174 is defined in the wall 1172 to receive the fluted screw 1150. The fluted screw 1150 rotates in the elongated space 1174 in the wall 1172. A first end of the fluted screw 1150 is rotatably mounted to the shaving block 1152 while the opposite end of the fluted screw 1150 is fixed to the spindle 1110. A portion of the fluted screw 1150 extends a distance away from a front surface 1176 of the wall 1172 to grip soft tissue attached to bone disposed in the void space 1117.

Shaving block 1152 is shaped to define a pair of cutting edges 1178 disposed on opposing sides of the elongated space 1174 (see FIG. 56). These cutting edges 1178 are sharp enough to cut soft tissue that the fluted screw 1150 has gripped or captured during rotation. In other words, the fluted screw 1150 engages the soft tissue still attached to bone and impinges that soft tissue against the cutting edges 1178 during rotation to cut the soft tissue away from the bone. Plunger head 1144 is designed to force the bone toward the fluted screw 1150. As a result of the abutment of the bone against the screw 1150, soft tissue attached to the bone is pressed into the spaces between the flutes. As the screw 1150 rotates, the tissue entrained in the screw 1150 is rotated against the cutting edges 1178. The continued rotation of the screw with the entrained tissue results in the cutting edges separating the tissue from the bone. The sharp edges of the flutes of screw 1150 also separately cut some soft tissue from the bone although to a limited extent.

The plunger head 1144 is generally box-shaped to correspond to the box-shaped opening 1130. The shell 1108 has a flat 1180 on an inner surface thereof that corresponds to a first flat side 1184 of the plunger head 1144. Accordingly, when the plunger head 1144 is disposed in the opening 1130, the first flat side 1184 of the plunger head 1144 faces the flat 1180 on the inner surface 1182 of the shell 1108 with a small gap defined therebetween (see FIG. 55). The small gap is sized to prevent bone from entering. Opposite the flat 1180 on the other side of the plunger head 1144 is the fluted screw 1150 and shaving block 1152. A gap between a second flat side 1186 of the plunger head 1144 and the fluted screw 1150 is sized to restrictively receive small pieces of bone. As a result, all of the bone must pass under the plunger head 1144 so as to be compressed by the plunger head 1144 against the grater disc 1114 to remove soft tissue from the bone or pass between the plunger head 1144 and the fluted screw 1150 to be grabbed by the fluted screw 1150 with the associated soft tissue being grabbed by the fluted screw 1150 and cut by the cutting edges 1178.

As previously discussed, the hole 1109 extending through the base 1102 is occupied by the spindle 1110. The spindle 1110 extends from the circular plate 1116 to an end 1190 having features (such as a square shaft configuration) for mating with a drive system such as a drive motor (shown but not numbered). In the embodiment shown, the spindle 1110 is rotatably fixed to both the grater disc 1114 and the fluted screw 1150 to transmit power from the drive system to the grater disc 1114 and the fluted screw 1150 thereby causing the grater disc 1114 and the fluted screw 1150 to rotate when the drive system is operational. Alternatively, when the cleaning head 1100 is operated by the base unit 52, the grater disc 1114 and the fluted screw 1150 are configured to engage and be rotatably fixed to the base unit spindle head 108 via the alignment pin 110 and teeth 112.

During operation, uncleaned bone is first placed in the void space 1117 for cleaning and the cap 1115 is then placed to cover the void space 1117. The uncleaned bone includes soft tissue attached thereto that requires removal prior to processing by the mill head 60. The drive system or base unit 52 (if the cleaning head 1100 is mounted to the base unit 52) is then actuated to start rotation of the spindle 1110 and subsequent rotation of the grater disc 1114 and the fluted screw 1150. The grater disc 1114 relies on the scallop edges that define openings 1120 to cut away the soft tissue from the bone. The grater disc 1114 and the plunger head 1144 operate to tumble the bone. The plunger head 1144 presses the bone against the grater disc 1114 to enhance the cutting away of soft tissue from the bone by the scalloped openings 1120. The fluted screw 1150 grips soft tissue attached to the bone and cuts the soft tissue away from the bone either by the nature of the flutes 1164 on the fluted screw 1150 or by impinging the soft tissue against the cutting edges 1178 of the shaving block 1152. Once the cleaning head 1100 has sufficiently removed soft tissue from the bone, the cap 1115 is removed and the cleaned bone is grabbed by forceps or other device for further processing. The cleaning head 1100 may then be cleaned or discarded. In some cases only the grater disc 1114 and plunger 1140 are discarded while the remaining components are sterilized and reused.

XV. Alternative Embodiments

The foregoing has been directed to specific versions of system of this invention. Other versions of the system of this invention may have features different from what has been described.

For example, various features of the versions of this invention may be combined. Thus, in some versions of the invention wherein there is a single head with both cleaning and milling modules, the cleaning module may have a drive assembly that rotates both the lower and upper brushes.

Likewise the features of the invention may be different from what has been described. In some versions of the invention, the cleaning head cleaning elements and mill head mill elements may have common coupling features for engaging to the common drive spindle but different coupling features for holding the cleaning head and mill head to the base unit.

Similarly the cleaning head and mill head may have common coupling features for holding the head to the base unit. These versions of the invention may then have different coupling features for coupling to different drive members integral with the base unit. Thus, instead of having a single drive spindle, the base unit may have separate drive spindles that are driven at different speeds, a first speed for the cleaning head 56 and at a second speed for the mill head 60. A common gear assembly connects both of these spindles to the output shaft of motor 54 (shaft not illustrated). In these versions of the invention, the complementary coupling features the cleaning element and mill element are provided may be different from each other.

Similarly, there is no requirement that in all versions of the invention the cleaning elements and mill elements be disc shaped members that rotate around their center axis. In some versions of the invention, for example, one or both of the cleaning elements or mill elements may be tube shaped. A brush so shaped may have a bristles that extend inwardly from the body of the brush. This brush is used by placing the bone stock to be cleaned inside the brush. A mill element so shaped may have cutting edges that emerge from the outer face of the body. The bone is pressed against this surface. The formed chips fall into a catch tray located within the center of the mill element. The above described brush and mill element are therefore designed to be rotated around the axis that extends through its central lumen.

Both the cleaning head and mill head of this invention may have features in addition to what has been described. For example, the cap associated with mill head 56 may be fitted to the post 286 integral with brush 59. This allows the medical personnel to by pressing down on the cap, press down on the brush 59. The pressing down on the brush thus increases the force of the bristles against the bone located between the brushes 58 and 59.

The integrated cleaning and mill head of this invention may have features different from the described head 490. For example in some versions of the device, the cleaning module may be statically mounted to the other components. In these versions of the invention, the movement of a trap establishes a path through the cleaned bone can pass into the milling module. Also, in some versions of the invention, a mechanical member may physically displace the cleaned bone so as to effect the transfer of the cleaned bone to the milling module. In some versions of this embodiment of the invention, the trap (or member) that allows (performs) the transfer of the cleaned bone from the cleaning module to the milling module may be automatically actuated. This would further reduce the amount of time the surgical personnel need to devote to performing and/or monitoring the bone cleaning and bone milling processes.

Also, in some versions of the invention, the brush bristles may not always be of constant height. In some versions of the invention it may be desirable to construct the lower brush so that the bristles adjacent the center of rotation of the brush are of lower height than the bristles spaced from the center of rotation. In these versions of the invention, it may also be desirable to construct the upper brush so its bristles close to the center of rotation are longer than the bristles spaced from this axis. It is believed that an advantage of provide brushes having these features is that the bristle arrangement reduces the extent to which centrifugal force causes the bone stock being cleaned to move to the outer perimeter of the brushes. By maintaining the bone stock adjacent the center of the brushes, the likelihood that the bone stock becomes trapped between the outer perimeter of the brushes and surrounding surfaces of the cleaning head housing is significantly reduced. Should the bone stock become so trapped, the effectiveness of the cleaning process can be adversely affected.

Likewise it should be understood that in versions of the invention with integrated cleaning and milling modules, these modules may not be removable from the base as a single piece unit. In some versions of the invention the cleaning module and milling modules may be separately removable. After use, each module is independent sterilized, the worn parts replaced, and reattached to the base unit.

It should likewise be appreciated that versions of the system of the invention can include less than all the described components. Not all versions of the invention may include memories that describe the specific speeds at which the cleaning elements and mill elements should be driven. This is especially true for versions of the invention wherein the cleaning elements and mill elements are drive at the same speed. This may also be true for versions of the invention wherein the base unit has two drive spindles that are geared to operate at different speeds.

Some versions of the invention may not include a removable catch tray for holding the milled bone. Some cleaning heads/modules of this invention may only have a single cleaning element. In some versions of the invention, the brushes may not have bristles. Instead, each brush has an abrasive surface that when is rubbed against the bone stock, cleans the bone stock.

Further in some versions of the invention the cleaning head drive assembly that simultaneously rotates brushes 416 and 418 may rotate the brushes in the same direction. Drive assembly may also be provided that rotate the brushes or other cleaning elements at different speeds.

Cleaning head 630 may, in some versions of the invention be provided with a removable retaining ring. This ring has a rim that extends over the cap rim 684. The ring has a skirt with features that facilitate the removable coupling of the ring to the base 632. The ring is coupled to the rest of the head during the cleaning process in order to prevent the inadvertent lifting of the cap away from the underlying base 632 and brush 58.

Alternatively, cleaning head 630 may be constructed so that the void space in which brush 58 is seated has a depth greater than the height of the brush.

In some versions of the invention in which the cleaning head is provided with a cap that is flexed against the brush, the cap may have a hand hold. The hand hold may include a cylindrical neck that extends upwardly from the apex of the cap dome. A head, also cylindrical in shape, disposed above the neck and that extends radially outwardly beyond the neck is also part of this hand hold. During the cleaning process, the individual charged with the cleaning grasps the hand hold to push down on the cap and also move cap so the top of the cap is turned from side to side. This turning of the cap changes the orientation of the bristles that extend downwardly from the cap. This changing of the orientation of the bristles can, in some circumstances, improve the efficiency of the cleaning process.

The cleaning head and mill head of this invention may be provided with features other than the disclosed spout 668 and sleeve 308 for facilitating the coupling of these two heads together as part of the bone transfer process. For example in some versions of the invention, the cleaning head may have a spout that is dimensioned to seat in the mill head feed port into which the cleaned bone stock is introduced into mill head.

Likewise it should be understood that while this invention is intended for use to clean autograft bone, its applications are not so limited. System 50 of this invention may also be used to clean and mill donor bone, sometimes referred to as allograft bone.

The materials from which the components of this invention are fabricated may be different from what has been described. For example, in some versions of the invention, the enter cleaning head, including the housing-forming shell components may be disposable. In these versions of the invention, the components forming the housing, instead of being made of metal may be made of sterilizable plastic. Likewise, there is no requirement that the brushes always include bristles formed from stainless steel. The bristles may be formed from other bendable metals not prone to breakage such as titanium or alloys of titanium.

The geometry of the components may also vary. For example, in the versions of the invention wherein the cleaning element is disc, the scallops with edges that performing the cleaning function are illustrated as being in sets of arcuately spaced apart clusters. In alternative versions of the invention, the scallops with edges, and complementary openings are formed throughout the whole of the body of the disc. There are no scallop and opening free sections of the disc.

It should further be appreciated that the processing steps executed by the system may be different from what has been described. For example, the cleaning head and mill head memories are described as having flag bits that are set once the head is used. This is to prevent reuse of an unsterilized head for a procedure on a new patient. However, there may be times when, after an initial amount is cleaned and milled, the surgeon decides that it is necessary to have additional bone chips available. Accordingly, the software may have an override that allows the surgical personnel to, after acknowledging that cleaning head or mill head was used, to reuse the cleaning head. Thus allows the personnel to reuse the heads during the same procedure on a single patient.

Also, while the invention is described as a combined system for both cleaning and milling bone, other versions of the invention may not perform both functions. The base unit and cleaning head may form a system of this invention that is used just to clean bone. The advantage of the system being that it provides a mechanized means of cleaning the bone that substantially eliminates the need for surgical personnel to hold the bone. Also, depending on the system of this invention, it may be that the cleaning elements are the only disposable portion of the system. Depending on the materials forming components from which this system is fabricated, this may limit the expenses associated with providing the system.

Further it should be clear that various ones of the cleaning elements described above as well as other cleaning elements may be combined together in a single cleaning head.

Also there is no requirement that the system of this invention be constructed so that first the bone be cleaned and then milled. In some versions of the invention, the bone may initially be milled to form chips of substantially uniform size. These chips are then processed by a cleaning head/module. The cleaning head contains cleaning elements shaped especially to clean the chips of produced by the mill head/module.

Accordingly, it is an object of the appended claims to cover all such variations and modifications as come within the true spirit and scope of the invention.

What is claimed is:

1. A method of cleaning bone stock with an assembly comprising a motor and a cleaning head defining a void space, said method comprising the steps of:
generating a sequence of instructions that indicate a speed and/or a direction in which the motor should rotate to clean bone;
placing harvested bone stock into the void space, the harvested bone stock having a surface including soft tissue; and
actuating the motor according to the sequence of instructions to remove the soft tissue and clean the bone stock.

2. The method of claim 1 wherein the step of actuating the motor is further defined as actuating the motor to cause rotation of a brush and/or an abrasive surface.

3. The method of claim 1 further comprising the step of configuring the sequence of instructions based on personal preferences.

4. The method of claim 1 further comprising the step of coupling the cleaning head to a base unit including the motor.

5. The method of claim 1 further comprising the step of decoupling the cleaning head from a base unit and optionally disposing the decoupled cleaning head.

6. The method of claim 5 further comprising the step of reusing the base unit with a different cleaning head or a mill head.

7. The method of claim 4 further comprising the step of reading data in memory of the base unit to determine that the cleaning head is coupled to the base unit.

8. The method of claim 7 further comprising the step of configuring a control console based on recognition that the cleaning head is coupled to the base unit.

9. The method of claim 7 further comprising the step of reading out from memory of the cleaning head indicating a speed range of the motor and a current the motor should draw.

10. The method of claim 5 further comprising the step of coupling a mill head to the base unit, the mill head having at least one mill element for converting bone stock introduced into the mill head into bone chips.

11. The method of claim 10 further comprising the step of actuating the motor of the base unit to cause a like actuation of the mill element, wherein actuation of the mill element converts bone stock into bone chips suitable for implantation into a patient.

12. The method of claim 10 further comprising the step of decoupling the mill head from the base unit and, optionally, disposing the mill head.

13. The method of claim 12 further comprising the step of reusing the base unit with a different mill head or another of the cleaning head.

14. A method of cleaning bone stock with an assembly comprising a base unit including a motor, and a cleaning head configured to be removably attached to the base unit and defining a void space with at least one brush moveably mounted therein, said method comprising the steps of:
attaching the cleaning head to the base unit;
placing harvested bone stock into the void space, the harvested bone stock having a surface including soft tissue; and
actuating the motor and consequently the at least one brush operatively attached thereto to remove the soft tissue from the bone stock.

15. The method of cleaning bone stock as set forth in claim 14 wherein the step of actuating the at least one brush is further defined as rotating the at least one brush within the void space about an axis that extends through a top-to-bottom center of the brush.

16. A method of cleaning bone stock with an assembly comprising a cleaning head, the cleaning head including opposed lower and upper shells configured to releasably couple together, and a motor, said method comprising the steps of:
coupling the shells together to define a void space;
placing harvested bone stock into the void space, the harvested bone stock having a surface including soft tissue;
actuating the motor to remove the soft tissue from the bone stock; and
separating the shells to access the bone stock having soft tissue removed therefrom.

17. The method of claim 16 further comprising the step of rotatably and removably disposing a brush in the lower shell.

18. The method of claim 17 further comprising the step of identifying the brush that is disposed in the lower shell.

19. The method of claim 18 further comprising the step of indicating whether or not the brush is useable.

20. The method of claim 18 further comprising the step of indicating operating speeds and motor directions for the identified brush.

21. A method of cleaning bone stock with a cleaning head defining void space including a fluted screw and a shaving block being at least partially disposed about the fluted screw and having at least one cutting edge, said method comprising the steps of:
placing bone stock into a void space, the bone stock having a surface with soft tissue coupled thereto; and
rotating the fluted screw within the shaving block to engage the soft tissue on the bone stock and impinging the soft tissue against the at least one cutting edge to remove the soft tissue from the surface of the bone stock.

22. The method of claim 21 wherein the cleaning head comprises an agitator disposed in the void space configured to urge bone stock towards the fluted screw and shaving block, said method further comprising the step of actuating the agitator to facilitate cleaning of the bone stock by the fluted screw and shaving block.

23. The method of claim 22 wherein the step of actuating the agitator within the void space of the cleaning head is further defined as rotating the agitator to tumble the bone stock and force the bone stock against the fluted screw and the shaving block.

24. The method of claim 22 wherein the agitator includes a stem disposed about a rotational axis and a pair of fins extending radially outwardly from the stem wherein during actuation the pair of fins pick up and tumble the bone stock and press the bone stock outwardly away from the rotational axis of the agitator and into the fluted screw and the shaving block.

25. The method of claim 22 wherein the steps of actuating the fluted screw and the shaving block, and actuating the agitator, are conducted simultaneously.

26. The method of claim 22 wherein the steps of actuating the fluted screw and the shaving block, and actuating the agitator, are conducted at the same or different rotational speeds.

27. The method of claim 22 wherein the steps of actuating the fluted screw and the shaving block, and/or actuating the agitator, are conducted at speeds of between 100 and 500 RPM.

* * * * *